United States Patent [19]

Linder et al.

[11] Patent Number: 5,688,487
[45] Date of Patent: Nov. 18, 1997

[54] DIAGNOSTIC IMAGING METHODS USING RHENIUM AND TECHNETIUM COMPLEXES CONTAINING A HYPOXIA-LOCALIZING MOIETY

[75] Inventors: Karen Linder, Kingston; Adrian D. Nunn, Ringoes; David P. Nowotnik, Flemington; Kondareddiar Ramalingam, Dayton; Richard J. DiRocco, Allentown, all of N.J.; William L. Rumsey, Wyndmoor, Pa.; John P. Pirro, Mahwah, N.J.

[73] Assignee: Bracco International B.V., Amsterdam, Netherlands

[21] Appl. No.: 476,604

[22] Filed: Jun. 6, 1995

Related U.S. Application Data

[62] Division of Ser. No. 415,743, Apr. 3, 1995, which is a continuation of Ser. No. 54,120, Apr. 27, 1993, abandoned, which is a continuation-in-part of Ser. No. 976,079, Nov. 13, 1992, abandoned, which is a continuation-in-part of Ser. No. 784,486, Oct. 29, 1991, abandoned.

[51] Int. Cl.$^6$ ................................................. A61K 51/04
[52] U.S. Cl. .............................. 424/1.65; 548/327.5
[58] Field of Search ..................... 424/1.65; 548/327.5; 534/10, 14

[56] References Cited

U.S. PATENT DOCUMENTS

| | | | |
|---|---|---|---|
| 3,369,121 | 2/1968 | Bruno et al. | 250/106 |
| 3,920,995 | 11/1975 | Czaplinski et al. | 250/432 |
| 4,071,613 | 1/1978 | Hunter, Jr. | 424/1 |
| 4,193,979 | 3/1980 | Frank et al. | 424/1.5 |
| 4,272,503 | 6/1981 | Camin et al. | 424/1 |
| 4,311,689 | 1/1982 | Ruddock | 424/1 |
| 4,363,793 | 12/1982 | Blau et al. | 424/1 |
| 4,431,626 | 2/1984 | Henze | 424/1.1 |
| 4,444,690 | 4/1984 | Fritzberg | 534/14 |
| 4,462,992 | 7/1984 | Agrawal et al. | 424/188 |
| 4,615,876 | 10/1986 | Troutner et al. | 424/1.1 |
| 4,638,051 | 1/1987 | Burns et al. | 534/14 |
| 4,758,682 | 7/1988 | Collins et al. | 556/137 |
| 4,789,736 | 12/1988 | Canning et al. | 534/14 |
| 4,818,813 | 4/1989 | Nowotnik et al. | 534/14 |
| 4,849,511 | 7/1989 | Verbruggen | 534/14 |
| 4,871,836 | 10/1989 | Francescono et al. | 534/10 |
| 4,880,616 | 11/1989 | Azuma et al. | 424/1.1 |
| 4,895,960 | 1/1990 | Deutsch | 548/950 |
| 4,897,255 | 1/1990 | Fritzberg et al. | 424/1.1 |
| 4,925,650 | 5/1990 | Nosco et al. | 424/1.1 |
| 4,980,147 | 12/1990 | Fritzberg et al. | 424/1.1 |
| 4,986,979 | 1/1991 | Morgan, Jr. et al. | 424/1.1 |
| 4,988,496 | 1/1991 | Srinivasan et al. | 424/1.1 |
| 5,026,829 | 6/1991 | Deutsch | 534/14 |
| 5,037,631 | 8/1991 | Nosco | 424/1.1 |
| 5,071,636 | 12/1991 | Yamauchi et al. | 424/1.1 |
| 5,075,099 | 12/1991 | Srinivasan et al. | 424/1.1 |
| 5,089,249 | 2/1992 | Fritzberg et al. | 424/1.1 |
| 5,091,514 | 2/1992 | Fritzberg et al. | 534/14 |
| 5,096,693 | 3/1992 | Azuma et al. | 424/1.1 |
| 5,101,041 | 3/1992 | Troutner et al. | 548/518 |
| 5,104,638 | 4/1992 | Nosco | 424/1.1 |
| 5,116,596 | 5/1992 | Bremer et al. | 424/1.1 |
| 5,116,598 | 5/1992 | Nosco | 424/1.1 |
| 5,164,175 | 11/1992 | Bremer et al. | 424/1.1 |
| 5,164,176 | 11/1992 | Gustavson et al. | 424/1.1 |
| 5,187,264 | 2/1993 | Verbruggen | 534/14 |
| 5,302,370 | 4/1994 | Neumeier et al. | 424/1.53 |
| 5,387,409 | 2/1995 | Nunn et al. | 424/1.45 |
| 5,387,692 | 2/1995 | Riley et al. | 548/313.7 |
| 5,506,345 | 4/1996 | Riley et al. | 534/14 |

FOREIGN PATENT DOCUMENTS

| | | |
|---|---|---|
| 61290/90 | 3/1991 | Australia . |
| 92/12147 | 9/1992 | Australia . |
| 92/12148 | 9/1992 | Australia . |
| 2023595 | 3/1991 | Canada . |
| 89/102182.5 | 10/1990 | China . |
| 123504 | 10/1984 | European Pat. Off. . |
| 163119 | 12/1985 | European Pat. Off. . |
| 179608 | 4/1986 | European Pat. Off. . |
| 194843 | 9/1986 | European Pat. Off. . |
| 344724 | 12/1989 | European Pat. Off. . |
| 417870 | 3/1991 | European Pat. Off. . |
| 411491 | 8/1991 | European Pat. Off. . |
| 502595 A2 | 3/1992 | European Pat. Off. . |
| 502594 A1 | 9/1992 | European Pat. Off. . |
| 544412 | 6/1993 | European Pat. Off. . |
| 4025788 A1 | 2/1992 | Germany . |
| 209953 | 7/1984 | New Zealand . |
| 191160 | 7/1986 | New Zealand . |
| 215513 | 10/1988 | New Zealand . |
| 226255 | 9/1990 | New Zealand . |
| 217705 | 11/1990 | New Zealand . |
| 2093451 | 9/1982 | United Kingdom . |
| 89/10759 | 11/1989 | WIPO . |
| 90/05733 | 5/1990 | WIPO . |
| 90/10463 | 9/1990 | WIPO . |
| 91/18908 | 12/1991 | WIPO . |
| 92/07860 | 5/1992 | WIPO . |
| 94/08949 | 4/1994 | WIPO . |

OTHER PUBLICATIONS

Chapman, J.D., "Measurement of Tumor Hypoxia by Invasive and Non-Invasive Procedures: A Review of Recent Clinical Studies", Radiother. Oncol., 20, pp. 13–19 (1991).

(List continued on next page.)

*Primary Examiner*—John Kight
*Assistant Examiner*—Lara Chapman Kelley
*Attorney, Agent, or Firm*—Donald L. Rhoads; George P. Hoare; Rogers & Wells

[57] ABSTRACT

Novel methods, processes and metal complexes attached to a hypoxia-localizing moiety comprising

- a metal, preferably radionuclide of rhenium or technetium;
- a hypoxia-localizing moiety; and,
- a complexing ligand, wherein said ligand and said radionuclide combined have cell membrane permeabilities greater than that of sucrose, are disclosed.

8 Claims, No Drawings

OTHER PUBLICATIONS

Martin, G.V. et al., "Enhanced Binding of the Hypoxic Cell Marker [$^3$H]Fluoromisonidazole in Ischemic Myocardium", J. Nucl. Med., vol. 30, No. 2, 194–201 (1989).

Hoffman, J.M. et al., "Binding of the Hypoxia Tracer [$^3$H]Misonidazole in Cerebral Ischemia". Stroke, 18:168–176 (1987).

Koh, W.J. et al., "Hypoxia Imaging of Tumors Using [F–18] Fluoromisonidazole", J.Nucl.Med., 30,789 (No. 252) (1989).

Biskupiak, J.E. et al., "Synthesis of an (Iodovinyl)misonidazole Derivative for Hypoxia Imaging", J. Med. Chem., 34, pp. 2165–2168 (1991).

Chapman, J.D., "The Detection and Measurement of Hypoxic Cells in Solid Tumors", Cancer, Vo. 54, No. 11, pp. 2441–2449 (1984).

Kedderis, G.L. et al, "The Metabolic Activation of Nitroheterocyclic Therapeutic Agents", Drug Metabolism Reviews, 19(1), pp. 33–62 (1988).

Adams, G.E. et al., "Hypoxia–Mediated Nitro–Heterocyclic Drugs in The Radio–and Chemothrapy of Cancer", Biochemical Pharmacology, vol. 35, No. 1, pp. 71–76 (1986).

Brown, D.M. et al., "Structure–Activity Reationships of 1–Substituted 2–Nitroimidazoles: Effect of Partition Coefficient and Side–chain Hydroxyl Groups on Radiosensitization In Vitro", Radiation Research, 90, pp. 98–108 (1982).

Adams, G.E., et al., "Structure Activity Relationships in the Development of Hypoxic Cell Radiosensitizers. I. Sensitizatoin Efficiency", Int. J. Radiat. Biol., vol. 35, No. 2, pp. 133–150 (1979).

Adams, G.E., et al., "Structure Activity Relationships in the Development of Hypoxic Cell Radiosensitizers. III. Effects of Basic Substituents in Nitromidazole Sidechains", Int. J. Radiat. Biol., vol. 38, No. 6, pp. 613–626 (1980).

Jerabek, P.A., et al., "Synthesis and Biodistribution of $^{18}$F–Labeld Fluoronitroimidazoles: Potential In Vivo Markers of Hypoxic Tissue", Appl. Radiat. Isot. vol. 37, No. 7, pp. 599–605 (1986).

Martin, G.V. et al, "Fluoromisonidazole A Metabolic Marker of Myocyte Hypoxia", Circulation Research, 67, pp. 240–244 (1990).

Shelton, M.E. et al., "In Vivo Delineation of Myocardial Hypoxia During Coronary Occlusion Using Fluorin–14 Fluoromisonidazole and Positron Emission Tomography: A Potential Approach for Idntification of Jeopardized Myocardium", J. Am. College Cardiology, vol. 16, No. 2, pp. 477–485 (Aug. 1990).

Mannan, R.H. et al., "Radioiodinated 1–(5–Iodo–5–deoxy–β–D–arabinofuranosyl)–2–nitroimidazole (Iodazomycin Arabinoside: IAZA): A Novel Marker of Tissue Hypoxia", The Journal of Nuclear Medicine, vol. 32, No. 9, pp. 1764–1770 (1991).

Parker, D., "Harnessing the Kinetic Stability of Macrocyclic Complexes In Vivo," presented at the 16th Int. Symp. on Macrocyclic Chemistry, Univ. of Sheffield, UK (Sep. 1–6, 1991).

Yang, L. et al., "Synthesis of Metronidazole Derivative and Its Distribution in Sarcoma 180 Bearing Mice", J. of Medical Colleges of PLA; 2(3) pp. 265–269 (1987).

Volkert, W.A. et al., "$^{99m}$Tc–propylene amine oxime (99mTc–PnAO); a potential brain radiopharmaceutical", Eur. J. Nucl. Med., 9, pp. 511–516 (1984).

Kung, H.F., et al., "Synthesis and Biodistribution of Neutral Lipid–Soluble Tc–99m Complexes that Cross the Blood–Brain Barrier", The Journal of Nuclear Medicine, 25, pp. 326–332 (1984).

Lever, S.Z. et al., "Design, Preparation, and Biodistribution of a Technetium–99m Triaminedithiol Complex to Asess Regional Cerebral Blood Flow", J. Nucl. Med., 26, pp. 1287–1294 (1985).

Jurisson et al., "Synthesis, Characterization, and X–ray Structural Determination of Technetium (V)–Oxo–Tetradentate Amine Oxime Complexes", Inorg. Chm., 25, pp. 543–549 (1986).

Ding et al., "Review and Prospectives of Brain Radiopphamaceuticals", Nucl. Sci. J., 29(5), pp. 341–348 (1992).

Fattorusso et al., J. Chem. Soc., Daltons Trans., p. 752 (1970).

Moody et al., J. Chem. Soc. Perkin Trans. 1, (1), pp. 18–24 (1972).

Hook et al., Anti–Cancer Drug Res., 4(3), pp. 173–190 (1989).

Orna et al., "Correlation of Kinetic Parameters of Nitroreductase Enzymes with Redox Properties of Nitroaromatic Compounds", J. Biol. Chem., vol. 264, 21, pp. 12379–12384 (1989).

Murmann, K., "The Interaction of 2–Methyl–2–amino–3–butanone Oxime with Nickel (II) and Copper (II) Ions", J. Am. Chem. Soc., pp. 4174–4180 (1958).

Vassian et al., "Aromatization of an Aliphatic Amine Oxime Nickel (II) Complex by Molecular Oxygen", Inorg. Chemistry, vol. 6, No. 11, pp. 2043–2046 (1967).

Murmann et al., "An Unsymmetrical transDinitrocobalt (III) Complex. A Crystal Structure Determination", Inorg. Chem., vol. 12, No. 11, pp. 2625–2631 (1973).

DIAGNOSTIC IMAGING METHODS USING RHENIUM AND TECHNETIUM COMPLEXES CONTAINING A HYPOXIA-LOCALIZING MOIETY

This is a divisional of application Ser. No. 08/415,743, filed Apr. 3, 1995, which is a continuation of 08/054,120, filed Apr. 27, 1993, now abandoned which is a continuation-in-part of 07/976,079, filed on Nov. 13, 1992, now abandoned, which is a continuation-in-part of 07/784,486, filed on Oct. 29, 1991, now abandoned.

BACKGROUND OF THE INVENTION

Many of the procedures presently conducted in the field of nuclear medicine involve radiopharmaceuticals which provide diagnostic images of blood flow (perfusion) in the major organs and in tumors. The regional uptake of these radiopharmaceuticals within the organ of interest is proportional to flow; high flow regions will display the highest concentration of radiopharmaceutical, while regions of little or no flow have relatively low concentrations. Diagnostic images showing these regional differences are useful in identifying areas of poor perfusion, but do not provide metabolic information of the state of the tissue within the region of apparently low perfusion.

There is a need for new radiopharmaceuticals which specifically localize in hypoxic tissue, i.e., tissue which is deficient in oxygen, but still viable. These compounds should be retained in regions which are hypoxic, but should not be retained in regions which are normoxic. A radiopharmaceutical with these properties will display relatively high concentrations in such hypoxic regions, with low concentrations in normoxic and infarcted regions.

Diagnostic images with this radiopharmaceutical should readily allow the identification of tissue which is at risk of progressing to infarction, but still salvagable in, for example, the heart and brain.

It is well known that tumors often have regions within their mass which are hypoxic. These result when the rapid growth of the tumor is not matched by the extension of tumor vasculature. A radiopharmaceutical which localizes preferentially within regions of hypoxia could also be used to provide images which are useful in the diagnosis and management of therapy of tumors as suggested by Chapman, "Measurement of Tumor Hypoxia by Invasive and Non-Invasive Procedures—A Review of Recent Clinical Studies", *Radiother. Oncol.*, 20(S1), 13–19 (1991). Additionally, a compound which localizes within the hypoxic region of tumors, but is labeled with a radionuclide with suitable α- or β-emissions could be used for the internal radiotherapy of tumors.

As reported by Martin et al. ("Enhanced Binding of the Hypoxic Cell Marker [$^3$H] Fluoromisonidazole", *J. Nucl. Med.*, Vol. 30, No. 2, 194–201 (1989)) and Hoffman et al. ("Binding of the Hypoxic Tracer [H-3] Misonidazole in Cerebral Ischemia", *Stroke*, Vol. 18, 168 (1987)), hypoxia-localizing moieties, for example, hypoxia-mediated nitroheterocyclic compounds (e.g., nitroimidazoles and derivatives thereof) are known to be retained in hypoxic tissue. In the brain or heart, hypoxia typically follows ischemic episodes produced by, for example, arterial occlusions or by a combination of increased demand and insufficient flow. Additionally, Koh et al., ("Hypoxia Imaging of Tumors Using [F-18]Fluoronitroimidazole", *J. Nucl. Med.*, Vol. 30, 789 (1989)) have attempted diagnostic imaging of tumors using a nitroimidazole radiolabeled with $^{18}$F. A nitroimidazole labeled with $^{123}$I has been proposed by Biskupiak et al. ("Synthesis of an (iodovinyl)misonidazole derivative for hypoxia imaging", *J. Med. Chem.*, Vol. 34, No. 7, 2165–2168 (1991)) as a radiopharmaceutical suitable for use with single-photon imaging equipment.

While the precise mechanism for retention of hypoxia-localizing compounds is not known, it is believed that nitroheteroaromatic compounds, such as misonidazole, undergo intracellular enzymatic reduction (for example, J. D. Chapman, "The Detection and Measurement of Hypoxic Cells in Tumors", *Cancer*, Vol. 54, 2441–2449 (1984)). This process is believed to be reversible in cells with a normal oxygen partial pressure, but in cells which are deficient in oxygen, further reduction can take place. This leads to the formation of reactive species which bind to or are trapped as intracellular components, providing for preferential entrapment in hypoxic cells. It is necessary, therefore, for hypoxia imaging compounds to possess certain specific properties; they must be able to traverse cell membranes, and they must be capable of being reduced, for example, by reductases such as xanthine oxidase.

The hypoxia imaging agents mentioned above are less than ideal for routine clinical use. For example, the positron-emitting isotopes (such as $^{18}$F) are cyclotron-produced and short-lived, thus requiring that isotope production, radiochemical synthesis, and diagnostic imaging be performed at a single site or region. The costs of procedures based on positron-emitting isotopes are very high, and there are very few of these centers worldwide. While $^{123}$I-radiopharmaceuticals may be used with widely-available gamma camera imaging systems, $^{123}$I has a 13 hour half-life (which restricts the distribution of radiopharmaceuticals based on this isotope) and is expensive to produce. Nitroimidazoles labeled with $^3$H are not suitable for in vivo clinical imaging and can be used for basic research studies only.

The preferred radioisotope for medical imaging is $^{99m}$Tc. Its 140 key γ-photon is ideal for use with widely-available gamma cameras. It has a short (6 hour) half life, which is desirable when considering patient dosimetry. $^{99m}$Tc is readily available at relatively low cost through commercially-produced $^{99}$Mo/$^{99m}$Tc generator systems. As a result, over 80% of all radionuclide imaging studies conducted worldwide utilize this radioisotope. To permit widespread use of a radiopharmaceutical for hypoxia imaging, it is necessary that the compound be labeled with $^{99m}$Tc. For radiotherapy, the rhenium radioisotopes, particularly $^{186}$Re and $^{186}$Re, have demonstrated utility.

EP 411,491 discloses boronic acid adducts of rhenium dioxime and technetium-99m dioxime complexes linked to various nitroimidazoles. Although these complexes are believed to be useful for diagnostic and therapeutic purposes, it would be desirable obtain higher levels of the rhenium or technetium radionuclide in the targeted area, than are achieved with this class of capped-dioxime nitroimidazole complexes. It was demonstrated that the compounds disclosed in EP 411,491 possess reduction potentials similar to 2-nitroimidazole derivatives known to localize in hypoxic regions. In addition, the reduction of these compounds is catalyzed by xanthine oxidase. However, these compounds have poor membrane permeability. Thus, while these compounds might be retained by hypoxic cells, delivery of these compounds to the intracellular domain of these cells may be less than ideal. In addition, the complexes described in EP 411,491 require a heating step to form the hypoxia-localizing radiolabeled compounds. It would be more convenient for the routine use of such hypoxia-localizing radiolabeled compounds to be able to prepare such complexes at ambient temperatures.

Radiolabeled complexes of hypoxia-localizing moieties which retain the biochemical behavior and affinity of such moieties, which are labeled at room temperature with a suitable, easy-to-use radionuclide, and which are capable of providing increased amounts of the desired radionuclide to the targeted area, would be a useful addition to the art.

BRIEF DESCRIPTION OF THE INVENTION

In accordance with the present invention, novel ligands, metal complexes of such ligands, processes for their preparation, and diagnostic and therapeutic methods for their use, are disclosed. In particular, metal complexes, e.g., technetium and rhenium complexes, which are linked to a hypoxia localizing moiety, and wherein the complex has a permeability through cell membranes greater than that of $^{14}C$-sucrose, are disclosed. Exemplary complexes are useful as diagnostic imaging agents in the case of technetium radionuclides and improved agents for radiotherapy in the case of rhenium radionuclides. Suitable novel ligands to form these complexes may include, but are not limited to, di-, tri- or tetradentate ligands forming neutral complexes or technetium or rhenium with the metal preferably in the +5 oxidation state. Examples of such ligands are represented by the formulae

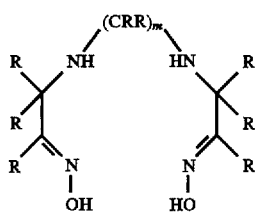

Ia or

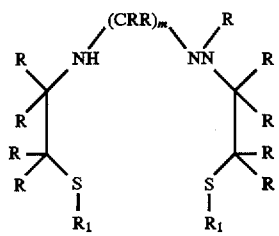

Ib or

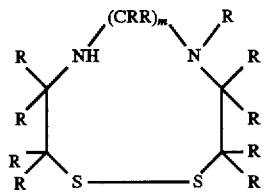

Ic where at least one R is —$(A)_p$—$R_2$ where $(A)_p$ is a linking group and $R_2$ is a hypoxia localizing moiety; and wherein the other R groups are the same, or different and are independently selected from hydrogen, halogen, hydroxy, alkyl, alkenyl, alkynyl, alkoxy, aryl, —$COOR_3$,

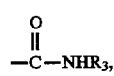

—$NH_2$, hydroxyalkyl, alkoxyalkyl, hydroxyaryl, haloalkyl, arylalkyl, -alkyl-$COOR_3$, -alkyl-$CON(R_3)_2$, -alkyl-$N(R_3)_2$, -aryl-$COOR_3$, -aryl-$CON(R_3)_2$, -aryl-$N(R_3)_2$, 5- or 6-membered nitrogen- or oxygen-containing heterocycle; or two R groups taken together with the one or more atoms to which they are attached form a carbocyclic or heterocyclic, saturated or unsaturated spiro or fused ring which may be substituted with R groups;

$R_1$ is hydrogen, a thiol protecting group or —$(A)_p$—$R_2$;
$R_3$ is hydrogen, alkyl or aryl;
m=2 to 5; and,
p=0 to 20.

It should be apparent that the disulfide of Ic can be reduced to the corresponding dithiol of Ib by known methodology prior to complexing with a metal.

The linking group $(A)_p$ can be any chemical moiety which can serve to physically distance, or otherwise isolate, the hypoxia localizing moiety from the rest of the complex of formula I. This might be important if the hypoxia localizing moiety is likely to be inhibited in its action by the rest of the complex. For example, in the linking group, wherein p is one, A, or the various A units in forming a straight or branched chain if p>1, are independently selected from —$CH_2$—, —$CHR_4$—, —$CR_4R_5$—, —CH=CH—, —CH=$CR_4$—, —$CR_4$=$CR_5$—, —C≡C—, cycloalkyl, cycloalkenyl, aryl, heterocyclo, oxygen, sulfur,

—NH—, —HC=N—, —$CR_4$=N—, —$NR_4$—, —CS—; wherein $R_4$ and $R_5$ are independently selected from alkyl, alkenyl, alkoxy, aryl, 5- or 6-membered nitrogen or oxygen containing heterocycle, halogen, hydroxy or hydroxyalkyl.

In considering the various linking groups known in the art, it is understood that p could be any convenient value depending upon the design choices for the desired complex. Preferably, p is ≦20 and most preferably p≦10.

Listed below are definitions of the terms used to describe the complexes of this invention. These definitions apply to the terms as they are used throughout the specification (unless they are otherwise limited in specific instances) either individually or as part of a larger group.

The terms "alkyl", "alkenyl" and "alkoxy" refer to both straight and branched chain groups. Those groups having 1 to 10 carbon atoms are preferred.

The term "aryl" refers to phenyl and substituted phenyl. Preferred are phenyl and phenyl substituted with 1, 2 or 3 alkyl, haloalkyl, aminoalkyl, alkylaminoalkyl, dialkylaminoalkyl, alkoxy, alkoxyalkyl, halogen, amino, hydroxy, or formyl groups.

The terms "halide", "halo" and "halogen" refer to fluorine, chlorine, bromine and iodine.

The expression "5- or 6-membered nitrogen containing heterocycle" refers to all 5- and 6-membered rings containing at least one nitrogen atom. Exemplary aliphatic nitrogen heterocyclic derivatives have the formula

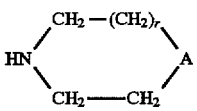

wherein r is 0 or 1 and A is —O—, —N—$R_6$, —S— or —CH—$R_6$ wherein $R_6$ is hydrogen, alkyl, aryl or arylalkyl. Such groups include pyrrolidinyl, piperidinyl, morpholinyl, piperazinyl, 4-alkylpiperazinyl, 4-alkylpiperidinyl, and 3-alkylpyrrolidinyl groups. Also included within the expression "5- or 6-membered nitrogen containing heterocycle" are aromatic groups. Exemplary aromatic groups are pyrrolyl, imidazolyl, oxazolyl, pyrazolyl, pyridinyl, thiophenyl, pyridazinyl, thiazolyl, triazolyl and pyrimidinyl groups. The above groups can be linked via a hereto atom or a carbon atom.

The expression "5- or 6-membered nitrogen or oxygen containing heterocycle" refers to all 5- and 6-membered rings containing at least one nitrogen or oxygen atom. Exemplary groups are those described above under the definition of the expression "5- or 6-membered nitrogen containing heterocycle". Additional exemplary groups are 1,4-dioxanyl and furanyl.

DETAILED DESCRIPTION OF THE INVENTION

It has now been found that metal complexes having a permeability through cell membranes greater than that of $^{14}$C-sucrose provide enhanced products when linked to a hypoxia localizing moiety. Depending upon the metal used, complexes employing such hypoxia-localizing moiety-containing ligands are useful as imaging agents, therapeutic agents, radiosensitizers and hypoxic tissue cytotoxins.

Cell permeability is a property of a cell membrane which describes the mobility of extraneous molecules (permeants) within the internal structure of the membrane (W. D. Stein, "Transport and Diffusion Across Cell Membrane", New York Academic Press Inc. (1986); A. Kotyk, K. Janacek, J. Koryta, Biophysical Chemistry of Membrane Functions, Chichester, UK: John Wiley & Sons, (1988)). Molecules to which the membrane is permeable are able to penetrate through the membrane to reach the environment on the opposite side.

The examples which follow utilize a model of cell permeability based on the studies of Audus and Borchardt ("Bovine Brain Microvessel Endothelial Cell Monolayers as a Model System for the Blood-Brain Barrier", Ann. New York Accad. Sci., 1988; 9–18). The model consists of a cultured monolayer of bovine brain endothelial cells, which form tight intercellular junctions. Transit of compounds across the monolayer reflects the ability of such compounds to cross the intact cell members by passive, active and/or facilitated diffusion mechanisms. The rate of transit is compared with $^{3}H_{2}O$ (a highly permeable tracer) and $^{14}$C-sucrose (a non-permeable tracer). As discussed above, in accordance with the present invention, it has been found that complexes containing a hypoxia localizing moiety and having cell permeability greater than that of sucrose provide benefits to diagnostic and/or therapeutic procedures employing such complexes.

The present complexes, when used with a radioactive metal, provide levels of radionuclide within hypoxic tissue sufficient to enhance diagnostic and therapeutic methods employing such complexes.

Exemplary complexes of the present invention can be shown as

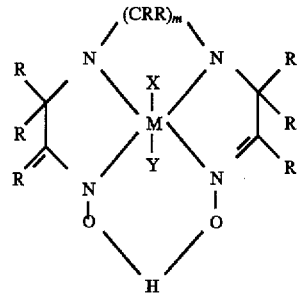

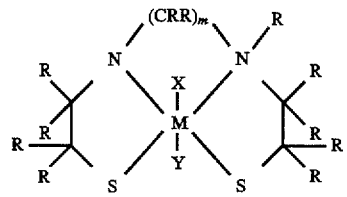

where the R groups are as defined above, where M can be a radioactive or non-radioactive metal which may have other ligand(s) X and/or Y in the unfilled coordination sites. For example, in the cases where M=rhenium or technetium, the

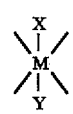

portion can be shown as

Any radioactive metal can be employed in the present complexes, for example, technetium or rhenium for the complexes of Ib', and technetium for the complexes of Ia' Rhenium includes Re-186 and Re-188 radionuclides and mixtures thereof, and may also include Re-185 and Re-187. Technetium includes Tc-99m, Tc-94m and Tc-96.

Complexes of the present invention have not been heretofore disclosed and are useful in that they utilize the properties of the hypoxia localizing group to provide imaging or treatment of hypoxic tissue at a particular site. The complexes of the present invention wherein M is technetium provide highly effective, relatively easy to use diagnostic imaging products which are characterized by a covalent bond between the radionuclide complex and the hypoxia localizing group while substantially retaining the retention properties of the free hypoxia localizing group. It can be appreciated that typical examples of diagnostic uses for the complexes of the present invention when M is technetium include, but are not limited to, imaging of hypoxic tissue, present under pathological conditions in e.g., the heart, brain, lungs, liver, kidneys or in tumors.

In addition to being useful in imaging hypoxic tissue, the present complexes can also be used as blood flow markers, i.e., for perfusion imaging. The initial distribution of the novel complexes is proportional to blood flow and therefore imaging carried out soon after administration is an indicator of perfusion. A short time later, as the present complexes wash out of the normoxic tissue but are retained in the hypoxic tissue, imaging of the hypoxic tissue is realized.

Additionally, the present invention provides stably bound complexes when M is Re for radiotherapeutic indications.

To the extent that hypoxic tissue is known to be present in tumors, Re complexes of the present invention are suitable for radiotherapy. The compounds of this invention when M is Re for use in radiotherapy can be injected into humans and concentrate in hypoxic tissue. This allows for the targeting of radionuclides to the desired sites with great specificity. It is understood, however, that radiotherapy will only be possible in those areas where a sufficient quantity of hypoxic tissue is present so as to provide therapeutic levels of rhenium to the area needing Examples of hypoxia localizing groups are hypoxia-mediated nitro-heterocyclic groups, (i.e., nitro-heterocyclic groups that can be trapped by hypoxia-mediated reduction of the nitro moiety). In addition to those described in the Koh et al. and Hoffman et al. references above, hypoxia-localizing moieties may include those described in "The Metabolic Activation of Nitro-Heterocyclic Therapeutic Agents", G. L. Kedderis et al., *Drug Metabolism Reviews*, 19(1), p. 33–62 (1988), "Hypoxia Medicated Nitro-Heterocyclic Drugs in the Radio- and Chemotherapy of Cancer", G. E. Adams, et al., *Biochem. Pharmacology*, Vol. 35, No. 1, pages 71–76 (1986); "Structure-Activity Relationships of 1-Substituted 2-Nitroimidazoles: Effect of Partition Coefficient and Sidechain Hydroxyl Groups on Radiosensitization In vitro", D. M. Brown et al., *Rad. Research*, 90, 98–108 (1982); "Structure-Activity Relationships in the Development of Hypoxic Cell Radiosensitizers", G. E. Adams et al., *Int. J. Radiat. Biol.*, Vol. 35, NO. 2, 133–150 (1979); and "Structure-Activity Relationships in the Development of Hypoxic Cell Radiosensitizers", G. E. Adams et al., *Int. J. Radiat. Biol.*, Vol. 38, No. 6, 613–626 (1980). These all disclose various nitroheterocyclic moieties suitable for incorporation into the complexes of the present invention and are incorporated herein by reference. These compounds comprise a nitro-heterocyclic group which may include a sidechain, $(A)_p$, which can serve as the linking group connecting the nitro-heterocyclic portion to the rest of the complex of formula I of this invention.

When the hypoxia localizing group is a hypoxia-mediated nitro-heterocyclic group, the linker/localizing group portion of the complex can be represented by

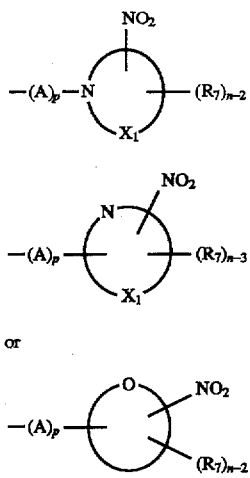

the ring portion being a 5- or 6-membered cyclic or aromatic ring, wherein n is the total number of substitution positions available on the 5- or 6-membered ring;

the one or more $R_7$ substituents are independently selected from hydrogen, halogen, hydroxy, alkyl, aryl, alkoxy, hydroxy-alkyl, hydroxyalkoxy, alkenyl, arylalkyl, arylalkylamide, alkylamide, alkylamine and (alkylamine)alkyl;

$X_1$ can be nitrogen, oxygen, sulfur, $-CR_4$, $-CR_7=$, $CR_7R_7$ or $-CRR-$; and when $(A)_p$ is absent (i.e., p=0) the nitroheterocyclic hypoxia localizing moiety is linked to the rest of the complex of this invention via a nitrogen or carbon atom of the cyclic ring.

The references, above, regarding hypoxia localizing moieties serve to illustrate that the present thinking in the art is that the reduction potential of the nitro-heterocyclic group directly affects its retention in hypoxic tissue. The linking group, $(A)_p$, may therefore be selected not only according to its capacity to distance the hypoxia localizing moiety from the rest of the complex, but also in accordance with its effect on the reduction potential of the hypoxia-mediated nitro-heterocyclic group.

Preferred hypoxia a localizing moieties (shown with the linking groups) are 2-, 4- and 5-nitroimidazoles which can be represented by

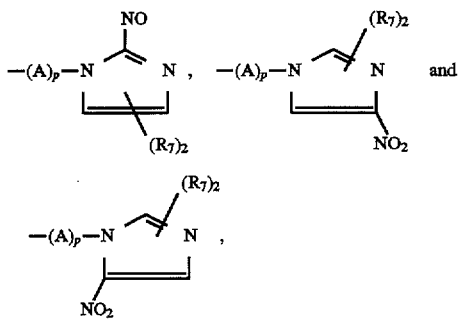

and nitrofuran and nitrothiazole derivatives, such

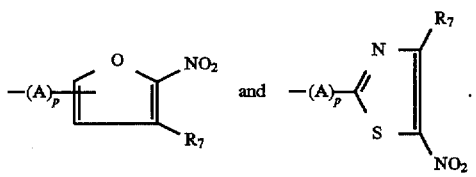

Exemplary groups (including $(A)_p$ linking groups) include, but are not limited to,

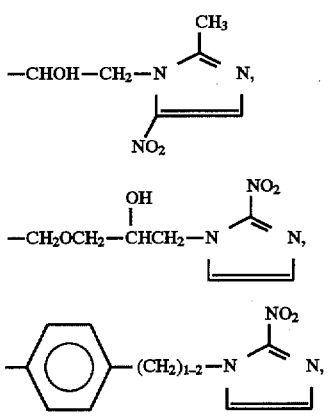

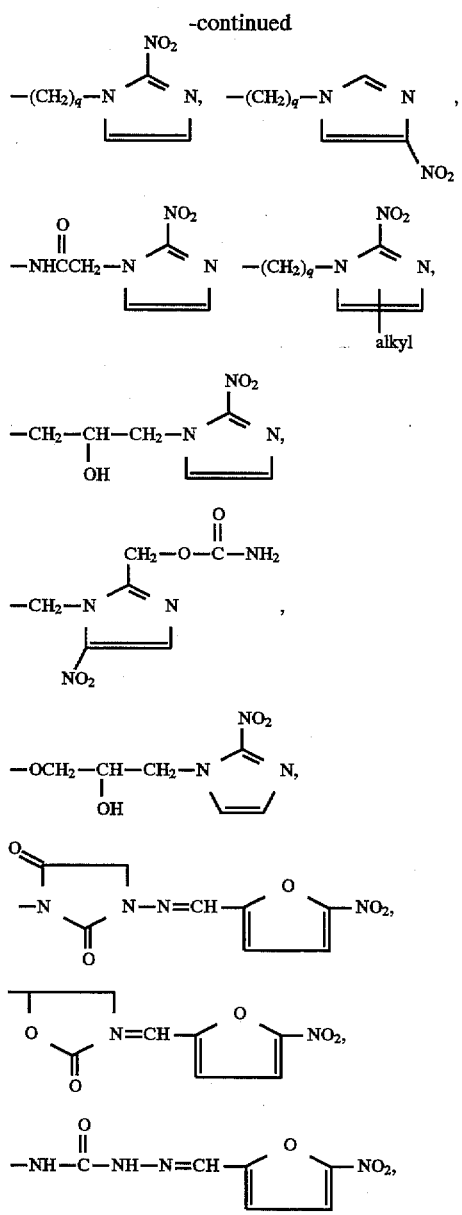

where q=0 to 5. Most preferred are nitroimidazoles and derivatives thereof.

The ligands of formula Ia can be prepared by known methods such as those described in U.S. Pat. No. 4,615,876. For example an alkylene diamine of the formula $$H_2N{-}(CRR)_m{-}NH_2 \quad II$$

is reacted with one equivalent of the chloro oxime $$\underset{Cl}{\underset{|}{R{-}C}}{-}\overset{R}{\underset{|}{C}}{=}NOH \quad III$$

to provide the diamine monooxime (IV: diamine monooxime structure with (CRR)$_m$, NH, NH$_2$, R groups, N–OH)

When the compound of formula Ia includes a hypoxia-localizing moiety (and optional linking group) on one but not both of the oxime portions, compound IV prepared as above, is reacted with $$\underset{Cl}{\underset{|}{R{-}C}}{-}\overset{R_2}{\underset{|}{\underset{(A)_p}{|}}{C}}{=}NOH \quad III'$$

to provide (Ia″: structure with (CRR)$_m$, NH, HN, R groups, N–OH, HO–N, (A)$_p$–R$_2$)

Alternatively, to prepare a compound of the formula Ia″, a compound of the formula III′ may be reacted with a compound of the formula II, and the diamine monoxime formed having the structure:

(structure with (CRR)$_m$, NH, NH$_2$, R, R$_2$–(A)$_p$, N–OH)

reacted with a compound of the formula III.

Compounds of formula Ia having the hypoxia localizing moiety, R$_2$, (and optional linking group) on the alkylene portion

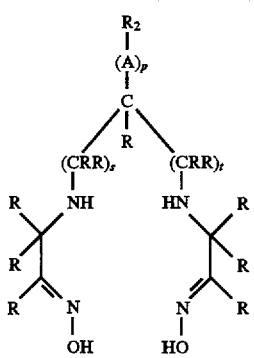

where s=0 to 4 and t=0 to 4 with the proviso that s+t is not greater than 4, can be prepared by reacting a compound of the formula

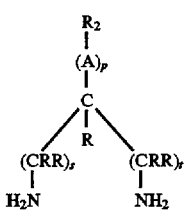

V with two equivalents of a compound of formula III when the oxime portions are to be identically substituted. Similarly, when the oxime portions are to include different substituents, a compound of formula V can be reacted with one equivalent of a first compound of formula III and the so-formed intermediate can thereafter be reacted with one equivalent of a second compound of formula III'.

Exemplary compounds of the formula Ia also include the disubstituted compounds:

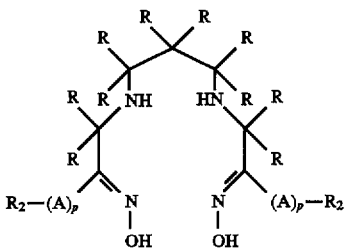

which may be prepared by reacting two equivalents of a compound of the formula III' with one equivalent of a compound of the formula II; and the trisubstituted compounds

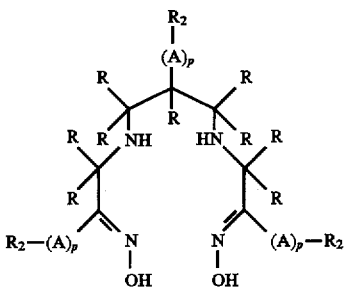

which may be prepared by reacting two equivalents of a compound of the formula III' with one equivalent of a compound of the formula V.

A novel and preferred process for preparing the compounds of formula Ia is outlined below. This novel process is also useful for preparing any alkylene diaminedioxime.

The novel process for the preparation of PnAO derivatives could easily be adapted prepare compounds outside of the scope of disclosure by those skilled in the art.

The novel process involves the use of a haloketone instead of the chloro oxime of compounds III and III' shown above. Thus, in its broad aspects, the novel process involves the preparation of alkylene diaminedioximes by first reacting an alkylene diamine with two equivalents of a haloketone and converting the so-formed diketone to the corresponding alkylene diaminedioxime. Similarly, where different oxime portions are desired the alkylene diamine can be reacted with one equivalent of a first haloketone and then with one equivalent of a second haloketone. The so-formed unsymmetrical diketone is converted to the corresponding dioxime by known methodology as discussed above.

For example, the diamine II of the formula

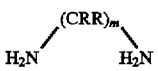

II can be reacted with the haloketone

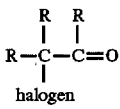

VI where halogen can be Br, Cl, I, F, preferably Br, to provide the diketone

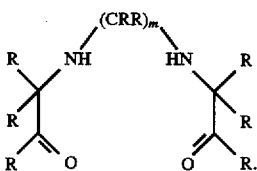

VII

Diketone VII can be converted to the corresponding dioxime product by known methods, e.g., treatment with O-trimethylsilyl hydroxylamine.

When each of the oxime portions of the final product are intended to be different, the novel method herein involves reacting a compound of formula II with a chloro oxime of formula III to provide the diamine monooxime of formula IV. The monooxime IV can thereafter be reacted with the differently substituted haloketone VI to provide the monoketone

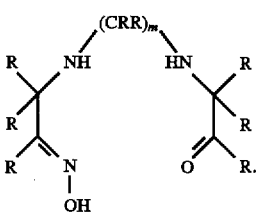

VIII

Monoketone VIII can be converted to the corresponding dioxime product by known methods as described above.

Alternatively, to provide unsymmetrical oximes the diamine of II can be reacted with one equivalent of a first haloketone of VI and the so-formed intermediate can thereafter be reacted with an equivalent of a second haloketone of VI.

Specifically regarding the novel process to prepare products of formula Ia, a diamine of formula V can be reacted with two equivalents of the haloketone VI to provide the diketone intermediates of the formula

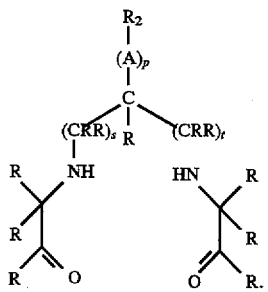　　VII

Diketone VII can be converted to the corresponding dioxime by known methods as described above, to provide the corresponding products of formula Ia where the —(A)$_p$—R$_2$ group is on the alkylene portion of the ligand.

Unsymmetrical compounds of formula Ia can be prepared using such starting materials in the methodology described above, i.e., the sequential coupling of two dissimilar haloketones of VI to an alkylene diamine of II or V.

Similarly, a compound of formula IV can be reacted with a compound of the formula

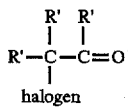　　VI where R'=R with the proviso that one of the R' groups must be —(A)$_p$—R$_2$, e.g.,

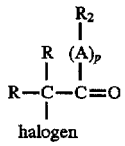　　VI'a to provide, in the case using VI'a, the corresponding ketone-oxime

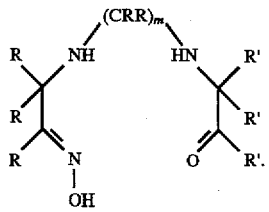　　IX (where one of the R' groups must be —(A)$_p$—R$_2$)

Ketone-oxime IX can be converted to the dioxime of Ia" using known methodology as shown above.

To prepare the compounds of the formula

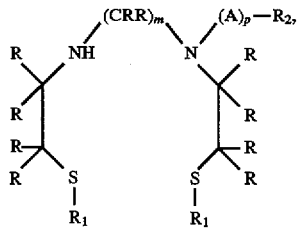　　Ib' a compound of the formula

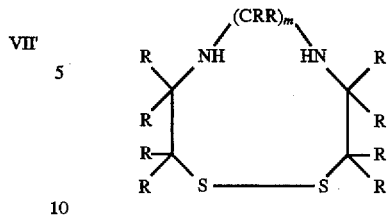　　X (prepared as described in WO 89 10759 to Mallinckrodt) can be coupled with a compound of the formula

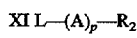　　XI

L—(A)$_p$—R$_2$ where L is a leaving group, e.g., halogen, to provide

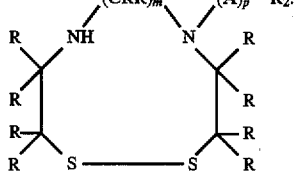　　XII

The tertiary amine disulfide of formula XII can thereafter be reduced to the desired dithiol product of formula Ib' (where R$_1$=H) using known disulfide reducing agents, e.g., tris(2-carboxyethyl)phosphine, dithiothreitol, and the like, as disclosed for example in the aforementioned WO 89 10759. Alternatively, the disulfide X can be reduced to the dithiol form prior to coupling with compound XI. In this case, standard sulfide protection should be employed prior to coupling with XI.

To prepare the compounds of the formula

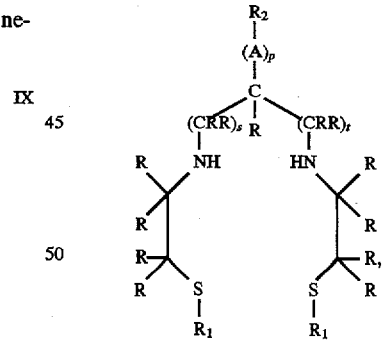　　Ib'"

a compound of formula V can be reacted with a compound of the formula

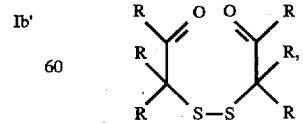　　XIII (prepared as described in Kung et al., "Synthesis and Biodistribution of Neutral Lipid-soluble Tc-99m Complexes that Cross the Blood-Brain-Barrier", *J. Nucl. Med.*, 25, 326–332 (1984)) to provide compounds of the formula

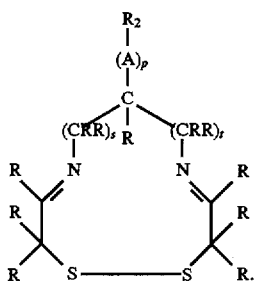

Treatment of compound XIV with a reducing agent, e.g., sodium borohydride, provides intermediates of the formula

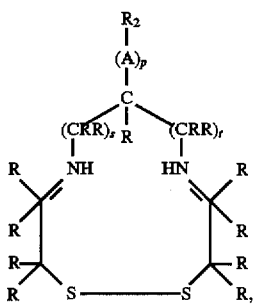

which can be reduced to the corresponding disulfide products of Ib'' using known sulfide reducing agents as discussed above.

Compounds of the formula

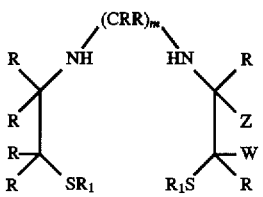

where Z and/or W are —(A)$_p$—R$_2$ and the other of Z and W can be R, can be prepared using known peptide coupling methodology. For example, a compound of the formula

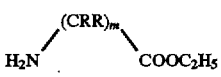

can be coupled with a compound of the formula

to provide intermediates of the formula

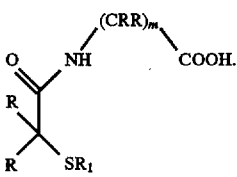

Intermediate XVIII can thereafter be coupled with a compound of the formula

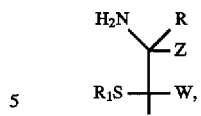

wherein Z and W are as defined above in formula Ib''', to provide

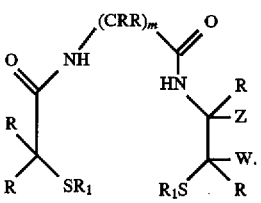

Reduction of compound XX, e.g., by treatment with borane, provides compounds of Ib''' having the following structure

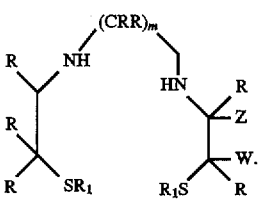

In all of the above reactions described for preparing compounds of this invention, it should be readily apparent to those skilled in the art that sulfur groups, amine groups and ketone groups may need to be protected during the various reactions and that the so-protected resulting products can thereafter be deprotected by known techniques.

All of the examples and the process description below where M is rhenium involve the use of "carrier rhenium"except as otherwise noted. The phrase "carrier rhenium"means that the rhenium compounds used contain non-radioactive rhenium at concentrations of $>10^{-7}$M.

Preparation of the complexes of this invention wherein M is rhenium can be accomplished using rhenium in the +5 or +7 oxidation state. Examples of compounds in which rhenium is in the Re(VII) state are NH$_4$ReO$_4$ or KReO$_4$. Re(V) is available as, for example, [ReOCl$_4$](NBu$_4$), [ReOCl$_4$] (AsPh$_4$), ReOCl$_3$(PPh$_3$)$_2$ and as ReO$_2$(pyridine)$_4^{\oplus}$. Other rhenium reagents known to those skilled in the art can also be used.

Preparation of the complexes of this invention wherein M is technetium can best be accomplished using technetium in the form of the pertechnetate ion. For Tc-99m, the pertechnetate ion can best be obtained from commercially available technetium-99m parent-daughter generators; such technetium is in the +7 oxidation state. The generation of the pertechnetate ion using this type of generator is well known in the art, and is described in more detail in U.S. Pat. Nos. 3,369,121 and 3,920,995. These generators are usually eluted with saline solution and the pertechnetate ion is obtained as the sodium salt. Pertechnetate can also be prepared from cyclotron-produced radioactive technetium using procedures well known in the art.

The formation of the technetium complexes proceeds best if a mixture of pertechnetate ion in normal saline is mixed with the appropriate ligand containing at least one R group of the form —(A)$_p$—R$_2$ where (A)$_p$ is a linking group and R$_2$ is a hypoxia-localizing moiety. An appropriate buffer or physiologically acceptable acid or base may be used to adjust the pH to a value suitable for labeling the ligand. This will vary dependent upon the nature of the ligand; for example, for ligands of type Ia, a pH in the range between ~5.5 to ~9.5 should be used, and preferably a pH value in the range 7.0–8.5. For ligands of the type IIb, a pH value in the range 3–8 should be used, with a pH of ~6.0 being preferred. A source of reducing agent is then added to bring the pertechnetate down to the oxidation state of Tc(V) for chelation with the ligand. Stannous ion is the preferred reducing agent, and may be introduced in the form of a stannous salt such as stannous chloride, stannous fluoride, stannous tartrate, stannous diethylenetriamine pentaacetic acid or stannous citrate, but other suitable reducing agents are known in the art. The reaction is preferably run in an aqueous or aqueous/alcohol mixture, at or about room temperature, using a reaction time of about 1 minute to about 1 hour. The reducing agent should be present at a concentration of 5–50 μg/ml. The ligand should optimally be present in a concentration of 0.5–2 mg/ml.

Alternatively, the technetium complexes of this invention can be prepared by ligand exchange. A labile Tc(V) complex is prepared by the reduction of $TcO_4^-$ in the presence of a ligand which forms a labile technetium complex, such as mannitol, the hydroxycarboxylate ligands glucoheptonate, gluconate, citrate, malate or tartrate at a pH value that is appropriate for the exchange ligand in question (usually 5–8). A reducing agent such as the stannous salts described above is added, which causes the formation of a labile reduced complex of Tc with the exchange ligand. This reduced Tc complex is then mixed with the ligand containing —$(A)_p$—$R_2$ at an appropriate pH value (as described above). The labile exchange ligand is displaced from the metal by the ligand containing the hypoxia-localizing moiety, thus forming the desired technetium complexes of this invention.

It is convenient to prepare the complexes of this invention at, or near, the site where they are to be used. A single, or multi-vial kit that contains all of the components needed to prepare the complexes of this invention (other than the Rhenium or Technetium ion) is an integral part of this invention.

A single-vial kit would contain ligand, a source of stannous salt, or other pharmaceutically acceptable reducing agent, and be appropriately buffered with pharmaceutically acceptable acid or base to adjust the pH to a value as indicated above. It is preferred that the kit contents be in the lyophilized form. Such a single vial kit may optionally contain exchange ligands such as glucoheptonate, gluconate, mannitol, malate, citric or tartaric acid and can also contain reaction modifiers, such as diethylenetriaminepentaacetic acid or ethylenediamine tetraacetic acid. Additional additives, such as solubilizers (for example α-, β- or γ-cyclodextrin), antioxiants (for example ascorbic acid), fillers (for example, NaCl) may be necessary to improve the radiochemical purity and stability of the final product, or to aid in the production of the kit.

A multi-vial kit could contain, in one vial, the ingredients except pertechnetate that are required to form a labile Tc(V) complex as described above. The quantity and type of ligand, buffer pH and amount and type of reducing agent used would depend highly on the nature of the exchange complex to be formed. The proper conditions are well known to those that are skilled in the art. Pertechnetate is added to this vial, and after waiting an appropriate period of time, the contents of this vial are added to a second vial that contains a source of the ligand containing the hypoxia-localizing moiety, as well as buffers appropriate to adjust the pH to its optimal value. After a reaction time of about 1 to 60 minutes, the complexes of the present invention are formed. It is advantageous that the contents of both vials of this multi-vial kit be lyophilized. As described for the single vial kit, additional additives may be necessary to improve the radiochemical purity and stability of the final product, or to aid in the production of the kit.

Alternatively, the multi-vial kit may contain a source of ligand containing the hypoxia localizing moiety in one vial and a source of stannous ion in the second vial. Pertechnetate is added to the vial containing ligand, and then the contents of the second vial are added to initiate labeling. As above, the quantity and type of ligand, buffer pH and reducing agent used would depend on the nature of the hypoxia-localizing ligand and reducing agent used. Again, it is advantageous that the contents of both vials be lyophilized.

The complexes of this invention can be administered to a host by bolus or slow infusion intravenous injection. The amount injected will be determined by the desired uses, e.g. to produce a useful diagnostic image or a desired radiotherapeutic effect, as is known in the art.

Preferred complexes of this invention are those wherein the hypoxia localizing moiety is a hypoxia-mediated nitroheterocyclic group. Most preferred are those wherein the hypoxia localizing moiety is 2-nitroimidazole or a derivative thereof.

In the complexes of the present invention the preferred values for $(A)_p$ are alkyl, oxa-alkyl, hydroxyalkyl, hydroxyalkoxy, alkenyl, arylalkyl, arylalkylamide, alkylamide, alkylamine and (alkylamine)alkyl.

The most preferred values for $(A)_p$ are selected from —$(CH_2)$—$_{1-5}$, —$CH_2$—$CH$=$CH$—$CH_2$—,

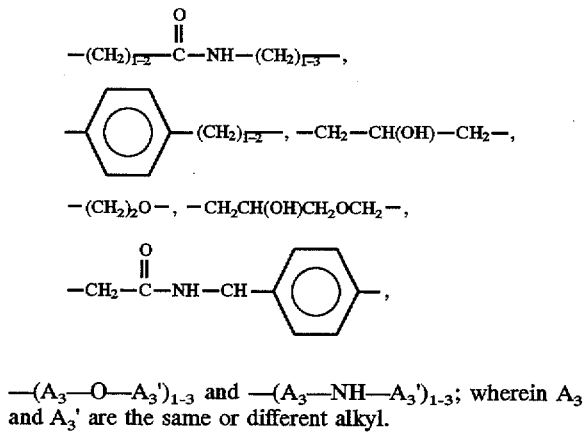

—$(A_3$—$O$—$A_3')_{1-3}$ and —$(A_3$—$NH$—$A_3')_{1-3}$; wherein $A_3$ and $A_3'$ are the same or different alkyl.

Preferred complexes are

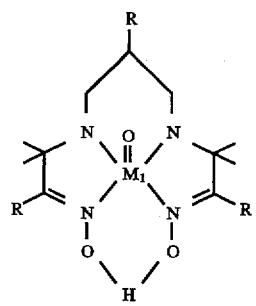

and

-continued

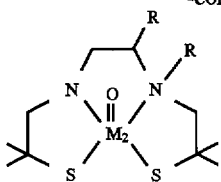

where $M_1$ is technetium and $M_2$ is technetium or rhenium and wherin at least one R group is —$(A)_p$—$R_2$.

The following examples are specific embodiments of this invention.

Example 1

3,3,9,9-Tetramethyl-1-(2-nitro-1H-imidazo-1-yl)-4,8-diazaundecane-2,10-dione dioxime A. N-(Dimethylallyl)-2-nitroimidazole Sodium bicarbonate (0.42 g, 50 mmol) and dimethylallyl bromide (3.28 g, 22 mmol) were added to a suspension of 2-nitroimidazole (2.26 g, 20 mmol) in dry acetonitrile (10 mL). The mixture was stirred under reflux for 16 hours. The solvent was removed under reduced pressure, and the residue was dissolved in ethyl acetate. The solution was filtered, and dried with anhydrous sodium sulfate. Removal of the solvent gave an oil which was recrystallized from petroleum ether (35°–50° C.). Yield 1.83 g, m.p. 48°–49° C. $^1$H NMR (CDCl$_3$) δ7.24 (s, 1H), 7.22 (s, 1H), 5.46 (m, 1H), 5.1 (d, 2H), 1.93 (s, 3H) and 1.90 (s, 3H).

B. 3-Chloro-3-methyl-1-(2-nitro-1H-imidazo-1-yl)-2-nitrosobutane

Concentrated hydrochloric acid (1 mL, 10 mmol) was added slowly to a stirred suspension of the title A compound (1.81 g, 10 mmol) in isoamyl nitrite (1.18 g, 10 mmol) at 0° C., with vigorous stirring. The solution was allowed to come to room temperature, and was stirred at this temperature for 4–6 hours. The precipitated solid was filtered and washed thoroughly with ethanol and dried. Yield 0.31 g, m.p. 102°–108° C. (decomp). $^1$H NMR (DMSO-d$_6$) δ11.9 (s, 1H), 7.25 (s, 1H), 7.05 (s, 1H), 5.45 (s, 2H) and 1.8 (s, 6H).

C. N-(3-Aminopropyl)-1-amino-1,1-dimethyl-2-butanoneoxime

A suspension of 3-chloro-3-methyl-2-nitroisobutane (2.72 g, 20 mmol (prepared according to E. G. Vassian et al., Inorg. Chem., 1967; 6:2043–2046)) in methanol (20 mL) was added dropwise to a solution of 1,3-diaminopropane (8.8 g, 120 mmol) in dry methanol (15 mL). During the addition of diamine, the reaction mixture was stirred at 0°–5° C. After the addition, the reaction mixture was allowed to come to room temperature and then heated under reflux for 6 hours. Methanol was removed by distillation and the residue was treated with water and cooled in ice. The solid was filtered and washed with ice cold water. The filtrate was adjusted to pH 11 with 10% sodium hydroxide and then evaporated to dryness under reduced pressure. The gummy solid was repeatedly extracted with isopropyl ether and the combined filtrate was cooled and filtered. The filtrate was concentrated and the oily residue was again extracted with 1:1 hot ether/hexanes. The combined extracts were cooled and filtered again. Evaporation of the solvents gave a semi-solid which was recrystallized from hexanes/ether twice to yield a colorless solid. Yield: 1.8 g, m.p. 72°–74° C. $^1$H NMR (DMSO-d$_6$) δ2.6 (t, 2H), 2.3 (t, 2H), 1.8 (s, 3H), 1.5 (m, 2H) and 1.2 (s, 6H).

D. 3,3,9,9-Tetramethyl-1-(2-nitro-1H-imidazo-1-yl)-4,8-diazaundecane-2,10-dione dioxide Diethylisopropylamine [2.6 g, 20 mmol) and the title B compound (2.47 g, 10 mmol) were added to a solution of the title C compound (2.0 g, 12 mmol) in dry dichloromethane (15 mL). The resultant mixture was reflexed under nitrogen for 16 hours. The reaction mixture was diluted with 15 mL of anhydrous ether and the precipitated solid was filtered and thoroughly washed with hot 1:1 ether/dichloromethane several times. The dried solid was powdered and stirred with 25 mL of water at 5° C. for 10 minutes. The insoluble material was removed by filtration and washed several times with ice-cold water until only one peak was observed on HPLC analysis. The product was obtained as a pale yellow solid after air drying for several hours. Yield 1.27 g, m.p. 146°–148° C. $^1$H NMR (CD$_3$OD) δ7.4 (s, 1H), 7.18 (s, 1H), 5.4 (s, 2H, NI—CH$_2$), 2.4 (q, 4H, N—CH$_2$), 1.9 (s, 3H, N=C—CH$_3$), 1.6 (m, 2H, C—CH$_2$—C), 1.35 (s, 6H, gem dimethyl) and 1.3 (s, 6H, gem dimethyl). M.S. 384 (M+H) and 401 (M+NH$_4$).

Analysis calc'd for C$_{16}$H$_{29}$N$_7$O$_4$.2.5 H$_2$O: C, 47.33; H, 7.20; N, 24.15.

Found: C, 47.26; H, 7.24; N, 22.58.

Example 2

3,3,9,9-Tetramethyl-1-(4-nitro-1H-imidazo-1-yl)-4,8-diazaundecane-2,10-dione dioxime A. N-(Dimethylallyl)-4-nitroimidazole A solution of 4(5)-nitroimidazole (5.65 g, 50 mmol) in dry dimethylformamide (10 mL) was treated with anhydrous sodium bicarbonate (8.3 g, 100 mmol) and stirred for 15 minutes. 4-Bromo-2-methyl-2-butene was added to the reaction mixture dropwise at room temperature and stirred under nitrogen at 50°–60° C. for 16 hours. Dimethylformamide was removed under reduced pressure and the residue was taken up in ether (100 mL). The ether layer was washed with water and dried over anhydrous sodium sulfate. Evaporation of ether left behind an oil which was repeatedly washed with petroleum ether (5×25 mL). The resulting pale red oil was homogeneous on TLC and was taken on to the next step without further purification. Yield: 7.95 g. $^1$H NMR (CDCl$_3$) δ1.7 (s, 3H, Me), 1.75 (s, 3H, Me), 4.6 (d, 2H, N—CH$_2$), 5.4 (t, 1H, olefinic H), 7.5 (s, 1H, imi H) and 7.8 (s, 1H, imi H). M.S. [M+H]$^+$ 182.

B. 3-Chloro-3-methyl-1-(4-nitro-1H-imidazo-1-yl)-2-nitrosobutane

A solution of the title A olefin (7.9 g, 40 mmol) and isoamyl nitrite (5.3 g, 45 mmol) in dichloromethane was cooled to 0° C. and was treated with dropwise addition of concentrated hydrochloric acid (5 mL, 50 mmol) keeping the reaction temperature at 0°–5° C. The reaction mixture was stirred until all the starting olefin was consumed (by TLC, approximately 2 hours). The precipitated solid was filtered off and washed with ethanol and dried under vacuum at room temperature for 16 hours. The product was used without further purification. Yield: 0.6 g, m.p. 120°–122° C. $^1$H NMR (DMSO-d$_6$) δ1.9 (s, 6H, gem dimethyls), 5.18 (s, 2H, N—CH$_2$), 7.94 (s, 1H, imi H), 8.32 (s, 1H, imi H) and 12.24 (s, 1H, N—OH). M.S. [M+H]$^+$ 247.

C. 3,3,9,9-Tetramethyl-1-(4-nitro-1H-imidazo-1-yl)-4,8-diazaundecane-2,10-dione dioxime To a solution of the title C compound of Example 1 (0.356 g, 2 mmol) in dry dichloromethane (5 mL), diethylisopropylamine (0.36 g, 2 mmol) was added followed by solid title B chloro oxime (0.446 g, 1.8 mmol) and the mixture was refluxed with stirring under nitrogen for 16 hours. The crude product was adsorbed onto flash silica gel and chromatographed. Elution with 15:85 MeOH/CH$_2$Cl$_2$ yielded a gum which was recrystallized from isopropyl ether and acetone three times to yield a colorless solid. Yield: 0.06 g, m.p. 152°–154° C. $^1$H NMR (DMSO-d$_6$) δ1.17 (s, 6H, 2CH$_3$), 1.26 (s, 6H, 2CH$_3$), 1.41 (m, N—CH$_2$—CH$_2$—N, 2H), 1.76 (s, 3H, N═C—CH$_3$), 2.26 (m, 4H, N—CH$_2$), 4.98 (s, 2H, imi N—CH$_2$), 7.9 (s, 1H, imi H), 8.29 (s, 1H, imi H), 10.42 (s, 1H, N—OH) and 11.63 (s, 1H, N—OH).

Analysis calc'd for C$_{16}$H$_{29}$N$_7$O$_4$.H$_2$O: C, 48.96; H, 7.45; N, 24.98;

Found: C, 49.11; H, 7.49; N, 24.76.

Example 3

4,4,10,10-Tetramethyl-1-(2-nitro-1H-imidazo-1-yl)-5,9-diazadodecane-3,11-dione dioxime A. N-(4-Methylpent-3-en-1-yl)-2-nitroindazole To a solution of 2-nitroimidazole (3.0 g, 27 mol) in dry dimethylformamide (25 mL), was added anhydrous sodium bicarbonate (4.2 g, 50 mmol) followed by 5-bromo-2-methyl-2-pentene (5.0 g, 30.67 mmol). The reaction mixture was heated at 60°–70° C. with stirring under nitrogen for 16 hours. Solvent dimethylformamide and the unreacted bromide were removed under reduced pressure (<1 mm) at 50°–60° C. to yield a paste which was dissolved in water (50 mL) and extracted with ethyl acetate (5×50 mL). The combined organic extracts were dried and concentrated to give a brown oil which was recrystallized from petroleum ether (b.p. to yield a yellow solid. Yield: 4.8 g, m.p. 51°–52° C. $^1$H NMR (CDCl$_3$) δ1.55 (s, 3H, CH$_3$), 1.75 (s, 3H, CH$_3$), 2.7 (q, 2H, olefinic CH$_2$), 4.5 (t, 2H, N—CH$_3$), 5.2 (t, 1H, olefinic H), 7.1 (s, 1H, imidazole H), 7.2 (s, 1H, imidazole H), M.S. [M+H]$^+$ 196, [M+NH$_4$]$^+$ 213.

B. 4-Chloro-4-methyl-1-(2-nitro-1H-imidazo-1-yl)-3-nitrosopentane

Isoamyl nitrite (1.4 g, 12 mmol) was added to an ice-cooled solution of the title A olefin (2.17 g, 12 mmol) in dichloromethane (5 mL), and the mixture was treated with a dropwise addition of concentrated hydrochloric acid, keeping the temperature of the reaction mixture below 0° C. After stirring for an additional 2 hours, the solid formed was isolated by filtration and washed with ice cold ethanol. The pale yellow product was dried under vacuum and used in the next step without further purification. Yield: 1.7 g, m.p. 105°–107° C. $^1$H NMR (DMSO-d$_6$) δ1.7 (s, 6H, gem dimethyl), 2.9 (t, 2H, oxime CH$_2$), 4.7 (t, 2H, N—CH$_2$), 7.1 (s, 1H, imidazole H) and 7.5 (s, 1H, imidazole H). M.S. [M+H]$^+$ 261, [M+NH$_4$]$^+$ 278.

C. 4,4,10,10-Tetramethyl-1-(2-nitro-1H-imidazo-1-yl)-5,9-diazadodecane-3,11-dione dioxime Sodium bicarbonate (0.42 g, 5 mmol) was added to a solution of the title C compound of Example 1 (0.86 g, 5 mmol) in dry tetrahydrofuran (10 mL), and then the reaction mixture was treated with the title B compound (1.3 g, 5 mmol). The mixture was heated with stirring under reflux for 6 hours. The solution was reduced in volume to about 5 mL and the crude product was treated with 5 g of flash silica gel and then dried under vacuum to a free flowing powder. This powder was loaded on to a silica gel column and chromatographed three times. The product was eluted as a low melting solid with 9:1 dichloromethane/methanol. Yield: 0.13 g, m.p. 65°–67° C. $^1$H NMR (DMSO-d$_6$) δ1.2 (s, 12H, 4 CH$_3$), 1.45 (m, 2H, 5 CH$_2$), 1.8 (s, 3H, ═N—CH$_3$), 2.3 (m, 4H, N—CH$_2$), 2.85 (t, 2H, ═N—CH$_2$), 4.8 (t, 2H, imidazole N—CH$_2$), 7.2 (s, 1H, imidazole H), 7.6 (s, 1H, imidazole H), 10.4 (s, 1H, N—OH), 10.85 (s, 1H, N—OH). M.S. [M+H]$^+$ 398.

Analysis calc'd for C$_{17}$H$_{31}$N$_7$O$_4$: C, 51.37; H, 7.86; N, 24.67;

Found: C, 51.89; H, 7.89; N, 23.27.

Example 4

6-Hydroxy-3,3,9,9-tetramethyl-1-(2-nitro-1H-imidazo-1-yl)-4,8-diazaundecane-2,10-dione dioxime A. N-(3-Amino-2-hydroxypropyl)-1-amino-1,1-dimethyl-2-butanoneoxime 3-Chloro-3-methyl-2-nitrosobutane (6.75 g, 0.05 mol) was added portionwise to a cooled (0° C.) solution of 1,3-diamino-2-hydroxypropane (14 g, 0.155 mol) in methanol (75 mL). After the addition, the reaction mixture was allowed to warm to room temperature and heated under reflux for 12 hours. Methanol was removed on a rotary evaporator. The residue was neutralized with methanolic ammonia. Excess methanol was removed on a rotary evaporator. The residue was dissolved in dioxane-water (2:1, 300 mL) and the solution was cooled to 0° C. Sodium carbonate (31.8 g, 0.3 mol) was added to this mixture followed by di-t-butyl dicarbonate (65.47 g, 0.3 mol). The reaction mixture was stirred at 0° C. for 2 hours and at room temperature for 6 hours.

Dioxane and water were removed on a rotary evaporator and the residue was poured into water and extracted with ethyl acetate. The ethyl acetate solution was washed with water and dried with sodium sulfate. Ethyl acetate was removed on a rotary evaporator and the residue was chromatographed over silica gel (hexane-ethyl acetate 50: 50). Di-t-Boc-1,3-diamino-2-hydroxypropane eluted in the earlier fractions. These fractions were collected and solvent was evaporated to yield a thick oil. Yield 4.9 g. This was treated with methanolic hydrochloric acid (25 mL) at room temperature for 2 hours. Methanol was removed under reduced pressure and the solid obtained was neutralized with methanolic ammonia to yield the product as a white solid. This was used for the next step without further purification. Yield: 3.98 g. $^1$H NMR (D$_2$O) δ1.54 (s, 6H, C(CH$_3$)$_2$), 1.80 (s, 3H, CH$_3$), 2.92–3.32 (m, 4H, CH$_2$), 4.18 (m, 1H, CHOH).

B. 6-Hydroxy-3,3,9,9-tetramethyl-1-(2-nitro-1H-imidazo-1-yl)-4,8-diazaundecane-2,10-dione dioxime dihydrochloride The title B compound of Example 1 (1.6 g, 0.0065 mol) was added to a slurry of the title A compound (1.4 g, 0.0075 mol) and diisopropylethylamine (1 g, 0.0078 mol) in acetonitrile (10 mL) and the mixture was stirred at room temperature for 24 hours. Acetonitrile was removed on a rotary evaporator and the thick yellow oil obtained was chromatographed over silica gel (CH$_2$Cl$_2$:CH$_3$OH, (9:1) and CH$_2$Cl$_2$:CH$_3$OH, (9:2)). Fractions containing the product were combined and solvent was evaporated to yield a thick oil. $^1$H NMR of the oil indicated the presence of the product and diisopropylethylamine. The oil was left under vacuum for 12 hours. The thick oil was then triturated several times with methylene chloride to remove the diisopropylethylamine. The residue was then dissolved in water and freeze dried. Yield: 0.65 g, m.p. 114°–115° C. $^1$H NMR (D$_2$O) δ1.33, 1.44 and 1.88 (s, 15H, CH$_2$), 2.42–2.92 (m, 4H, CH$_2$), 3.90 (m, 1H, CHOH), 5.34 (s, 2H, CH$_2$N), 7.14 and 7.31 (s, 2H, C═N and C═C). M.S. calc'd 400.2308; found: 400.2298.

Example 5

3,3,9,9-Tetramethyl-6-((2-nitro-1H-imidazo-1-yl)acetamido)-4,8-diazaundecane-2,10-dione dioxime A. (N,N'-bis-t-Boc)-2-mesyloxypropane-1,3-diamine Methanesulfonyl chloride (6.01 g, 4.1 mL, 0.0525 mol) was added to an ice-cooled (0° C.) solution of 1,3-Bis-N-t-Boc-2-hydroxypropane (14.5 g, 0.05 mol) and triethylamine (6.07 g, 8.5 mL) in methylene chloride over a period of 45 minutes. The reaction mixture was then stirred at 0° C. for 1 hour and at room temperature for 12 hours. Precipitated triethylamine hydrochloride was removed by filtration, and the filtrate was evaporated to dryness under reduced pressure. The residue was poured into water. The resultant solid was isolated by filtration, air dried and used without further purification. Yield 18 g, m.p. 139°–140° C. $^1$H NMR (CDCl$_3$) δ1.41 (s, 18H), 3.08 (s, 3H), 3.30 (m, 2H), 3.45 (m, 2H), 4.65 (m, 1H), 5.15 (bs, 2H).

B. 1.3-Bis-N-t-Boc-2-azidopropane

Sodium azide (6.5 g, 0.1 mol) was added to a solution of the title A compound (9.2 g, 0.025 mol) in dry dimethylformamide (50 mL), and the mixture was stirred at 70° C. for 12 hours. The reaction mixture was cooled and poured into water. The precipitated solid was isolated by filtration, and was washed with water and air dried. Yield 6.45 g, m.p. 90°–91° C. $^1$H NMR (CDCl$_3$) δ1.45 (s, 18H), 3.15 (m, 2H), 3.35 (m, 2H), 3.64 (m, 1H), 5.04 (bs, 2H).

C. 1,3-Bis-N-t-Boc-1,2,3-triaminopropane

10% Palladium-on-carbon (1 g) was added to a solution of the title B compound (6.5 g, 0.0205 mol) in methanol (25 mL) and hydrogenated at 50 psi for 12 hours. The catalyst was removed by filtration and methanol was removed on a rotary evaporator. The resultant oil solidified on standing. Yield 4.82 g (82%), m.p. 94°–96° C. $^1$H NMR (CDCl$_3$) δ1.42 (s, 18H, Boc), 2.89 (m, 1H, CHNH$_2$), 3.12 (m, 4H, CH$_2$), 5.20 (m, 2H, NH).

D. 1,3-Bis-N-t-Boc-2-(2-nitroimidazol-1-yl)-acetamido-1,3-diaminopropane

Carbonyldiimidazole (3.08 g, 0.019 mol) was added to a solution of 2-(2-nitroimidazol-1-yl) acetic acid (3.1 g, 0.018 mol (prepared according to P. Webb et al., *J. Lab. Cmpds. Radiopharm.*, 1990; 28:265–271)) in dimethylformamide (25 mL). The mixture was stirred at room temperature for 45 minutes. 1,3-Bis-N-t-Boc-2-aminopropane (5.3 g, 15 0.018 mol) was added and the resultant mixture was stirred at 50° C. for 12 hours. Dimethylformamide was removed under vacuum and the residue was treated with water. The solid which formed was isolated by filtration and air dried. Yield 6.5 g. $^1$H NMR (CDCl$_3$) δ1.44 (s, 18H), 2.90 (m, 1H), 3.08 (m, 4H), 5.24 (bs, 2H).

E. 2-(2-Nitroimidazol-1-yl)acetamido-1,3-diaminopropane dihydrochloride

The title D compound (6.5 g) was dissolved in methanolic hydrochloric acid (20 mL), and the reaction mixture was stirred at room temperature for 1 hour. The diamine dihydrochloride was precipitated by the addition of dry ether (200 mL). Yield 4.25 g. $^1$H NMR (dihydrochloride in D$_2$O) δ3.08–3.35 (m, 4H), 4.51 (m, 1H), 5.31 (s, 2H), 7.19 (s, 1H), 7.43 (s, 1H). $^1$H NMR (free base in D$_2$O) δ3.01–3.28 (m, 4H), 4.45 (m, 1H), 5.21 (s, 2H), 7.15 (S, 1H), 7.39 (s, 1H).

F. 3,3,9,9-Tetramethyl-6-((2-nitro-1H-imidazo-1-yl) acetamido)-4,8-diazaundecane-2,10-dione Sodium hydrogen carbonate (5.88 g, 0.07 mol) and 2-bromo-2-methylbutan-3-one (6.1 g, 0.07 mol (prepared according to W. Pfleiderer et al., *Ann. Chem.*, 1966; 99:3008–3021)) were added to a slurry of the title E compound (4.25 g, 0.0135 mol) in dry dimethylformamide (40 mL). The reaction mixture was stirred at 45° C. for 12 hours. Methylene chloride (200 mL) was added to this reaction mixture, and the insoluble material was removed by filtration. Methylene chloride was removed on a rotary evaporator and the dimethylformamide was removed under vacuum. The residue was chromatographed on silica gel and eluted with ethyl acetate-methanol (9:1). Fractions containing the product were collected. Evaporation of the solvent yielded the desired diaminediketone. Yield 2.56 g. A sample of the product was crystallized from hexane, to provide product with a m.p. of 96°–97° C. $^1$H NMR (D$_2$O) δ1.22 (d, 12H, C(CH$_3$)$_2$), 2.12 (s, 6H, CH$_3$), 2.32–2.58 (m, 4H), 3.9 (m, 1H, CH), 5.21 (s, 2H), 7.15 (S, 1H), 7.39 (s, 1H). M.S. (M+H)$^+$=411.

G. 3,3,9,9-Tetramethyl-6-((2-nitro-1H-imidazo-1-yl) acetamido)-4,8-diazaundecane-2,10-dione dioxime O-Trimethylsilyl hydroxylamine (1 g, 1.22 mL, 0.01 mol) was added to a solution of the title F compound (550 mg, 0.00133 mol) in methylene chloride (2 mL). The reaction mixture was allowed to stand at room temperature for 24 hours. Methanol (2.0 mL) was added to the reaction mixture and the solvent was removed on a rotary evaporator. The resultant solid was crystallized from water. Yield 329 mg, m.p. 72°–73° C. $^1$H NMR (D$_2$O) δ1.12 (s, 12H, C(CH$_3$)$_2$), 1.72 (s, 6H, CH$_3$), 2.22–2.45 (m, 4H), 3.8 (m, 1H, CH), 5.1 (s, 2H), 7.15 (s, 1H), 7.39 (s, 1H). M.S. (M+H)$^+$=441.

Analysis calc'd for C$_{18}$H$_{32}$N$_8$O$_5$: C, 49.08; H, 7.32; N, 25.44;

Found: C, 49.42; H, 7.54; N, 25.65.

Example 5a 3,3,9,9-Tetramethyl-6-((2-nitro-1H-imidazo-1-yl)ethyl)-4,8-diazaundecane-2,10-dione dioxime A. Benzyl 2-methylsulphonyloxyethyl ether Triethylamine (18 g, 0.178 mol) was added to a solution of benzyloxyethanol (25 g, 0.165 mol) in methylene chloride (200 mL). The solution was cooled to 0° C. and methanesulfonyl chloride (19.95 g, 0.174 mol) was added dropwise over a period of 0.5 hour. After the addition was complete the reaction mixture was stirred at 0° C. for an additional 1 hour and at room temperature for 12 hours. The precipitated triethylamine hydrochloride was filtered and washed with dry ether. The combined filtrate and the were concentrated to a thick viscous oil (37 g). $^1$H NMR (CDCl$_3$) δ3.15 (s, 3H, CH$_3$), 3.82 (t, 2H), 4.52 (t, 3H), 4.67 (s, 2H) and 7.42 (m, 5H, AT-H).

B. Benzyl 2-bromoethyl ether

The title A compound (37 g, 0.16 mol) was added to a solution of lithium bromide (86.85 g, 0.8 mol) in acetone (300 mL), and the resulting solution was heated under gentle reflux for 12 hours. The reaction mixture was cooled and the acetone was removed on a rotary evaporator. The residue was taken up in ether and washed successively with water and dried. Evaporation of ether afforded a liquid which was distilled under reduced pressure to yield the product (32 g), b.p. 95° C./1.5mm. $^1$H NMR (CDCl$_3$) δ3.60 (t, 2H), 3.90 (t, 3H), 4.70 (s, 2H) and 7.46 (m, 5H, Ar—H).

C. Diethyl 1-(2-Benzyloxyethyl)malonate

Diethyl malonate (8.0 g, 0.05 mol) was added to a solution of sodium ethoxide prepared from 1.2 g (0.052 g atom) of sodium in ethanol (300 mL). The title B compound (10.75 g, 0.05 mole) was added dropwise to this solution and the reaction mixture was heated under reflux for 12 hours. Ethanol was evaporated on a rotary evaporator and the residue was poured into water and extracted with ether and dried with sodium sulfate. Evaporation of ether gave an oil. This was distilled under vacuum to yield 9.5 g of the product, b.p. 185° C./2 mm. $^1$H NMR (CDCl$_3$) δ1.21 (t, 6H), 2.24 (q, 2H), 3.52 (m, 3H), 4.15 (m, 4H), 4.45 (s, 2H) and 7.31 (m, 5H, Ar—H).

D. 1-(2-Benzyloxyethyl)malonamide

The title C compound (9.0 g) was treated with ethanolic aqueous ammonia and the reaction mixture was stirred at room temperature for 12 hours. Evaporation of the solvent gave a white solid which was crystallized from water to yield the product (4.5 g), m.p. 165°–70° C. $^1$H NMR (DMSO-d$_6$) δ1.92 (m, 2H), 3.14 (t, 1H), 3.35 (m, 2H), 4.12 (s, 2H), 7.05 (s, 2H), 7.22 (s, 2H) and 7.34 (m, 5H, Ar—H).

E. 1,3-Diamino-N,N'-di-t-Boc-2-benzyloxyethylpropane

BH$_3$-THF complex (1M, 750 mL) was added to a slurry of the title D compound (28.0 g, 0.118 mol) in dry tetrahydrofuran (500 mL) over a period of 1 hour and the reaction mixture was stirred at room temperature for 48 hours. Excess borane was decomposed by the dropwise addition of water. Dilute hydrochloric acid was added until the solution became acidic. Tetrahydrofuran was removed on a rotary evaporator. The residue was suspended in dioxane-water (2:1, 500 mL). Sodium carbonate (31.8 g, 0.3 mol) was added and the mixture was cooled to 0° C. Di-t-butyl dicarbonate (58.9 g, 0.27 mol) was added and the mixture was stirred at 0° C. for 2 hours and at room temperature for 12 hours. Dioxane-water was removed on a rotary evaporator and the residue was treated with water. The crude product was extracted with ethyl acetate, and the extract was dried over sodium sulfate. Ethyl acetate was removed on a rotary evaporator and the thick oil obtained was chromatographed over silica gel (hexane:ethyl acetate, 7:3) to yield 27 g of the title E compound. $^1$H NMR (CDCl$_3$) δ1.41 (s, 18H, tBoc), 1.52 (m, 2H, CHCH), 1.72 (m, 1, CH), 2.9–3.2 (m, 4H, CH(CH$_2$-NHtBoc)$_2$), 3.6 (m, 1H, OCH$_2$), 4.5 (s, 2H, Ph H$_2$), 5.2 (m, 2H, NH), 7.3 (m, 5H, ArH).

F. 1,3-Diamino-N,N'-di-t-Boc-2-hydroxyethylpropane

Palladium on carbon (10%, 1 g) was added to a solution of the title E compound (7.5 g) in methanol (50 mL) and hydrogenated at 50 psi for 24 hours. Methanol was removed on a rotary evaporator, 1,3-bis-N-t-butyloxycarbonyl-2 (2-hydroxyethyl)propane was obtained as a white solid (5 g), m.p. 101°–02° C. $^1$H NMR (CDCl$_3$) δ1.45 (s, 18H, tBoc), 1.65 (m, 1H, CH), 2.9–3.2 (m, 6H, CH(CH$_2$NHtBoc)$_2$ and CH$_2$CH), 3.78 (m, 2H, OCH$_2$), 5.2 (m, 2H, NH).

G. 1,3-Diamino-N,N'-di-t-Boc-2-mesyloxyethylpropane

Triethylamine (1.36 g, 1.89 mL, 0.0134 mol) was added to a solution of hydroxyethyl derivative (3.5 g, 0.0112 mol) in methylene chloride was added and the mixture was cooled to 0° C. Methanesulfonyl chloride (1.43 g, 0.0125 mol) was added slowly over a period of 0.5 hour and the reaction mixture was stirred at 0° C. for 1 hour and at room temperature for 12 hours. Methylene chloride was removed and the solid obtained was crystallized from hexane to yield 3.9 g of the title G compound, m.p. 109°–10° C. $^1$H NMR (CDCl$_3$) δ1.41 (s, 18H, t. Boc), 1.52 (m, 2H, CH$_2$CH), 1.72 (m 1H, OH), 3.0 (s, 3H, CH$_3$), 3.1 (m, 4H, CH(CH$_2$NHtBoc)$_2$), 4.45 (m, 2H, OCH$_2$), 5.15 (m, 2H, NH).

H. 2-Bromoethyl-1,3-diamino-N,N'-di -t-Boc propane

A solution of the title G compound (1.98 g, 0.5 mol) and lithium bromide (4.34 g, 0.05 mol) in acetone (50 mL) was stirred at room temperature for 24 hours. Acetone was removed on a rotary evaporator and the title H compound as obtained as an oil (1.5 g). This product was used without further purification.

I. 1,3-Diamino-N,N'-di-t-Boc-2-(2-(2-nitro-1H-imidazo-1-yl)ethylpropane

Sodium hydride (0.12 g, 0.005 moL) was added to a suspension of 2-nitroimidazole (0.56 g, 0.005 mol) in dry acetonitrile (5 mL), and the mixture was stirred at room temperature for 15 minutes. Acetonitrile was removed under vacuum and the residue was dissolved in dry dimethylformamide (5.0 mL). The title H compound (1.14 g, 0.003 mol was added to the dimethylformamide solution and the mixture was heated in an oil bath at 110° C. for 2 hours. The mixture was cooled, and dimethylformamide was removed under vacuum. The residue was treated with water and extracted with methylene chloride. The methylene chloride solution was separated, dried over sodium sulfate, and solvent was removed on a rotary evaporator. The crude product was chromatographed over silica gel (hexane:ethyl acetate, 50:50). The fractions containing the product were collected and evaporated to afford the product as a thick yellow oil which solidified on standing. Yield 0.52 g. $^1$H NMR (CDCl$_3$) δ1.35 (s, 18H, Boc)0 1.6 (m, 2H, CH(CH$_2$CH$_2$N), 3.12 (m, 5H, CH(CH$_2$NH)$_2$ and CH), 4.50 (t, 2H, CH(CH$_2$CH$_2$N), 5.12 (m, 2H, NH), 7.0 and 7.25 (s, 2H, CH=CH).

J. 3,3,9,9-Tetramethyl-6-((2-nitro-1H-imidazo-1-yl)ethyl)-4,8-diazaundecane-2,10-dione The t-Boc protecting groups were removed from the title I compound by treatment with methanolic hydrochloric acid (2 mL). Methanol was removed under vacuum to afford the dihydrochloride. 1H NMR (D$_2$O) δ2.0 (m, 2H, CH(CH$_2$CH$_2$N), 2.20 (m, 1H, CH), 3.12 (d, 4H, CH(CH$_2$NH), 4.50 (t, CH(CH$_2$CH$_2$N), 7.10 and 7.42 (s, 2H, CH=CH). The dihydrochloride was neutralized with ethanolic ammonia and the diamine free base obtained was used as such without further purification.

3-Bromo-3-methylbutan-2-one (0.5 g, 3.0 mmol) was added to a mixture of the diamine (0.2 g, 1 mmol) and sodium bicarbonate (0.25 g, 3.0 mmol) in dimethylformamide (2.0 ml ) and the mixture was stirred at 50° C. for 24 hours. Dimethylformamide was removed under vacuum and the crude product was chromatographed over silica gel (CH$_2$Cl$_2$:CH$_3$OH, 9:1, 8:2). Fractions containing the product were collected and evaporated to give the title J compound (110 mg) as a thick oil. NMR (D=O) δ1.33 (d and m, 13H, C(CH$_3$) and 1.80 (m, 2H, CH(CH$_2$CH$_2$N), 2.19 (s, 6H, CH$_3$), 2.65 (m, 4H, CH(CH$_2$NH), 4.40 (t, 2H, CH(CH$_2$C H$_2$N), 7.10 and 7.39 (s, 2H, CH=CH).

K. 3,3,9,9-Tetramethyl-6-((2-nitro-1H-imidazo-1-yl)ethyl)-4,8-diazaundecane-2,10-dione dioxime Diketone (65 mg) was dissolved in dry methylene chloride (0.5 ml) and treated with trimethylsilyl hydroxylamine (0.3 mL). The reaction mixture was heated under reflux for 24 hours. Methylene chloride was removed and the residue was treated with methanol. Evaporation of methanol afforded the product as a thick paste which was dissolved in water and freeze dried to yield 62 mg of the title K compound, m.p. 174°–76° C. $^1$H NMR (D$_2$O) δ1.2 (d and m, 13H, C(CH$_3$) and CH), 1.75 (s and m, 8H, CH(CH$_2$CH$_2$N) and CH$_3$), 2.55 (m, 4H, CH(CH$_2$NH), 4.36 (t, 2H, CH(CH$_2$CH$_2$N), 7.06 and 7.34 (s, 2H, CH=CH), MS: (M+H)$^+$=412$^+$.

Analysis calc'd for C$_{18}$H$_{35}$N$_7$O$_4$.4H$_2$O: C, 44.70; H, 7.30; N, 20.29;

Found: C, 45.08; H, 7.14; N, 20.18.

Example 5b 5,8-Diaza-1,2-dithia-5-(2-(2-nitro-1H-imidazo-1-yl)ethyl)-3,3,10,10-tetramethylcyclodecane A. 5,8-Diaza-1,2-dithia-3,3,10,10-tetramethylcyclodecane Sodium borohydride (9.12 g, 0.24 mole) was added in portions at room temperature with stirring over a period of about 2 hours to a solution of 5,8-diaza-1,2-dithia-5-3,3,6,6-tetramethylcyclodeca-4,8-diene (9.2 g, 40 mmol, reported by H. F. Kung, M. Molnar, J. Billings, R. Wicks, M. Blau, "Synthesis and Biodistribution of Neutral Lipid-Soluble Tc-99m Complexes that Cross the Blood-Brain-Barrier", *J. Nucl. Med.*, 1984; 25:326–332) in ethanol (500 mL). The reaction mixture stirred at room temperature for an additional 20 hours. Ethanol was removed under reduced pressure and the crude product was chromatographed over a flash silica gel column. Elution with 9:1 dichloromethane/methanol furnished the cyclized product (described by S. Z.

Lever, "Correction: Design, Preparation and Biodistribution of a Technetium-99m Triaminedithiol Complex to Assess Regional Cerebral Blood Flow", *J. Nucl. Ned.*, 1987; 28:1064–1065) followed by the required diamine on continued elution with 9:1:0.1 dichloromethane/methanol/ammonia. The product was recrystallized from petroleum ether to yield a colorless solid. Yield: 0.66 g, m.p. 58°–60° C.

B. 5,8-Diaza-1,2-dithia-5-(2-(2-nitro-1H-imidazol-yl)ethyl]-3,3,10,10-tetramethylcyclododecane Potassium fluoride on celite (0.82 g, 14.1 mmol) was added to a solution of the title A compound (0.66 g, 2.82 mmol) in dry acetonitrile (10 mL) and the reaction mixture was stirred for 5 minutes. Bromoethyl nitroimidazole (0.65 g, 2.82 mmol, described by D.C. Heimbrook, K. Shyam, A. C. Sartorelli, "Novel 1-haloalkyl-a-nitroimidazole Bioreductive Alkylating Agents", *Anti-Cancer Drug Design*, 1988, 2:339–350) was added and stirred under nitrogen and under reflux for 16 hours. Additional bromoethyl nitroimidazole (0.22 g, 1 mmol) was added followed by potassium fluoride on celite (0.3 g, 5 mmol) and stirring with reflux was continued for another 24 hours. Solvent was removed under reduced pressure and the residue was treated with 20 mL of water. The pH of the solution was adjusted with sodium bicarbonate to ≧8. The solution was extracted with dichloromethane (5×20 mL). The combined organic layer was washed with water and dried with anhydrous sodium sulfate. Removal of the solvent gave a semi-solid which was chromatographed over flash silica gel. Elution with 5% methanol in dichloromethane furnished an oil which was homogeneous on TLC. Yield: 0.065 g. $^1$H NMR (CDCl$_3$) δ1.1, 1.3, 1.35 and 1.45 (4s, 12H, gem dimethyls), 2.5–3.2 (m, 10H, N—CH$_2$), 3.9 (bs, 1H, NH), 4.5 (m, 2H, imi CH$_2$), 7.1 (s, 1H, imid H) and 7.4 (s, 1H, imi H). M.S. [M+H]$^+$=374. TLC (9:1, dichloromethane/methanol, silica gel ): R$_f$ 0.38. HPLC: Single peak, R$_t$=10.06 min, with UV detection (230 nm) with a Dynamax C$_{18}$ column, 25 cm×0.46 cm, and gradient elution with acetonitrile and water (containing 0.1% trifluoroacetic acid).

Example 6

[$^{99}$Tc]Oxo[[3,3,9,9-tetramethyl-1-(2-nitro-1H-imidazo-1-yl)-4,8-diazaundecane-2,10-dione dioximato]-(3-)-N,N',N",N"']technetium(V)

NH$_4$$^{99}$TcO$_4$ (26.6 mg, 0.148 moles) was dissolved in saline (4 mL). The title compound from Example 1 (86.4 mg, 0.225 mmoles) was dissolved in saline (10 mL) containing 10 drops 3M hydrochloric acid, and the pH of the solution adjusted to 6.3 with sodium hydroxide solution. The solutions of ligand and pertechnetate were combined. 0.1M Sodium hydrogen carbonate (5 mL) was added and the pH was adjusted to pH 8.5–9.0 with potassium hydroxide. Diethyl ether (60 mL) was added, followed by a dropwise addition of a suspension of stannous tartrate (83.6 mg, 0.313 mmol) in saline (5 mL). The reaction mixture was stirred for 10 minutes. The ether layer was separated and the aqueous layer extracted with several aliquots of ether (until the yellow color of product was no longer observed in the ether layer). The combined ether aliquots (110 mL) were dried over anhydrous sodium sulfate, and reduced to 2 mL by rotary evaporation. The product was purified by silica gel column chromatography, using ether as eluent. Solvent was removed to a volume of ~1 mL, and stored overnight in a –18° C. freezer. Medium orange crystals were obtained. These were separated by filtration, washed with cold ether, and vacuum dried for four hours. Yield: 25.8 mg. $^1$H NMR (CD$_2$Cl$_2$) δ1.39–1.49 (m, 12H, C(CH$_3$)$_2$), 1.73–1.77 (m, 1H, CH), 2.33 (s, 3H, CH$_3$), 2.35–2.41 (m, 1H, CH), 3.34–3.40 (m, 2H, CH$_2$), 3.46–3.51 (m, 2H, CH$_3$), 5.63–5.73 (m, 2H, CH$_2$), 7.09 (s, 1H, imidazole CH), 7.47 (s, 1H, imidazole CH). M.S.: (M+H)$^+$=496, (M—H)$^-$=494.

Analysis calc'd for C$_{16}$H$_{26}$N$_7$O$_5$Tc: C, 38.79; H, 5.29; N, 19.79;

Found: C, 39.21; H, 5.60; N, 19.47.

Example 6a

[$^{99}$Tc]Oxo[[3,3,9,9-tetramethyl-1-(4-nitro-1H-imidazo-1-yl)-4,8-diazaundecane-2,10-dione dioximato ]-(3-)-N,N',N",N"']technetium (V)

To a stirring solution of [N(butyl)$_4$]TcOCl$_4$$^-$ (45.5 mg, 0.091 mmol) (prepared by the method of F. A. Cotton. A. Davison, V. Day et al., *Inorg. Chem.*, 1979, 18, 3024) was added 1 mL of methanol and 120 mL of neat ethylene glycol, followed by 1.2 mL of 0.75M sodium acetate in methanol. Addition of the ligand of Example 2 (namely 3,3,9,9-tetramethyl-1-(4-nitro-1H-imidazo-1-yl)4,8-diazeundecane-2,10-dione dioxime (53.6 mg, 0.14 mmol) caused the purple solution to turn deep yellow orange. After 3 minutes, 10 mL of methylene chloride was added, and the reaction was stripped to an orange oil by rotary evaporation. The complex was purified by passage through a silica gel column that was conditioned and eluted with methylene chloride. The red-orange band was evaporated to an oil, triturated to a solid with 15 mL of hexanes, and the solid was isolated and dried in vacuo overnight to yield 30.3 mg of the title compound. M.S.: (M+H)$^+$=496; (M+H-4-nitroimidazole)$^+$=383; (M—H)$^-$=494. $^1$H NMR (C$_6$D$_6$): δ1.4–1.6 (m, 12H, CH$_3$), 1.75 (m, 1H, CCH$_2$C), 2.4 (m, 1H, CCH$_2$C), 2.34 (s, 3H, CH$_3$C=N), 3.35 (t, 1H, NCH$_2$), 3.5 (m 1H, NCH$_2$), 4.9 (d, 1H, imidazole N CH$_2$, J=14 Hz), 5.3 (d, 1H, imidazole NCH$_2$, J=14 Hz), 7.7 (s, 1H, imidazole NCHC), 8.1 (s, 1H, imidazole NCHC), 18.1 (br, O . . . H . . . O).

Example 6b

[$^{99}$Tc]Oxo[[6-hydroxy-3,3,9,9-tetramethyl-(2-nitro-1H-imidazo-1-yl)-4,8-diazaundecane-2,10-dione dioximato]-(3-)-N,N',N",N"']technetium (V)

To a stirring solution of [N(butyl)$_4$]TcOCl$_4$$^-$ (57.5 mg, 0.115 mmol) was added 1 mL of methanol and 150 µL of neat ethylene glycol, followed by 1.5 mL of 0.75M sodium acetate in methanol. Addition of the ligand of Example 4 (60 mg, 0.13 mmol) caused the purple solution to turn deep yellow-brown. After 5 minutes, the solvent was removed by rotary evaporation to give a yellow-brown oil. The oil was loaded onto a 1.5×6 cm silica gel column that was eluted with methylene chloride until the major product was well separated from impurity bands at the head of the column. The head of the column was removed (and discarded) and the product (as a very broad band) was eluted from the column with 10% methanol/90% methylene chloride. Solvent was removed and the product was redissolved in minimal methylene chloride, washed with saturated sodium chloride, dried over sodium sulfate and rechromatographed using 1:1 ACN:CH$_2$Cl$_2$ as the eluant. Solvent was evaporated to yield an orange oil, which was triturated with hexanes until the product solidified. The solid was isolated by suction filtration, rinsed with hexanes and dried in vacuo overnight. The yield of pure title complex was 8.4 mg. M.S.: (M+H)$^+$=512, (M—H)$^-$=510. IR(KBr): 922 cm$^{-1}$, Tc=O.

Example 7

Preparation of $^{99m}$Tc Complexes

The following general method was used to produce the $^{99m}Tc$ complexes of the ligands given in Examples 1–5.

Ligand (2.5 mg) was dissolved in 0.9% saline (2 mL) and 0.1M sodium hydrogen carbonate buffer (0.5 mL) in a 10 mL glass vial. Eluate from a $^{99}Mo/^{99m}Tc$ generator (0.4 mL) was added. The vial was sealed, and a saturated solution of stannous tartrate in saline (50 µL) was added to the vial. The vial was shaken to mix the reagents, and allowed to stand at room temperature for 10 minutes.

When required, the $^{99m}Tc$ complex was separated from the other kit components by an isolation procedure involving PRP-1 resin (as described by S. Jurisson et al., "Chloro→Hydroxy Substitution on Technetium BATO [TcCl(dioxime)$_3$BR] Complexes", Nuc. Med. Biol, 18(7), 735–744 (1991). This provided the complex in ethanolic solution. The ethanol fraction was blown dryness under nitrogen gas and redissolved in normal saline.

The radiochemical purity of the $^{99m}Tc$ complexes were determined by HPLC and/or TLC. HPLC analyses were conducted on a 5µ 15 cm PRP-1 column with 65/35 ACN/0.1M NH$_4$OAc pH 4.6 as eluent at a flow rate of 1 mL/min., and a radiometric detector connected to an integrator. TLC analyses were conducted on two 20 cm SAF Instant thin layer chromatography (ITLC™) strips. 5 µL samples were applied to the origin of these strips. One strip was developed with saline, and one with methylethyl ketone (MEK). After development, strips were cut 1 cm above the origin, and each section was counted. The % RCP was determined as: %RCP=% on upper segment of MEK strip-% on upper segment on saline strip. The RCP of $^{99m}Tc$ complexes was generally >92%.

Example 7a

[$^{99m}Tc$] Oxo[[3,3,9,9-tetramethyl-1-(2-nitro-1H-imidazo-1-yl)-4,8-diazaundecane-2,10-dione dioximato]-(3-)-N,N', N", N'"]technetium(V) by ligand exchange from $^{99m}Tc$-tartrate.

To 0.5 mL of an 0.1M solution of disodium tartrate in water was added 0.5 mL of physiological saline. The mixture was dispensed into a crimp-sealed vial and purged with nitrogen to remove oxygen. To this was added 5 µL of a freshly prepared solution of stannous chloride (2 mg/mL in degassed 1N HCl), followed by 1 mL of $^{99m}TcO_4^-$ eluted from a $^{99}Mo/^{99m}Tc$ generator. After 10 minutes at room temperature, the resulting Tc-tartrate complex was added to another vial that contained 1.75 mg of the nitroimidazole ligand of Example 1. After 10 minutes at room temperature, the radiochemical purity of the title $^{99m}Tc$ 2-nitroimidazole complex was 92%, as determined by high pressure liquid chromatography conducted on a 10 micron, 15 cm PRP-1 reverse phase column that was eluted with 65/35 acetonitrile/0.1M NH$_4$OAc (pH 4.6) at a flow of 2 mL/minute. The complex thus prepared had a retention time that was identical to that of an authentic sample of the $^{99}Tc$ complex of Example 6.

Example 7b

[$^{99m}Tc$]Oxo[[3,3,9,9-tetramethyl-1-(2-nitro-1H-imidazo-1-yl)-4,8-diazaundecane-2,10-dione dioximato]-(3-)-N,N',N", N'"]technetium(V) by ligand exchange from $^{99m}Tc$-citrate $^{99m}TcO_4^-$ (1 ml, ~30 mCi) in saline was added to a vial containing trisodium citrate (0.05M) in saline (1 ml, pH adjusted to 6.1), 5 µl of stannous chloride solution (2.2 mg/ml) in 0.1M hydrochloric acid was added, and the solution was allowed to stand for 10 minutes to complete the formation of $^{99m}Tc$-citrate. This solution (pH 5.8) was added to a second vial containing 2 mg of the ligand described in Example 1, and the reaction mixture was allowed to react for 20 minutes at room temperature. The final pH was 7.1. The radiochemical purity (determined by HPLC, as described in Example 7A) was >94%, and the radiochemical purity remained at this level for >1 hour.

Example 7c

[$^{99m}Tc$]Oxo[[4,7-Diaza-2,9-dimercapto-2,9-dimethyl-4-(2-(2-nitro-1H-imidazo-1-yl)ethyl)decane]-(3-)-N,N',S,S'] technetium(V)

Dithiothreitol (16.3 mg, 106 µmoles) was added to a solution of 5,8-diaza-1,2-dithia-5-(2-(2-nitro-1H-imidazo-1-yl)ethyl)-3,3,10,10-tetramethylcyclodecane (6.83 mg, 18.3 µmoles, prepared as described in Example 5b) dissolved in 1.0 ml methanol, and the solution was stirred at room temperature for 24 hours. The volume of the reaction solution was reduced under argon to <0.25 ml and 1.25 ml pH 2.9 HBr/saline was added. The aqueous solution was extracted several times with diethyl ether to isolate the dithiol from unreacted disulfide. The ether layers were combined, blown to dryness under argon, and the residue was dissolved in pH 1.6 HBr/saline. This solution was washed with diethyl ether (to remove dithiothreitol), and the pH adjusted with sodium hydroxide to 6.2 to give 4,7-diaza-2,9-dimercapto-2,9-dimethyl-4-(2-(2-nitro-1H-imidazo-1-yl)ethyl)decane, which was used without further purification.

$^{99m}Tc$-glucoheptonate was prepared by adding $^{99m}TcO_4^-$ (0.3 ml, 39.2 mCi) to a solution containing sodium glucoheptonate (0.5 ml of 2.42 mg/ml solution in saline) and sodium acetate (0.5 ml of 0.1M; pH 7.03), followed by stannous chloride (25 µl of 5.51 mg/ml solution, 0.725 µmoles, in 0.1M HCl). After standing at room temperature for 30 minutes, 0.9 mL of this solution was added to a solution of 4,7=diaza-2,9-dimercapto-2,9-dimethyl-4-(2-(2-nitro-1H-imidazo-1-yl)ethyl)decane in saline. The mixture was allowed to stand at ambient temperature for 30 minutes, then heated to 70° C. HPLC analysis indicated two major products, presumed to be syn- and anti-isomeric complexes, as found with other N-substituted-DADT complexes (e.g., L. A. Epps, H. D. Burns, S. Z. Lever, H. W. Goldfarb, H. N. Wagner, "Brain Imaging Agents: Synthesis and Characterization of (N-piperidinyl Hexamethyl Diaminodithiolate) oxo Technetium(V) Complexes", Int. J. Appl. Radiat. Isotop, 1987, 38:661–664; A. Mahmood, W. A. Halpin, K. E. Baidoo, D. A. Sweigart, S. Z. Lever, "Structure of a Neutral N-alkylated Diaminedithiol (dadt) Tc-99(V) Complex Syn [TcO(NEt-tmdadt )]Tc-99", Acta Crystallogr., Sect. C: Cryst. Struct. Common., 1991, 47:254–257).

Example 8

Determination of Reduction Potential

The reduction potentials of misonidazole, $^{99}TcO(PnAO)$, and $^{99}Tc$-hypoxia-localizing tracers were determined by cyclic voltammetry (C.V.) in dimethylformamide. C.V. experiments employed a Princeton Applied Research (P.A.R.) Model 174A Polarographic Analyzer with a Model 303 Static Mercury Drop Electrode and were recorded on a Model RE0074 X-Y Recorder. The reference electrode was Ag/AgNO$_3$ with an acetonitrile filling solution saturated with LiCl. The counter electrode was a platinum wire. Voltammograms at mercury were determined at scan rates of 50, 100, 200, and 500 mV/s.

The solutions used in C.V. studies contained test sample at a concentration of 0.2–0.7 mM and tetrabutylammonium tetrafluoroborate (Bu$_4$NHF$_4$) or tetrabutylammonium hexafluorophosphate (Bu$_4$NPF$_6$) supporting electrolyte at a concentration of 0.1M. The solution was deoxygenated by bubbling solvent-saturated nitrogen or argon through the solution for 15 minutes. Variations in the reference potential were accounted for by determining the C.V. of a Ru(acac)$_3$ standard on a daily basis. All measured potentials were corrected according to an absolute peak reduction potential for Ru(acac)$_3$ of −1.210 V vs. Ag/AgNO$_3$ at Hg. The results are shown in the table below:

| Compound name/<br>Example number | $E_{pc}$(V) | Reduction process |
|---|---|---|
| Metronidazole | −1.62 | reversible |
| Misonidazole | −1.49 | reversible |
| $^{99}$TcO(PnAO) | −2.15 | irreversible |
| Compound from Ex. 1 | −1.52 | reversible |
| Compound from Ex. 6 | −1.49 | reversible |
| and | −1.99 | irreversible |

These results demonstrate that both the ligands of this invention and the technetium complexes thereof are reduced electrochemically at potentials that are similar to that of the bioreducible 2-nitroimidazole compound misonidazole, and are thus expected to undergo bioreduction in vivo. In contrast, electrochemical reduction of the non-nitroimidazole control Tc(V) Oxo 3,3,9,9-tetramethyl-4-8-diazaundecane-2,10-dione-dioxime (TcO(PnAO) prepared by the method of Jurisson et al., *Inorg. Chem.*, 1986, 25, 543) occurred at a potential that was far more negative than that of the first reduction wave observed for the compound of Example 6.

Example 8a

Demonstration of Efficacy: Reduction of the Tc Nitroimidazole Complexes by Xanthine Oxidase The enzyme xanthine oxidase (in the presence of xanthine or hypoxanthine) is known to reduce the nitro group of such nitroimidazole-containing compounds as misonidazole and metronidazole (see for example P. D. Josephy, B. Palcic and L. D. Skarsgard, "Reduction of Misonidazole and its Derivatives by Xanthine Oxidase", *Biochem. Pharmacol.*, 1981, 30, 849), and it has been postulated that such nitro reduction under anaerobic conditions is responsible for the selective trapping of these compounds in hypoxic tissue. Thus, a technetium or rhenium containing nitroimidazole complex should be capable of being reduced by xanthine oxidase under anaerobic conditions in the presence of hypoxanthine. The results from the enzyme assay below demonstrate that the Tc-nitroimidazole complexes of this invention are recognized as suitable substrates by xanthine oxidase.

To a 2.5 mL quartz cuvette was added 0.25 micromoles of the $^{99}$Tc-nitroimidazole complex of Example 6 or 6b in 125 μL of dimethylformamide, 1 mL of 0.01M hypoxanthine in pH 7.4 sodium phosphate buffer (0.1M), and 0.875 mL of 0.1M sodium phosphate buffer (pH 7.4) that contained 20 mg/L of disodium ethylenediamine tetraacetic acid (EDTA). The cuvette was sealed with a rubber septum, and purged with argon for 15 minutes to remove oxygen. To this was added 1.25 units of the enzyme xanthine oxidase (Boeringer) in 0.5 mL of deoxygenated pH 7.4 phosphate buffer. The cuvette was inverted to mix, and the UV/visible spectrum of the solution was recorded from 280 to 600 nm at 15 minute intervals.

The absorbance peak at approximately 320 nm, which is characteristic of the nitroimidazole functionality, decreased in intensity. It is believed that the disappearance of this nitro absorbance is due to reduction of the nitro group by xanthine oxidase. In a control reaction that contained no enzyme, no spectral changes were observed over a period of 7 hours.

In a parallel control reaction, the reagents above were mixed in the same fashion, but the $^{99}$Tc complex of 3,3,9,9-tetramethyl-4,8-diazaundecane-2,10-dione dioxime (prepared by the method of Jurisson et al., *Inorg. Chem.*, 1986, 25, 543) was substituted for the technetium complexes of Examples 6 or 6b. In this reaction, which did not contain a bioreducible nitroimidazole functionality, no spectral changes were observed over a period of 7 hours.

Example 9

Demonstration of the Ability to Cross Endothelial Monolayers

Bovine brain microvessel endothelial cells were isolated using a modification of the Audus-Borchardt method (K. L. Audus et al., *Ann. New York Acad. Sci.*, 1988; 9–18). The measurements of bovine brain microvessel endothelial permeability in vitro were adapted from models by Audus and Borchardt (K. L. Audus et al., *J. Neurochem.*, 1986; 47:484–488 and M. V. Shah et al., *Pharm. Res.* 1989; 6:624–627) and W. M. Pardridge et al. (*J. Pharmacol. Exptl. Therap.*, 1990; 253:884–891) except that Anocell inserts were used in place of Transwells containing polycarbonate filters, or polycarbonate filters placed into a side-by-side apparatus. The use of electrical resistance as an indication of tight junction formation (P. Artursson et al., *J. Pharm. Sci.*, 1990; 79:595–600 and S. G. Milton et al., *J. Cell. Physiol.*, 1990; 144:498–504) was applied by using the Millicell-ERS resistance system from Millipore. An asymptotic level of high electrical resistance (~600 Ohms-cm$^2$) at morphological confluence indicated tight junction formation. Only those wells with resistance $\geq$500 Ohms-cm$^2$ were used. Further modifications of the Audus-Borchardt method were the use of DMEM/F-12 media with 10% plasma derived horse serum as the experimental medium inside the Anocell insert and in the outer well.

A study of the permeability of a single test compound utilized 12 Anocell inserts:

4 wells containing monolayers, 0.4 mL of media with 10% plasma-derived horse serum, 5 μCi of $^3$H-water, 2 μCi of $^{14}$C-sucrose, and 20 μCi of the Tc-99m complex;

4 wells containing the same as above, but without the monolayers;

and 4 wells containing the same but with neither monolayers nor the 10% plasma-derived horse serum.

This system was placed into a 37° C., 5% CO$_2$ incubator which contains an orbiting tissue culture plate shaker for agitation and 10 μL samples, from both inside (donor) and outside (acceptor) compartments, were taken simultaneously from a set of 4 Anocell inserts. These samples were counted first in a Gamma counter then, after 72 hours, in a scintillation counter with dual channel capabilities. The fraction of radio activity transported from the donor to the acceptor wells at each time point over the first 10 minutes of the study was calculated. The average percent of radioactivity transported was plotted vs. time and the slope was estimated by linear regression analysis. The slope of the clearance curve with filter alone is equal to PS$_f$, where PS=permeability surface area product. The slope of The clearance curve of the wells containing the filter plus endothelial cells was denoted PS$_m$. The slope of the clearance curve was linear up to 10 minutes for all agents tested. The corrected PS value for The endothelial monolayer, called $PS_e$, was computed as follows (according to Pardridge et al., *J. Pharmacol. Exptl. Therap.*, 1990, 253, 884–891):

$$\frac{1}{PS_e} = \frac{1}{PS_m} - \frac{1}{PS_f}$$

The permeability index ($P_i$) is calculated using the $PS_e$ for each agent as follows:

$$P_i = \left( \frac{PS_{(agent)} - PS_{(sucrose)}}{PS_{(water)} - PS_{(sucrose)}} \right) \times 100$$

The following table provides The determined $P_i$ values for several of the compounds examined:

| Compound name/Example number | $P_i$ |
|---|---|
| $^{99m}$Tc-PnAO (1) | 64.4 |
| $^{99m}$Tc-HM-BAT (2) | 44.3 |
| $^{99m}$Tc-TMR (3) | 50.3 |
| $^{99m}$TcCl(DMG)$_3$2MP (4) | −9.3 |
| $^{99m}$Tc complex from ligand in Ex. 1 | 63.2 |
| $^{99m}$Tc complex from ligand in Ex. 5 | 0.2 |
| $^{99m}$Tc complex from ligand in Ex. 2 | 15.2 |
| $^{99m}$Tc complex from ligand in Ex. 4 | 1.8 |
| $^{99m}$TcCl(DMG)$_3$BBNO$_2$ (5) | 4.5 |

(1) W. A. Volkert, T. J. Hoffman, S. M. Seger, D. E. Troutner, R. A. Holmes, "Tc-99m Propylene Amine Oxime (Tc-99m PnAO); A Potential Brain Radiopharmaceutical", Eur. J. Nucl. Med. 1984, 9:511–516.
(2) H. F. Kung, M. Molnar, J. Billings, R. Wicks, M. Blau, "Synthesis and Biodistribution of Neutral Lipid-Soluble Tc-99m Complexes that Cross the Blood-Brain-Barrier", J. Nucl. Med., 1984, 25:326–332.
(3) R. H. Mach, H. F. Kung, Y-Z, Guc, C-C Yu, V. Subramanyam, J. C. Calabrese, "Synthesis, Characterization and Biodistribution of Neutral and Lipid-Soluble $^{99m}$Tc-PAT-HM and $^{99m}$Tc-TMR for Brain Imaging", Nucl. Med. Biol., 1989, 16:829–837.
(4) E. N. Treher, L. C. Francesconi, J. Z. Gougoutas, M. F. Malley, A. D. Nunn, "Monocapped Tris(dioxime) Complexes of Technetium(III): Synthesis and Structural Characterization of TcX(dioxime)$_3$B-R (X = Cl, Br; dioxime = dimethylglyoxime, cyclohexanedione dioxime; R = CH$_3$, C$_4$H$_9$), Inorg. Chem., 1989, 28:3411–3416.
(5) K. E. Linder, S. Jurisson, A. D. Nunn, "Boronic Acid Adducts of Technetium-99m Dioxime Complexes and Rhenium Dioxime Complexes Containing a Biochemically Active Group, European Patent No. 411,491; 1991.

Example 9a

The Biodistribution of $^{99m}$Tc-Complexes in Normal (Normoxic) Sprague-Dawley Rats The biodistribution of $^{99m}$Tc-complexes was determined to demonstrate delivery of the radiotracers to the target organs, and the clearance of radioactivity from normoxic tissue in the target area and nearby tissues.

Twelve Sprague-Dawley rats were anesthetized with Nembutal (50 mg/kg) and injected with 0.1 mL (20 µCi) of radioactivity via the jugular vein. At 1 minute, 5 minutes and 60 minutes after administration of the radiotracers (n=4 for all time points), the animals were sacrificed by exsanguination, and the target tissues removed, weighed and assayed for radioactivity. The rats were allowed to respire room air throughout the course of the study.

The results are shown in the following tables:

TABLE 1

Percent ID/g for the $^{99m}$Tc-complex of the ligand in Example 1

| | 1 Min. | | 5 Min. | | 60 Min. | |
|---|---|---|---|---|---|---|
| Tissue | MEAN | SEM | MEAN | SEM | MEAN | SEM |
| Brain | 0.30 | 0.03 | 0.11 | 0.01 | 0.02 | 0.00 |
| Blood | 0.47 | 0.06 | 0.36 | 0.01 | 0.28 | 0.02 |
| Heart | 1.32 | 0.19 | 0.34 | 0.03 | 0.09 | 0.01 |
| Lungs | 0.71 | 0.09 | 0.39 | 0.03 | 0.16 | 0.01 |
| Kidneys | 2.59 | 0.27 | 1.15 | 0.12 | 0.45 | 0.04 |
| Liver | 2.06 | 0.25 | 3.63 | 0.18 | 2.45 | 0.18 |
| Muscle | 0.25 | 0.07 | 0.14 | 0.02 | 0.05 | 0.02 |
| Bone | 0.37 | 0.02 | 0.23 | 0.01 | 0.11 | 0.05 |
| Stomach | 0.67 | 0.10 | 0.56 | 0.03 | 1.80 | 0.34 |
| Thyroid | 0.65 | 0.10 | 0.77 | 0.28 | 0.15 | 0.02 |
| Thymus | 0.55 | 0.06 | 0.25 | 0.06 | 0.05 | 0.00 |
| Upper Intestine | 1.13 | 0.05 | 0.98 | 0.09 | 4.60 | 0.22 |
| Lower Intestine | 0.50 | 0.06 | 0.40 | 0.03 | 0.36 | 0.04 |
| Bladder | 0.15 | 0.02 | 0.68 | 0.12 | 2.84 | 0.41 |
| Spleen | 0.84 | 0.02 | 0.45 | 0.02 | 0.23 | 0.03 |

(SEM = standard error of the mean)

TABLE 2

Percent ID/g for the $^{99m}$Tc-complex of the ligand in Example 4

| | 1 Min. | | 5 Min. | | 60 Min. | |
|---|---|---|---|---|---|---|
| Tissue | MEAN | SEM | MEAN | SEM | MEAN | SEM |
| Brain | 0.03 | 0.00 | 0.01 | 0.00 | 0.00 | 0.00 |
| Blood | 0.62 | 0.07 | 0.29 | 0.01 | 0.09 | 0.01 |
| Heart | 1.02 | 0.08 | 0.22 | 0.01 | 0.05 | 0.00 |
| Lungs | 0.63 | 0.03 | 0.25 | 0.01 | 0.05 | 0.01 |
| Kidneys | 2.53 | 0.22 | 0.94 | 0.04 | 0.70 | 0.04 |
| Liver | 2.19 | 0.14 | 2.69 | 0.19 | 1.09 | 0.05 |
| Muscle | 0.19 | 0.05 | 0.16 | 0.02 | 0.04 | 0.00 |
| Bone | 0.34 | 0.00 | 0.16 | 0.01 | 0.03 | 0.00 |
| Stomach | 0.30 | 0.06 | 0.25 | 0.04 | 0.23 | 0.03 |
| Thyroid | 0.61 | 0.05 | 0.37 | 0.02 | 0.08 | 0.01 |
| Thymus | 7.01 | 0.26 | 0.20 | 0.01 | 0.04 | 0.00 |
| Upper Intestine | 0.72 | 0.06 | 1.18 | 0.21 | 5.36 | 0.14 |
| Lower Intestine | 0.29 | 0.04 | 0.45 | 0.16 | 0.39 | 0.01 |
| Bladder | 0.09 | 0.03 | 2.59 | 0.75 | 6.40 | 1.12 |
| Spleen | 0.94 | 0.10 | 0.41 | 0.02 | 0.09 | 0.02 |

(SEM = standard error of the mean)

Example 10

Demonstration of Efficacy in a Rabbit Focal Myocardial Ischemia Model

A model of focal myocardial ischemia in the rabbit was developed, using permanent ligation of the left anterior descending (LAD) coronary artery. The model consisted of two studies. In the first, relative regional myocardial blood flow (MBF) and relative regional myocardial rate of glucose metabolism (MMR$_{gl}$) were determined by autoradiography using a double-label study with the flow tracer $^{99m}$TcCl (CDO)$_3$MeB (R. K. Narra et al., *J. Nucl. Med.*, 1989; 30:1830–1837) and $^{14}$C-deoxy glucose for MMR$_{gl}$ (L. Sokoloff et al., *J. Neuro-chem.*, 1977, 28, 897–916). $^{14}$C-deoxyglucose and the $^{99m}$Tc-hypoxia-localizing tracer were administered to a second group of rabbits with LAD coronary artery occlusion.

After the surgical preparation and 20 minutes of LAD occlusion, $^{14}$C-deoxyglucose (130–150 µCi) was injected as an intravenous bolus, and timed arterial blood samples were obtained. Twenty-five minutes later, $^{99m}$TcCl(CDO)$_3$MeB (10–12 mCi) was administered intravenously. Five minutes later, the rabbits were sacrificed by intravenous injection of Nembutal and potassium chloride. The heart was excised, frozen in liquid Freon-22, and 20 µm coronal sections obtained with a Microtome. Autoradiographs were obtained on all sections. For the first exposure (~14 hours duration) of Kodak XAR film, extra heavy duty aluminum foil was interposed between the tissue and film to block completely the radiation emanating from $^{14}$C to obtain the MBF information derived from $^{99m}$TcCl-(CDO)$_3$MeB alone. After three days (to allow for decay of $^{99m}$Tc), a second autoradiograph was obtained without foil. The second exposure lasted 6–8 days, and provided an image of the regional distribution of $^{14}$C-deoxyglucose. These images established that there is a zone of increased glycolysis bordering on the ischemic territory. This region of increased glycolysis, induced by reduced tissue pO$_2$, marks the hypoxic ischemic border zone.

In a second group of animals, the protocol was similar, except that the $^{99m}$Tc complex of the ligand described in Example 1 was co-injected with $^{14}$C-deoxyglucose, and the animal sacrificed 30 minutes later.

Autoradiography revealed an isomorphic relationship between the regional myocardial distribution pattern of this complex and that for $^{14}$C-deoxyglucose. Both tracers displayed high uptake in the ischemic border zone, with low levels of radioactivity in the regions of normal perfusion, and virtually no radioactivity in the region of no flow. The microregional distribution of both the tracers was virtually identical. By comparison, the ischemic zone in the study with the $^{99m}$Tc-flow tracer showed little accumulation of radioactivity, while regions of normal perfusion displayed high levels of radioactivity.

The $^{99m}$Tc-complex of 3,3,6,9,9-pentamethyl-4,8-diazaundecane-2,10-dione dioxime was examined in this model as an example of a $^{99m}$Tc-PnAO-complex which does not possess a hypoxia-localizing functionality. The autoradiograms obtained with this tracer showed no differentiation of ischemic and non-ischemic regions indicating that a hypoxia localizing moiety such as 2-nitroimidazole is essential for specific localization of these complexes within hypoxic regions.

In a separate experiment using the rabbit LAD occlusion model and the double-label auto radiography procedures described above, the performance of the $^{99m}$Tc complex of the ligand described in Example 1 was compared to that of $^{14}$C-misonidazole. The microregional distribution of both agents was virtually identical and was similar to that found previously for $^{14}$C-deoxyglucose: high uptake in the hypoxic border zone of the ischemic territory and low uptake in normoxic regions and in the center of the ischemic territory where flow is limiting.

Example 10a

Demonstration of Efficacy in a Rat Focal Cerebral Ischemia Model

A model of focal cerebral ischemia involving tandem occlusion of the internal carotid artery and the ipsilateral middle cerebral artery (MCA) in spontaneously hypertensive rats (SHR) was characterized using the double-label autoradiography procedure described in Example 10. In this case, $^{99m}$TcCl(DMG)$_3$2MP (Narra et al., *J. Nucl. Med.*, 1990, 31(8), 1370–1377) was used as the indicator for cerebral blood flow (CBF) and, as before, $^{14}$C-deoxyglucose was used to demonstrate areas of increased glycolysis indicative of tissue hypoxia. Following surgery, which was performed under Halothane anesthesia, the rats were allowed to recover and one hour after the MCA occlusion, $^{14}$C-deoxyglucose was injected as an IV bolus and timed arterial samples were obtained. Twenty-five minutes after $^{14}$C-deoxyglucose injection, $^{99m}$TcCl(DMG)$_3$2MP was injected as an IV bolus and the rat was sacrificed 15 seconds later. The brain was rapidly removed and sections and autoradiograms were obtained as described in Example 10. As found in Example 10 for the rabbit LAD occlusion model, the ischemic territory was bordered by a rim of tissue in which glycolysis was elevated. Unlike the previously cited example of myocardial ischemia, the hypoxic region in the brain did not have as great an increase in glycolysis compared to normoxic regions because the brain uses glucose as the preferred substrate for oxidation in normoxic tissue. Nevertheless, it was clear that the ischemic region is surrounded by a border zone of increased glycolysis. In a second series of experiments, the $^{99m}$Tc complex of the ligand described in Example 1 and $^{14}$C-deoxyglucose were co-injected 1 hour or five days after MCA occlusion. Autoradiograms were obtained as described above and revealed, for both time points, that both agents displayed an increased uptake in the hypoxic border zone relative to surrounding normoxic tissue. Moreover computer assisted image analysis showed that, in the case of $^{99m}$Tc complex of the ligand described in Example 1, the hypoxic-normoxic optical density ratio was 7:1. These findings demonstrate the efficacy of the $^{99m}$Tc complex of the ligand described in Example 1 for both acute and chronic episodes of focal cerebral ischemia.

Example 11

Demonstration of Efficacy: Isolated Perfused Heart Studies

Hearts were excised from male Sprague Dawley rats (275–325 g) and were perfused retrogradely using the Langendorff method (O. Langendorff, *Pfleugers Arch. ges. Physiol*, 61, 291, 1985) with modifications described previously (W. Rumsey, D. F. Wilson and M. Erecinska, *Am. J. Physiol.*, 253 (Heart Circ. Physiol. 22): H1098, 1987) in the isolated state at 37° C. with Krebs-Henseleit buffer. The perfusate contained [in mM] NaCl [118], KCl [4.7], CaCl$_2$ [1.8], Na$_2$EDTA [0.5], KH$_2$PO$_4$ [1.2], MgSO$_4$ [1.2], NaHCO$_3$ [25], glucose [11], pyruvate [0.2], and insulin (12 IU/L) and was equilibrated with O$_2$:CO$_2$ (95:5) (global normoxia) or N$_2$:CO$_2$ (95:5) (global hypoxia). The hearts were paced continuously at 5 Hz. Perfusion pressure was maintained at 72 cm H$_2$O for 20 minutes in order to allow the hearts to adjust to the isolated state. After this initial adjustment period, perfusate flow was maintained constant a level similar to that obtained at the end of the adjustment period, i.e., 7–8 mL/min/g wet weight, using a peristaltic pump.

For determination of oxygen consumption, a cannula was placed in the right ventricle via the pulmonary artery. A pump removed a small fraction of the coronary effluent at 1 mL/min., and its oxygen concentration was monitored continuously by an in-line Clark-type electrode. In the normoxic state, the influent oxygen concentration was maintained at 956 µM. Coronary flow was measured by collecting the effluent from the right and left pulmonary arteries in a 10 mL graduated cylinder. Oxygen consumption was calculated from the product of the influent-effluent oxygen concentration difference and the coronary flow. During perfusion with hypoxic medium, only the effluent oxygen concentration was recorded. Typically, effluent oxygen concentration was 505 µM in the normoxic studies and 17 µM in the hypoxic studies.

The heart was perfused with either normoxic or hypoxic medium for 30 minutes prior to the administration of the test compound. The Tc-99m tracer was administered over 20 minutes by infusion into the perfusate, and radioactivity in the perfused heart was detected by a collimated crystal positioned 3–4 cm from the right ventricle and perpendicular to the vertical axis of the heart. The radioactivity remaining in the heart at 40 minutes after the end of the infusion period was divided by the peak level of radioactivity to give a measure of retention. Results (n=4) are shown in the table, below:

| % Retention of Tracer in the Isolated Perfused Rat Heart | Normoxia | Hypoxia |
| --- | --- | --- |
| Tc-99m complex of ligand in Ex. 1 | 33.5 ± 2.5 | 65.3 ± 3 |
| [Tc-99m]TcCl(CDO)$_3$MeB** | 71.3 ± 5.5* | 63.3 ± 3.7 |
| [Tc-99m]TcCl(DMG)$_3$2MP** | 68.5 ± 0.5 | 48.7 ± 1.3 |

*n = 3
**Prior Art Boronic Acid Adducts (U.S. Pat. No. 4,705,849)

The Tc-99m complex of ligand 1 demonstrates greater retention in the hypoxic heart, compared to the normoxic heart. By comparison, the flow tracers TcCl(DMG)$_3$2MP and TcCl(CDO)$_3$MeB do show an increase in retention under hypoxic conditions compared to normoxia.

Example 12

Demonstration of Efficacy: Isolated Cardiac Myocyte studies

Calcium-tolerant ventricular myocytes were isolated from hearts of male Sprague Dawley rats (200 g) according to the procedure of Wittenberg and Robinson (B. A. Wittenberg and T. F. Robinson, *Cell Tissue Res.*, 216: 231, 1981) with modifications described previously (W. Rumsey, C. Schlosser, E. M. Nuutinen, M. Robiolio and D. F. Wilson, *J. Biol. Chem.*, 265 (26): 15392, 1990). Cells were used immediately following morphological analysis (using a hemocytometer) of viability and were maintained at 37° C. during the experiments. The number of quiescent, rod shaped cells ranged from 70–90% within a total population of 5–9×10$^6$ cells.

The isolated myocytes were maintained in either a normoxic, hypoxic or anoxic state. Hypoxia was induced by providing an atmosphere of argon atop of the cells and sealing the flask during the incubation period. Glucose oxidase plus catalase (5/5 mg) was added to argon treated cells to provide anoxia. Cells were suspended (6.5–7.5×10$^4$ cells/ml) in isolation media and aliquots were added to incubation vials maintained at 37° C.

After incubation with a test compound, myocytes were deproteinated with 1% ice-cold perchloric acid and centrifuged at 12,000 rpm for 30 sec. The supernatent was separated from the pellet and each counted using a LKB 1282 gamma counter. Alternatively, myocytes were separated from the suspending media by passing the cells through 99% dibutyl phthalate by centrifugation at 12,000 rpm for 30 sec. The three phases were separated and counted as described above. Results for the Tc-99m complex of the compound in Example 1 are given below:

| Condition | PCA Pellet | Cell Pellet | Oil |
| --- | --- | --- | --- |
| Normoxia (n = 5) | 40.5 ± 2.7 | 23.2 ± 3.7 | 22.8 ± 2.2 |
| Hypoxia (Argon) (n = 4) | 48.5 ± 3.4 | 36.9 ± 8.8 | 20.1 ± 5.3 |
| Anoxia (Glucose Oxidase) (n = 4) | 55.5 ± 5.8 | 48.8 ± 4.2 | 9.0 ± 2.6 |

Values represent means ± S.E.M. for the number of experiments noted in the parentheses. The values are the percent of total radioactivity represented by each case. PCA pellet= perchloric acid precipitated pellet which represents the activity associated with proteins/membranes. Cell pellet= whole cells passed through a layer of dibutyl phthalate (oil).

These data demonstrate that the Tc-99m complex of the compound in Example 1 shows retention in the sequence anoxia>hypoxia>normoxia. Since a significant proportion of tracer was retained in normoxic myocytes, a separate study with isolated myocytes was undertaken.

Addition of an uncoupler of β-oxidative phosphorylation, carbonyl cyanide p-trifluoro methoxyphenylhydrazone (FCCP), which completely oxidizes the mitochondrial electron transport chain (NADH/AND$^+$ ratio and the redox potential of the cells decrease) but decreases the phosphorylation potential ([ATP]/[ADP][Pi]) to levels similar to that found in hypoxia, had no effect on the retention of the Tc-99m complex of the compound in Example 1 in normoxic cells. Moreover, addition of cyanide to separate cell suspensions (n=3), which inhibits electron transport between cytochrome oxidase and oxygen (NADH/NAD$^+$ ratio and redox potential increase) but also decreases the phosphorylation potential to very low levels, had no effect on retention in normoxic cells. These results suggest that:

1) retention of the Tc-99m complex of the compound in Example 1 in normoxic cells is not dependent on the redox state of the intramitochondrial pyridine nucleotides and is most likely due to its lipophilicity or other molecular interactions affecting binding to cellular material. If the amount retained in normoxic cells was dependent upon the redox state, retention would have been expected to decrease upon addition of FCCP.

2) Significant retention of the Tc-99m complex of the compound in Example 1 requires an oxygen-free or low oxygen milled. An increase in the redox potential (cyanide) is not sufficient to affect the level of retention. The latter results were confirmed using Na Amobarbital which also inhibits electron flux but at site I of the respiratory chain (NADH/NAD$^+$ ratio increases).

3) Most importantly, by uncoupling the cells and by addition of cyanide, the energy state of the cells was reduced to levels that were likely similar to that obtained with oxygen 30 deprivation. Thus, any changes in cellular permeability, geometry and viability were also similar, suggesting that retention was due to reduction of the nitro moiety of the Tc-99m complex of the compound in Example 1 in the absence of oxygen. These data indicate that, in hypoxia, the Tc-99m complex of the compound in Example 1 becomes trapped within the hypoxic cells.

When cellular integrity was disrupted by freezing and thawing the cells (3×) before incubation with the Tc-99m complex of the compound in Example 1 under normoxic and hypoxic (glucose oxidase) conditions, the percentage of activity associated with the protein/membrane fragments was similar (normoxic=23.3±0.8%, anoxic=25.3±2.5%, n=3). The latter indicates that an intact cell is required for trapping of the compound.

Several Tc-99m complexes were examined in isolated myocytes using the protocol described above. The percentage of activity retained in the cell pellet was determined under anoxic and normoxic states. Results are shown below:

| | % in Cell Pellet | |
|---|---|---|
| | 99mTc Complex of Compound in Ex. 1 | 99mTc Complex of Compound in Ex. 2 |
| Normoxia | 24.1 ± 2.3 | 23.5 ± 1.7 |
| Anoxia | 53.0 ± 2.2 | 39.9 ± 0.5 |
| Anoxia/normoxia ratio | 2.3 | 1.7 |
| | 99mTc Complex of Compound in Ex. 4 | 99mTc Complex of Compound in Ex. 5 |
| Normoxia | 10.9 ± 0.8 | 10.0 (n = 1) |
| Anoxia | 48.6 ± 9.8 | 18.2 (n = 1) |
| anoxia/normoxia ratio | 4.4 | 1.8 |
| | 99mTc Complex of 6-methyl-PnAO | 99mTc Complex of 6-hydroxy-PnAO |
| Normoxia | 17.4 (n = 1) | 7.1 (n = 1) |
| Anoxia | 22.7 (n = 1) | 9.2 (n = 1) |
| anoxia/normoxia ratio | 1.3 | 1.3 |
| | 99mTc Complex of TcCl(CDO)$_3$MeB | 99mTc Complex of TcCl(DMG)$_3$2MP |
| Normoxia | 73.6 (n = 2) | 69.5 (n = 2) |
| Anoxia | 83.5 (n = 2) | 80.0 (n = 2) |
| anoxia/normoxia ratio | 1.1 | 1.2 |

The $^{99m}$Tc-complexes of 6-methyl PnAO (3,3,6,9,9-pentamethyl-4,8-diazaundecane-2,10-dione dioxime) and 6-hydroxy PnAO(6-hydroxy 3,3,9,9-tetramethyl-4,8-diazaundecane-2,10-dione dioxime) and the $^{99m}$Tc-complexes TcCl(CDO)$_3$MeB and TcCl(DMG)$_3$2MP (U.S. Pat. No. 4,705,849) are representative neutral, lipophilic complexes which do not contain a hypoxia-localizing moiety. These data demonstrate greater anoxia/normoxia ratios for the hypoxia-localizing compounds of this disclosure than the complexes without a hypoxia localizing moiety.

In a separate study, the uptake of the $^{99}$Tc complex of the ligand of Example 1 in isolated myocytes under normoxia, hypoxia and anoxia was compared to $^3$H-FMISO and $^{125}$I-iodovinyl MISO. The anoxia/normoxia and hypoxia/normoxia ratios indicate that the $^{99m}$Tc complex of the compound in Example 1 shows similar selective retention in anoxic cells to the hypoxia-localizing compounds labeled with $^3$H and $^{125}$I described in the literature.

| | 99mTc Complex of ligand in Ex. 1 | $^3$H-FMISO | $^{125}$I-iodovinyl MISO |
|---|---|---|---|
| Normoxia | 18 ± 1 (3) | 3 ± 1 (3) | 12 ± 1 (3) |
| Hypoxia | 30 ± 7 (3) | 5 ± 1 (3) | 16 ± 3 (2) |
| Anoxia | 48 ± 6 (3) | 8 ± 2 (3) | 24 ± 3 (3) |
| Hypoxia/normoxia | 1.7 | 1.7 | 1.4 |
| Anoxia/normoxia | 2.7 | 2.7 | 2.0 |

Example 13

Demonstration of Efficacy: Studies in Isolated Mitochondria

Mitochondria were prepared from hearts of male Sprague Dawley rats (200 g) using the isolation procedure of Fuller et al., (E. O. Fuller, D. I. Golderg, J. W. Starnes, M. Sacks, and M. J. Delavoria-Papadopoulos, *Mol. Cell. Cardiol.,* 17:71, 1985). The heart was excised from anesthetized rats and trimmed free of the atria and great vessels. The ventricles were minced in ice-cold isolation medium (0.225M mannitol, 75 mM sucrose, 1.0 mM EGTA and 10 mM MOPS, pH 7.4), briefly exposed to the proteolytic enzyme preparation, Nagase (Enzyme Development Corp., New York, N.Y.), and homogenized with a polytron. The mitochondria were separated from the remainder of the broken cells using density gradient centrifugation.

Three nitroimidazole compounds were incubated at 37° C. for 60 minutes in isolated mitochodria. Hypoxia and anoxia were induced as outlined in Example 12. The percentage of radioactivity associated with the mitochondria are shown in the following table:

| | 99mTc Complex of Ligand in Ex. 1 | 99mTc Complex of Ligand in Ex. 4 |
|---|---|---|
| Normoxia | 27.8 ± 1.2 | 15.7 ± 0.4 |
| Hypoxia | 39.2 ± 1.0 | 47.7 ± 3.7 |
| Hypoxia/Normoxia | 1.4 ± 0.1 | 3.1 ± 0.3 |

Values are given in percent of total radioactivity within an aliquot and represent means ±S.E.M. Compounds were tested using the same preparation of mitochondria.

These data indicate that mitochondria may have a role in the selective retention of these radiotracers under hypoxic and normoxic conditions.

Example 14

Synthesis of 3,3,6,6,9,9-Hexamethyl-1-(2-nitro-1H-imidazo-1-yl)-4,8-diazaundecane-2,10-dione dioxime A. N-(3-Amino-2,2-dimethylpropyl)-1-amino-1,1-dimethyl-2-butanone oxime To a solution of 2,2-dimethyl-1,3-propane diamine (69 g. 0.75 mole) in dry methanol (100 ml), 3-chloro-3-methyl-2-nitrosobutane (20.55 g, 0.15 mole, Example 1) was added in portions at 0° C. over a period of 2 hours. The reaction mixture was then stirred at room temperature for 20 hours. The solvent was removed under reduced pressure to give a paste. Water (50 mL) was added, and the solution was cooled in an ice bath. The solution was filtered and the filtrate was adjusted to pH 10–11 by the addition of sodium hydroxide. The solution was cooled again and filtered. The filtrate was concentrated under reduced pressure to a paste and then extracted with ether repeatedly (10×50 mL). The combined ether solution was concentrated to give an oil which was recrystallized twice from petroleum ether to yield the title A compound as a colorless crystalline solid (20.0 g), m.p. 58°–60° C. $^1$H NMR [CDCl$_3$]: δ 0.85 (s, 6H, C—Me$_2$), 1.28 (s, 6H, N—CMe$_2$), 1.9 (s, 3H, N=CMe), 2.3 (s, 2H, NCH$_2$) and 2.6 (s, 2H, N—CH$_2$).

B. 3,3,6,6,9,9-Hexamethyl-1-(2-nitro-1H-imidazo-1-yl)-4, 8-diazaundecane-2,10-dione dioxime A solution of the the title A compound (0.8 g, 4 mmol) was treated with diisopropylethylamine (0.39 g, 3 mmol) in dichloromethane (5 mL) and stirred. 3-Chloro-3-methyl-1-(2-nitro-1H-imidazo-1-yl)-2 -nitrosobutane (0.783 g, 3 mmol, Example 1(B)) was added and the reaction mixture was stirred at room temperature for 48 hours. All volatile material was removed under reduced pressure, and the resultant paste was dissolved dichloromethane (2 mL). This solution was loaded onto a flash silica gel column. The column was slowly eluted with 0–5% methanol in dichloro methane until all of the product had eluted. The crude product was purified by chromatography twice more to give a pale yellow product with ~97% purity by HPLC analysis. The product was dried under vacuum at room temperature for 24 hours to give 0.12 g of the title compound, m.p:—the solid becomes a glass at 80°–83° C. and melts at 118°–120° C. with decomposition.

$^1$H NMR [CDCl$_3$]: δ0.8 (s, 6H, CMe$_2$), 1.2 (s, 12 H, N—CMe$_2$), 1.9 (s, 3H, N=CMe), 2.2 (2s d, 4H, N—CH$_2$), 5.4 (s, 2H, imidazole CH$_2$), 7.1 (s, 1H, imidH) and 7.15 (s, 1H, imidH). M.S. [M+H]$^+$412. Analysis calc'd for C$_{18}$H$_{33}$N$_7$O$_4$ . 0.6 THF and 0.1 H$_2$O: C, 53.73; H, 8.39; N, 21.50; Found: C, 53.73; H, 8.55; N, 21.28.

Example 15

Synthesis of 6,6-Diethyl-3,3,9,9-tetramethyl-1-(2-nitro-1H-imidazo-1-yl)-4,8-diazaundecane-2,10-dione dioxime A. N-(2-Aminomethyl-2-ethylbutyl)-1-amino-1,1-dimethyl-2-butanone oxime 3-Chloro-3-methyl-2-nitrosobutane (4.59 g, 0.034 mol) was added portionwise to a cooled (0° C.) solution of 5,5-diethyl-1,3-diaminopropane (8.86 g, 0.068 mol) in methanol (40 mL). After the addition, the reaction mixture was allowed to warm to room temperature and stirred for 48 hours. Methanol was removed on a rotary evaporator. The residue was dissolved in dioxane-water (2:1, 300 mL) and the solution was cooled to 0° C. Sodium carbonate (15.9 g, 0.15 mol) was added to this mixture followed by di-t-butyl dicarbonate (32.73 g, 0.15 mol). The reaction mixture was stirred at 0° C. for 2 hours and at room temperature for 12 hours. Dioxane and water were removed on a rotary evaporator and the residue was poured into water and extracted with ether. The ether solution was washed with water and dried with sodium sulfate. Ether was removed on a rotary evaporator and the residue was chromatographed over silica gel (hexane-ethyl acetate, 7:3). Di-t-Boc-5,5-diethyl-1,3-diamino propane eluted in the earlier fractions. The fractions containing the Boc derivative of the product were collected and the solvent was evaporated to yield a thick oil which solidified on standing (4.2 g). This was treated with methanolic HCl (25 mL) at room temperature for 30 minutes. Methanol was removed under reduced pressure and the solid obtained was neutralized with methanolic ammonia to yield the title A compound as a white solid. This was used for the next step without further purification. $^1$H NMR (D$_2$O) δ0.8 (t, 6H, CH$_3$), 1.43 (q, 4H, CH$_2$), 1.52 (s, 6H, C(CH$_3$)$_2$), 1.84 (s, 3H, CH$_3$), 2.99 (d, 4H, CH$_2$).

B. 6,6-Diethyl-3,3,9,9-tetramethyl-1-(2-nitro-1H imidazo-1-yl)-4,8-diazaundecane-2,10-dione dioxime Diisopropylethylamine (0.65 g, 0.005 mol) was added to a slurry of N-(2-aminomethyl-2-ethylbutyl)-1-amino-1,1-dimethyl-2-butanone oxime (1.15 g, 0.005 mol) and 3-chloro-3-methyl-1-(2-nitro-1H-imidazo-1-yl)-2-nitrosobutane (1.23 g, 0.005 mol, Example 1) in acetonitrile. The reaction mixture was stirred at room temperature for 48 hours. Acetonitrile was removed under reduced pressure and the residue was chromatographed over silica gel (methylene chloridemethanol, 95.5:0.5). Fractions containing the product were collected and evaporated on a rotary evaporator. The resultant oil was dissolved in a minimum amount of CHCl$_3$ and left in the refrigerator. The solid which formed was removed by filtration, and air dried (0.62 g), m.p. 124°–125° C.

Analysis calc'd for C$_{20}$H$_{37}$N$_7$O$_4$: C, 54.64; M, 8.48; N, 22.29; Found: C, 54.45; M, 8.50; N, 22.16.

Example 16

Synthesis of 6,6-Diethyl-3,3,9,9-tetramethyl-1-(4-nitro-1H-imidazo-1-yl)-4,8-diazaundecane-2,10-dione dioxime Diisopropylethylamine (0.65 g, 0.005 mol) was added to a slurry of N-(2-aminomethyl-2-ethylbutyl)-1-amino-1,1-dimethyl-2-butanoneoxime (0.46 g, 0.002 mol, Example 15) and 3-chloro-3-methyl-1-(4-nitro-1H-imidazo-1yl)-2-nitrosobutane (0.47 g, 0.002 mol, Example 2) in acetonitrile was added and the mixture was stirred at room temperature for 48 hours. Acetonitrile was removed under reduced pressure and the residue was chromatographed over silica gel (methylene chloride-methanol, 80:20). UV positive fractions were collected and evaporated on a rotary evaporator. The light yellow oil obtained solidified on standing (0.52 g) . $^1$H NMR (DMSO-d$_6$): δ0.76 (m, 6H, CH$_3$), 1.24 (m and S, 16H, CH$_2$CH$_3$ and C (CH$_3$)$_2$), 1.48 (s, 3H, CH$_3$) 1.73 and 1.85 (s, 4H, CH$_2$NH), 5.02 (s, 2H, N—CH$_2$), 7.8 and 8.24 (s, 2H, imi.H), 11.1 and 11.8(s, 2H, N—OH).

Analysis calc'd for C$_{20}$H$_{37}$N$_7$O$_4$ . 2.71 H$_2$O: C, 49.19; H. 8.75; N, 20.08; Found: C, 49.17; H, 8.13; N, 19.72.

Example 17

Synthesis of 3,3,9,9-Tetramethyl-1,11-bis2-nitro-1H-imidazo-1-yl)-4,8-diazaundecane-2,10-dione dioxime A slurry of 3-chloro-3-methyl-1-(2-nitro-1H-imidazo-1-yl)-2-nitrosobutane (0.5 g, 0.002 mol, Example 1) in acetonitrile (5 mL) was maintained an 45° C. for 10 minutes. To this suspension was added a mixture of 1,3-propanediamine (75 mg, 0.001 mol) and diisopropylethylamine (300 mg, 0.002 mol). The stirred mixture was maintained at 45° C. for 15 min. A clear solution was formed in 10 minutes. Acetonitrile and diisopropylethylamine were removed on a rotary evaporator and the residue was dissolved in water (0.5 mL) and made basic with aqueous ammonia. The solution was extracted with ethyl acetate, and the ethyl acetate layer was removed and dried with sodium sulfate. Evaporation of ethyl acetate gave an oil which was chromatographed over silica gel (methylene chloride:methanol, 8:2). UV visible fractions were combined and evaporated to give a thick oil which was dried under vacuum. The product was crystallized from acetonitrile (172 mg), mp 163°–64° C. $^1$H NMR (DMSO d$_6$) δ 1.26 (s, 12H, CH$_3$), 1.89 (m, 2H, HNCH$_2$CH$_2$CH$_2$NH), 2.12 (m, 4H, HNCH$_2$CH$_2$CH$_2$NH), 5.22 (s, 2H, CH$_2$N<), 7.07 and 7.23 (s, 2H, imiH), 11.4 (s, 2H, OH). MS (FAB); (M+H)$^+$=495.

Analysis Calc'd for C$_{19}$H$_{30}$N$_{10}$O$_6$.0.56 H$_2$O: C, 45.22; H, 6.22; N, 27.66; Found: C, 45.32; H, 6.09; N, 27.66.

Example 18

Synthesis of 3,3,9,9-Tetramethyl-6-methoxy-1-(2-nitro-1H-imidazo-1-yl)-4,8-diazaundecane-2,10-dione dioxime A. 2-Methoxy-1,3-diaminopropane N,N'-di-t-Boc-2-hydroxydiaminopropane was prepared as follows. To a solution of 1,3-diamino-2-hydroxy propane (25 g, 0.277 mole) in water (20 ml), di-tert-butyl dicarbonate (133 g, 0.61 mole) in THF (200 ml) was added followed by triethylamine (62 g, 0.7 mole) at 0° C. and stirred for 2 hours. The reaction mixture was allowed to come to room temperature and kept stirred for 16 hours more. Solvent THF and triethylamine were removed under aspirator vacuum and the paste was diluted with water (250 ml). The solution was then thoroughly extracted with ethyl acetate (5×100 ml) and the combined organic layer was washed with water and brine. The dried ethyl acetate layer was concentrated under reduced pressure to a gummy residue which was triturated with hexanes to yield a colorless solid. The solid was then recrystallized from hexanes/ether.

Yield: 55.0 g (68%). m.p. 99°–101° C. $^1$H NMR (CDCl$_3$) δ 1.45 (s, 9H, t-C$_4$H$_9$), 3.20 (m, 4H, HNCH$_2$CHOHCH$_2$NH), 3.72 (m, 1H, HNCH$_2$CHOHCH$_2$NH), 5.05 (bs, 1H, NHCO).

Sodium hydride (2.4 g, 0.1 mol) was added in small portions to a solution of the product N,N'-di-t-Boc-2-hydroxypropanediamine (30 g., 103 mol) in dry THF (600 ml) over a period of 30 minutes. Methyl iodide (21.3 g, 0.15 mol) was added dropwise and the mixture stirred at room temperature for 6 hours. Additional methyl iodide (21.3 g, 0.15 mol) was added and the stirring was continued for further 6 hours. THF and excess methyl iodide were removed on a rotary evaporator and the viscous oil obtained was chromatographed over silica gel (hexane:ethyl acetate 9:1). Fractions containing the N,N'-di-t-Boc-2-methoxy 1,3-diaminopropane were collected and evaporated. The resultant oil solidified on standing. It was crystallized from hexane (17.2 g), mp 74°–75° C., $^1$H NMR (CDCl$_3$) δ 1.45 (s, 9H, t-C$_4$H$_9$), 3.05–3.35 (m, 4H, HNCH$_2$CHOCH$_3$CH$_2$NH), 3.41 (s, 3H, OCH$_3$), 5.05 (bs, 1H, NHCO).

N,N'-Di-t-boc-2-methoxy-1,3-diaminopropane (31.7 g, 0.1 mol) was added to methanolic HCl (100 mL) and the solution was stirred at room temperature for 30 minutes. Methanol was removed on a rotary evaporator and the residue was treated with methanolic ammonia to afford the title A compound as a thick viscous oil (9.2 g). $^1$H NMR (D$_2$O) δ 3.08–3.32 (m, 4H, H$_2$NCH$_2$CHOCH$_3$CH$_2$NH$_2$), 3.31 (s, 3H, OCH$_3$), 3.52 (m, 1H, CH)

B. N-(3-Amino-2-methoxypropyl)-1-amino-1,1-dimethyl-2-butanone oxime

The title A compound (9.2 g, 0.091 mol) was dissolved in absolute methanol (50 mL) and the solution was cooled to 0° C. 3-Chloro-3-methyl-2-nitrosobutane (6.25 g, 0.04 mol, Example 1) was added over a period of 1 hour. The reaction mixture was stirred at 0° C. for further 1 hour and at room temperature for 12 hours. Methanol was removed on a rotary evaporator and the residue was dissolved in dioxane-water (2:1, 300 mL) and the solution was cooled to 0° C. Sodium carbonate (21.2 g, 0.2 mol) was added to this solution, followed by di-tert-butyl dicarbonate (42.0 g, 0.2 mol). The reaction mixture was stirred at 0° C. for 1 hour and room temperature for 6 hours. Dioxane-water was removed on a rotary evaporator and the residue was poured into water and extracted with ethyl acetate. The ethyl acetate layer was washed with water and dried (Na$_2$SO$_4$). This solution was evaporated on a rotary evaporator and the residue was chromatographed over silica gel (hexane:ethyl acetate 50:50). N,N'-di-t- boc-2-methoxy-1,3-diaminopropane (formed from the unreacted 2-methoxy-1,3-diaminopropane) eluted first. The t-boc derivative of the product was collected and evaporated to a thick oil which solidified on standing. Yield 7.5 g (25%). $^1$H NMR (CDCl$_3$) δ 1.22 (s, 6H, CH$_3$), 1.42 (s, 9H, t-C$_4$H$_9$), 1.6 (bs, 1H, NH), 1.85 (s, 3H, CH$_3$C=NOH), 2.52–3.28 (m, 4H, HNCH$_2$CHOCH$_3$CH$_2$NH$_2$), 3,41 (s, 3H, OCH$_3$), 4.12 (q, 1H, CH), 5.35 (bs, 1H, NHCO).

The t-Boc derivative (7.5 g, 0.0035 mol) was dissolved in methanolic HCl (50 mL) and the solution was stirred at room temperature for 30 minutes. Anhydrous ether (300 mL) was added and the precipitated amine-oxime hydrochloride was collected by filtration and dried under vacuum. The solid was dissolved in methanol and neutralized with methanolic ammonia. Methanol was removed on a rotary evaporator and the free base thus obtained was dried under vacuum (3.8 g). $^1$H NMR (D$_2$O) δ 1.22 (s, 6H, CH$_3$), 1.81 (s, CH$_3$C=NOH), 2.52–3.18 (m, 4H, HNCH$_2$CHCHOCH$_3$C H$_2$NH$_2$), 3.31 (s, 3H, OCH$_3$), 3.52 (m, 1H, CH).

C. 3,3,9,9-Tetramethyl-6-methoxy-1-(2-nitro-1H-imidazo-1-yl)-4,8-diazaundecane-2,10-dione dioxime Diisopropylethylamine (0.35 g, 0.0028 mol) was added to a slurry of the title B compound (0.5 g, 0.0025 mol) and 3-chloro-3-methyl-1-(2-nitro-1H-imidazo- 1-yl)-2-nitrosobutane (0.7 g, 0.0028 mol, Example 1) in acetonitrile (5 mL), and the reaction mixture was heated to 45° C., with stirring. A clear solution was formed in 15 minutes. The reaction mixture was stirred at 45° C. for a further 1 hour. Acetonitrile was removed on a rotary evaporator and the residue was dried under vacuum. The viscous oil obtained was treated with methanolic ammonia and methanol was removed under vacuum. The resultant oil was chromatographed over silica gel (methylene chloride:methanol 8:2). UV visible fractions were collected and evaporated on a rotary evaporator. The resultant solid was crystallized from acetonitrile (0.12 g), mp 169°–70° C. MS: (M+H)$^+$ calc'd: 414.2465; found: 414.2472.

Anal. calc'd for C$_{17}$H$_{31}$N$_7$O$_5$: C, 49.38; H, 7.56; N, 23.71; Found: C, 49.70; H, 7.59; N, 23.73.

Example 19

Synthesis of [$^{99}$Tc] Oxo[[4,4,10,10-tetramethyl-1-(2-nitro-1H-imidazo-1-yl)-5,9-diazadodecane-3,11-dione dioximatol (3-)-N,N', N", N'''] technetium(V)

Ethylene glycol (150 μL) was added to a stirred solution of [N(t-butyl)$_4$]TcOCl$_4$$^-$ (59.9 mg, 0.120 mmoles) dissolved in 1.0 ml MeOH. This was followed by the addition of 0.75M Na acetate in MeOH (1.5 mL) and 4,4,10,10-tetramethyl-1-(2-nitro-1H-imidazol-1-yl)-5,9-diazadodecane-3,11-dione dioxime (70.6 mg, 0.178 mmoles, Example 3) which caused the solution to turn clear red-orange-brown. After 5 minutes the solvent was removed by rotary evaporation to give a viscous, red-orange, opaque oil. The product was redissolved in methylene chloride, and this solution was washed with water (2×2.5 mL), and then dried over Na$_2$SO$_4$. This solution was evaporated by rotary evaporation to yield to a bright orange solid. The solid was redissolved in <1 ml CH$_2$Cl$_2$, and the product purified by passage through a silica gel column that was conditioned and eluted with diethyl ether. The orange band was collected, and the solvent evaporated to give a bright red solid and which was recrystallized from CH$_2$Cl$_2$/hexane. The product was isolated by suction filtration, rinsed with hexane and dried in vacuo overnight. The yield of the product was 29.5 mg as small, bright orange crystals. M.S.: (M+H)$^+$=510; (MH)$^-$=508.

Analysis calc;d. for C$_{17}$H$_{28}$N$_7$O$_5$Tc: C, 40.08; H, 5.54; N, 19.25; Found: C, 39.92; H, 5.84; N, 19.15.

Example 20

Synthesis of [$^{99m}$TC] Oxo[[3,3,6,6,9,9-hexamethyl-1-(2-nitro-1H-imidazo-1-yl)-4,8-diazaundecane-2,10-dione dioximato](3-)-N,N',N",N'''] technetium (V), by reaction in aqueous ethanol 3,3,6,6,9,9-Hexamethyl-1-(2-nitro-1H-imidazo-1-yl)-4,8-diazaundecane-2,10-dione dioxime (3.08 mg, Example 14) was dissolved in EtOH (1 mL). 0.1M Aqueous sodium bicarbonate solution (0.5 mL) and $^{99m}$TcO$_4$$^-$ in saline (0.8 mL, 57.1 mCi) were added, followed by a saturated solution of stannous tartrate in saline (150 μL). The mixture was shaken, and allowed to stand at room temperature for 10 minutes.

Example 21

Synthesis of [$^{99m}$TC] Oxo[[3,3,9,9-tetramethyl-1-(2-nitro-1H-imidazo-1-yl)-4,8-diazaundecane-2,10-dione dioximato] (3-)-N,N',N",N'''] technetium(V) using SnDTPA as the reducing agent A kit containing 2 mg of the ligand in Example 1 in a lyophilized form was prepared. A vial of the above lyophilized formulation was reconstituted with saline and $^{99m}$Tc-generator eluate, such that the total reconstitution volume was 2 mL and the radioactive concentration adjusted as required. A vial of a commercially-available kit containing 500 μg of stannous chloride and 10 mg of DTPA was reconstituted with 2 mL of saline. 100 μL of the stannous DTPA solution was transferred to the above reconstituted kit of the ligand in Example 1. The vial was shaken and allowed to stand at room temperature for 10 minutes. The radiochemical purity of the product was assayed by HPLC, and determined to be >95%.

The results of the further compounds tested accordance with Example 8 are summarized below.

| Compound name/number | $E_{pc}$(V) | Reduction process |
|---|---|---|
| Compound from Ex. 2 | −1.81 | reversible |
| Compound from Ex. 3 | −1.54 | reversible |
| Compound from Ex. 4 | −1.51 | reversible |
| Compound from Ex. 5 | −1.52 | reversible |
| Compound from Ex. 6a | −1.81 | reversible |
|  | −2.02 | irreversible |
| Compound from Ex. 6b | −1.48 | reversible |
|  | −1.96 | irreversible |
| Compound from Ex. 19 | −1.53 | reversible |
|  | −2.02 | irreversible |

Example 23

Synthesis of 3,3,6,9,9-Pentamethyl-1-(2-nitro-1H-imidazol-1-yl)-4,8-diazaundecane-2,10-dione dioxime A. Preparation of 2-Methyl malonamide Dimethyl methylmalonate (100.0 g, 0.68 mol) in dry methanol (500 mL) was saturated with dry ammonia gas at 0° C. and the reaction mixture was stirred at room temperature for 24 hours. The colorless solid which separated was isolated by filtration, washed and dried to yield the title product; yield: 77.0 g (96%); mp. 209°–210° C.; $^1$H NMR (DMSO-d$_6$) δ 1.34 (d, 3H, CH$_3$), 3.18 (q, 1H, CH), 7.05 & 7.35 (2bs, 4H, CONH$_2$).

B. Preparation of 1,3-Diamino-2-methylpropane

Borane in tetrahydrofuran (THF) (1M, 1100 mL) was added from a syringe to a suspension of 2-methyl malonamide (25.0 g, 215.5 mmol) in THF (50 mL) over a period of 30 minutes, then stirred at 40° C. under nitrogen atmosphere for 24 hours. The reaction mixture was then cooled to 0° C. HCl (2N, 40 mL) was added and the mixture was stirred for 30 minutes. The solvent was removed on a rotary evaporator and the semi-solid thus obtained was co-evaporated with dry methanol (5×20 mL) to remove boric acid. After neutralization with 1N NaOH, the resulting oil was distilled under reduced pressure to provide the title product as a colorless oil.

Yield: 13.65 g (72%); bp. 90°–92° C./108–110 mm. $^1$H NMR (CDCl$_3$) δ 0.96 (d, 3H, CH$_3$), 1.50 (m, 1H, CH), 2.72 (q, 2H, NCH$_2$), 2.55 (q, 2H, NCH$_2$).

C. Preparation of 3-(3-Amino-2-methyl-propylamino)-3-methyl-1-(2-nitroimidazolyl)-2-butanone oxime 3-Chloro-3-methyl-1-(2-nitroimidazolyl)-2-nitrosobutane (1.5 g, 6.09 mmol, Example 1) was added portionwise over a period of 30 minutes to a stirred solution of 1,3-diamino-2-methylpropane (3.0 g, 34.10 mmol) in dry acetonitrile (30 mL) at 50° C. After the addition the reaction mixture was allowed to remain at 50° C. for an additional 30 minutes. The reaction mixture was then cooled and solvent was removed on a rotary evaporator to a give a paste. This was crystallized from dichloromethane-ether to afford the title product as a light yellow solid; yield: 1.36 g (75%); mp. 102°–104° C. (decomp); $^1$H NMR (CDCl$_3$) δ 0.89 (d, 3H, CH$_3$), 1.22[s, 6H, C(CH$_3$)$_2$], 1.51 (m, 1H, CH$_3$CH), 2.25 (d, 2H, CH$_2$NH$_2$), 2.65 (m, 2H, NHCH$_2$), 5.31 (s, 2H, imi-CH$_2$), 7.03 & 7.21 (2s, 2H, imi-H). MS m/e 299 (M+H)$^+$.

D. Preparation of 3,3,6,9,9-pentamethyl-1-(2-nitro-1H-imidazol-1-yl)-4,8-diazaundecane 2,10-dione dioxime 3-Chloro-3-methyl-2-nitrosobutane (1.0 g, 7.38 mmol, Example 1) was added in portions to a stirred solution of 3-(3-amino-2-methylpropyl amino)-3-methyl-1-(2-nitroimidazolyl)-2-butanone oxime (1.0 g, 3.36 mmol) and diisopropylethylamine ((i-Pr)$_2$NEt) (0.48 g, 3.72 mmol) in dry acetonitrile (20 mL) at 50° C. under nitrogen atmosphere. After the addition, the reaction mixture was stirred for an additional 2 hours at 50° C. and cooled to room temperature. The solvent was removed on a rotary evaporator to yield a paste which was repeatedly crystallized from acetonitrile to afford the title product as a cream colored solid; yield: 1.10 g (83%); mp. 167°–168° C. $^1$H NMR (DMSO-d$_6$) δ 0.8 (d, 3H, CH$_3$), 1.31 [s, 6H, C(CH$_3$)$_2$], 1.58 [2s, 6H, C(CH$_3$)$_2$], 1.89 [s, 3H, C(N=OH)CH$_3$], 2.28 (m, 1H, CH$_3$CH), 2.62 & 2.92 (2m, 4H, NHCH$_2$), 5.31 (s, 2H, imi-CH$_2$), 7.06 & 7.22 (2S, 2H, imi-H) and 10.82 & 11.69 (2s, 2H, NOH). MS m/e 398 (M+H)$^+$.

Anal. Calcd for C$_{17}$H$_{31}$N$_7$O$_4$·0.89H$_2$O: C, 47.37; H, 8.12; N, 22.75. Found: C, 47.37; H, 7.85; N, 22.41.

Example 24

Synthesis of 12-Methoxycarbonyl-3,3,9,9-tetramethyl-1-(2-nitro-1H-imidazol-1-yl)-4,8-diazadodecane-2,10-dione dioxime A. Preparation of 5-Methyl-4-hexenonitrile A solution of 5-bromo-2-methyl-2-pentene (9.5 g, 58.28 mmol) in dry dimethylformamide (DMF) (10 mL) was treated with NaCN (5.0 g, 102.04 mmol) and stirred at 80° C. for 15 hours. The reaction mixture was then poured into water and extracted with ethyl acetate (3×50 mL). The combined organic layer was washed with water (2×50 mL), dried and evaporated to provide the title product as a light brown oil (5.5 g, 84%) which was used in the next step without further purification $^1$H NMR (CDCl$_3$) δ 1.62 & 1.75 [2s, 6H, C(CH$_3$)$_2$], 2.32 [m, 4H, (CH$_2$)$_2$], and 5.11 (t, 1H, CH). MS m/e 127 (M+NH$_4$)$^+$.

B. Preparation of 5-Methyl-4-hexenoic acid

5-Methyl-4-hexenonitrile (5.5 g, 50.46 mmol) was treated with NaOH (5N, 50 mL) and heated at 110° C. for 15 hours. After acidification with concentrated HCl to pH 2.0, the solution was extracted with ethyl acetate (3×50 mL). The organic layer was then washed with water (2×50 mL), dried and evaporated under vacuum to afford a brown liquid. This was purified by vacuum distillation. The title product was obtained as a colorless liquid in 70% (4.52 g) yield; b.p. 75°–77° C./0.5 mm. $^1$H NMR (CDCl$_3$) δ 1.65 & 1.73 [2s, 6H, C(CH$_3$)$_2$], 2.38 [m, 4H, (CH$_2$)$_2$], 5.08 (t, 1H, CH) and 10.45 (bs, 1H, COOH).

C. Preparation of Methyl 5-methyl-4-hexenoate

Freshly prepared diazomethane in ether was added to an ice-cooled solution of 5-methyl-4-hexenoic acid (4.5 g, 35.16 mmol) in ether (10 mL) until the solution became slightly yellow in color. The solvent was then evaporated under vacuum to afford the title product as a colorless liquid in near quantitative yield (4.90 g). This product was used in the next reaction step without further purification. $^1$H NMR (CDCl$_3$) δ 1.62 & 1.68 [2s, 6H, C(CH$_3$)$_2$], 2.30 [m, 4H, (CH$_2$)$_2$], 3.69 (s, 3H, COOCH$_3$) and 5.07 (t, 1H, CH).

47

D. Preparation of Methyl 5-chloro-4-nitroso-5-methylhexanoate

A mixture of isoamyl nitrite (12 mL) and methyl 5-methyl-4-hexenoate (4.90 g, 35.00 mmol) was cooled to −15° C. To this stirred solution, concentrated HCl (12.5 mL) was added dropwise from an addition flask maintaining the temperature of the reaction mixture below −5° C. After the addition, the reaction mixture was stirred at 0° C. for 30 minutes, filtered and the precipitate washed with ethanol (−10° C.). The light blue colored solid thus obtained was dispersed in petroleum ether (50 mL), cooled to −50° C. and filtered to provide the title product as a colorless solid. Yield: 3.0 g (41.3%); m.p. 90°–91° C. $^1$H NMR (CDCl$_3$) δ 1.68 & 1.71 [2s, 6H, C(CH$_3$)$_2$], 2.35 [m, 4H, (CH$_2$)$_2$], 3.73 (s, 3H, COOCH$_3$) and 5.11 (t, 1H, CH). MS m/e 208 (M+H)$^+$.

E. Preparation of 3-(Aminopropyl)-3-methyl-1-(2-nitroimidazolyl]-2-butanone oxime 3-Chloro-3-methyl-1-(2-nitroimidazolyl)-2-nitrosobutane (1.00 g, 4.06 mmol, Example 1) was added in portions over a period of 20 minutes to a stirred solution of 1,3-diaminopropane (1.0 g, 13.50 mmol) in dry acetonitrile at 50° C. After the addition, the reaction mixture was maintained at 50° C. for an additional 30 minutes. The reaction mixture was then cooled and filtered to provide the title compound as a yellow colored solid. For further purification, the solid was suspended in a small amount of water, stirred and filtered to afford the title product in >97% purity; yield: 0.78 g, (68%); mp: 136°–137° C. $^1$H NMR (DMSO-d$_6$) δ 1.19 [s, 6H, C(CH$_3$)$_3$], 1.37 (m, CH$_2$CH$_2$CH$_2$), 1.52 (bs, 1N, NH), 2.21 & 1.54 (2t, 4H, NHCH$_2$), 5.22 (s, 2H, imida-CH$_2$), 7.05 & 7.27 (2s, 2H, imida-ring H) and 11.42 (bs, 1H, NOH). MS m/e 285 (M+H)$^+$.

F. Preparation of 12-methoxycarbonyl-3,3,9,9-tetramethyl-1-(2-nitro-1H-imidazol-1-yl)-4,8-diazadodecane-2,10-dione dioxime Methyl 5-chloro-5-methyl-4-nitrosohexanoate (0.40 g, 1.92 mmol) was added to a suspension of 3-(aminopropyl)-3-methyl-1-(2-nitroimidazolyl)-2 -butanone oxime (0.50 g, 1.76 mmol) and N,N-diisopropylethylamine (0.26 g, 2.02 mmol) in dry acetonitrile (25 mL), and the mixture was stirred at room temperature for 5 hours under nitrogen atmosphere. The solvent was removed on a rotary evaporator and the paste thus obtained was triturated with dichloromethane to afford the title product as a light yellow colored solid (0.8 g), which was purified by crystallization from acetonitrile; mp. 137°–139° C.; $^1$H NMR (DMSO-d$_6$) δ 1.27 [s, 6H, C(CH$_3$)$_2$], 1.48 [s, 6H, C(CH$_3$)$_2$], 1.78 (m, 2H, NH), 2.51 & 2.79 [2s & m, 10H, NH(CH$_2$)$_3$NH, (CH$_2$)$_2$COOCH$_3$], 3.62 (s, 3H, COOCH$_3$), 5.29 (s, 2H, imi-CH$_2$), 7.10 & 7.29 (2s, 2H, imi-H) and 11.35 & 11.71 (2s, 2H, NOH). MS m/e 456 (M+H)$^+$. Anal. Calcd for C$_{19}$H$_{33}$N$_7$O$_6$·0.98H$_2$O: C, 48.36; H, 7.42; N, 20.78. Found: C, 48.18; H, 7.31; N, 20.69.

Example 25

Synthesis of 1-Ethoxy-3,3,9,9-tetramethyl-1-(2-nitro-1H-imidazol-1-yl)-4,8-diazaundecane-2,10-dione dioxime A. Preparation of 1-Ethoxy-3-methyl-2-butene Freshly prepared silver oxide (101 g, 0.37 mol) was added to a mixture of 3-methyl-2-buten-1-ol (21.0 g, 25 mL, 0.24 mol) and ethyl iodide (300 mL) and the stirred mixture was heated in an oil bath at 45° C. for 6 hrs. Silver salts were removed by filtration and the filter cake was washed with ether (250 mL). The filtrate and the washings were combined and evaporated to remove ether and excess ethyl iodide. The oil thus obtained was distilled under atmospheric pressure to yield 14.8 g (51%) of tht title product as a colorless liquid. bp 119°–120° C. $^1$H NMR (CDCl$_3$) δ 1.2 (t, 3H, CH$_2$CH$_3$), 1.72 (d, 6H, CH$_3$), 3.45 (m, 2H, CH$_2$CH$_3$), 3.95 (d, 2H, CH$_2$), 5.38 (t, 1H, (CH$_3$)$_2$C=CH—).

B. Preparation of 3-Chloro-3-methyl-1-ethoxy-2-nitrosobutane

Concentrated HCl was added to a cooled (0°–5° C.) solution of isoamyl nitrite (14.0 g, 0.12 mol) and 1-ethoxy-3-methyl-2-butene (6.84 g, 0.06 mol). The temperature was maintained below 5° C. during the addition and the reaction mixture was stirred at 5° C. for an additional 30 min. The product was filtered and washed with a cold (−20° C.) 1:1 mixture of ethanol and ether. The solid was further washed with ether to afford the title product as a white solid. Yield 6.9 g (64%). mp: 84°–85° C. $^1$H NMR (CDCl$_3$) δ 1.12 (t, 3H, CH$_2$CH$_3$), 1.65 (d, 6H, CH$_3$), 3.49 and 3.95 (m, 2H, CH$_2$OCH$_2$CH$_3$), 4.15 (m, 2H, CH$_2$CH$_3$), 6.12 (dd, 1H, [CH$_3$)$_2$C=CH—]. MS: 180 (M+H)$^+$.

C. Preparation of 11-ethoxy-3,3,9,9-tetramethyl-1-(2-nitro-1H-imidazol-1-yl) 4,8-diazaundecane-2,10-dione dioxime 3-Chloro-3-methyl-1-ethoxy-2-nitrosobutane (180 mg, 1.0 mmol) was added to a suspension of 3-(aminopropyl)-3-methyl-1-(2-nitroimidazolyl)-2-butanone oxime (280 mg, 1.0 mmol, Example 24) and N,N-diisopropylethylamine (130 mg, 1.0 mmol) in dry acetonitrile (15 mL), and the reaction mixture was stirred at room temperature for 6 hours under nitrogen atmosphere. The solvent was then removed on a rotary evaporator and the thick oil obtained was triturated with dichloromethane to afford the title product. This was purified by column chromatography (silica gel, CH$_2$Cl$_2$: CH$_3$OH), and crystallization from acetonitrile. mp. 122°–23° C. $^1$H NMR (D$_2$O) δ 1.12 (t, 3H, CH$_2$CH$_3$), 1.32 and 1.45 [s, 12H, C(CH$_3$)$_2$], 1.82 (m, 2H, NHCH$_2$CH$_2$CH$_2$NH), 2.68 and 2.90 (m, 4H, NHCH$_2$CH$_2$CH$_2$NH), 3.55 (s, 3H, OCH$_2$CH$_3$), 4.29 (s, 2H, CH$_2$OCH$_2$CH$_3$) 5.29 (s, 2H, CH$_2$), 7.10 and 7.24 (s, 2H, imiH). HRMS: Calcd. (M+H)$^+$=428.2622$^+$; Found: (M+H)$^+$=428.2624$^+$. Anal. calcd. for: C$_{18}$H$_{33}$N$_7$O$_5$; C, 50.57; H, 7.78, N, 22.93; Found: C, 51.00, H, 7.80; N, 22.48.

Example 26

Synthesis of 3,3,9,9-Tetramethyl-6-[2-hydroxy-3-(2-nitro-$^1$H-imidazol-1-yl)propyl]-4,8-diazaundecane-2, 10-dione dioxime A. Preparation of 2-Allyl-malonamide Diethyl 2-allyl-malonate (100 g, 0.649 mole) was dissolved in methanol (500 mL) and the solution was cooled 0° C. in ice bath. Gaseous ammonia was bubbled into the solution to saturation while the solution was cooled in an ice bath. The reaction mixture was sealed and stirred at room temperature for 20 hours. Solvent and ammonia were removed by rotary evaporation, and the residue was washed with ether to give the title product as a white solid. This was used for the next step without further purification. Yield: 76.5 g (92%). mp: 168°–169° C. 1H NMR (DMSO) δ 2.4 (m, 2H, CH$_2$CH=CH$_2$); 3.0 (t, 1H, COCHCO); 5.0 (m, 2H, CH$_2$CH=CH$_2$); 5.7 (m, 1H, CH$_2$CH=CH$_2$); 7.0 (bs, 2H, CONH$_2$); 7.3 (bs, 2H, CONH$_2$).

B. Preparation of 2-Allyl1-N,N'-di-t-Boc-1,3-propanediamine

To a slurry of lithium aluminum hydride (11.8 g, 0.3 mol) in dimethoxyethane (300 mL) was added a warm solution of 2-allyl-malonamide (14.2 g, 0.1 mole) in dimethoxyethane (800 mL) over a period of 1 hour. The reaction mixture was stirred at 50° C. for 48 hours. Excess lithium aluminum hydride was destroyed by the addition of 10% NaOH and water and the mixture was stirred at room temperature for 2 hours. Di-t-butyldicarbonate (50.0 g, 0.23 mole) was added and the reaction mixture was stirred for 24 hours. The reaction mixture was filtered, and the filter cake washed with $CH_2Cl_2$ (250 mL). The filtrate and the washings were collected and evaporated on a rotary evaporator to afford a thick viscous oil. This oil was purified by column chromatography (silica gel, hexane:ethyl acetate, 9:1). Fractions containing the product were collected, combined, and evaporated to give a thick oil which solified on standing. Trituration with pentane gave the title product as a white solid. mp: 84°–87.5° C. $^1$H NMR ($CDCl_3$) δ 1.4 (s, 18H, t-Boc), 1.7 (m, 1H, CH), 2.85 and 3.22 (m, 4H, $CH(CH_2NH)$ ), 5.0 (m, 2H, $CH_2=C$), 5.75 (m, 1H, $—CH=CH_2$). MS: $(M+H)^+=315$.

C. Preparation of 2-(2,3-Epoxypropyl)-N,N'-di-t-Boc-1,3-propanediamine m-Chloroperbenzoic acid (5.0 g, 0.022 mol) was added portionwise to a cooled (0° C.) solution of 2-allyl-N,N'-di-t-Boc-1,3-propanediamine (5.0 g, 0.016 mol) in $CH_2Cl_2$ (30 mL), and the solution was stirred for 24 hours. The precipitated m chlorobenzoic acid was removed by filtration and the filtrate was taken up in ether (200 mL). Excess m-chloroperbenzoic acid was decomposed by the addition of sodium sulfite solution (20%, 10 mL). The ether layer separated and was washed with a saturated solution of sodium bicarbonate, water and dried ($Na_2SO_4$). Evaporation of ether gave the title product as a viscous oil which was used in the next step without further purification. Yield: 5.2 g (98%). $^1$H NMR ($CDCl_3$) δ 1.5 (m, 3H, CH and $CH_2CH—$ ), 2.45 and 2.80 (m, 2H, epoxide), 3.0–3.4 (m, 5H, 1H epoxide and $(CH_2NHtBoc)_2$), 5.0 and 5.5 (m, 2H, NHtBoc). MS: $(M+H)^+=330$.

D. Preparation of 2-(2-Hydroxy-3-(2-nitroimidazolyl)-propyl)-N,N'-di-t-Boc-1,3-propanediamine 2-(2,3-Epoxypropyl)-N,N'-di-t-Boc-1,3-propanediamine (1.0 g, 0.003 mol) was added to a mixture of 2-nitroimidazole (500 mg) and potassium carbonate (70 mg) in ethanol (50 mL). The mixture was refluxed under nitrogen for 12 hours. The reaction mixture was cooled and filtered. The precipitate was washed with water and the off-white solid thus obtained was air dried. The crude product was chromatographed over silica gel ($CH_2Cl_2$:$CH_3OH$ 95:5). The UV visible fractions were collected and evaporated to give the title product as a white solid, which was used in the next step without further purification. Yield: 420 mg (28%). $^1$H NMR (DMSO) δ 1.2 (m, 2H, $CHCH_2CHOH—$), 1.75 (m, 1H, $CHCH_2CHOH—$), 2.9 (m, 4H, $CH(CH_2NHtBoc)_2$), 3.9 (m, 1H, CHOH), 4.1–4.4 (m, 2H, $CHOHCH_2N$), 5.0 (m, 1H, OH), 6.65 (m, 2H, NH), 7.1- and 7.52 (s, 2H, imi.H). MS: $(M+H)^+=443$.

E. Preparation of 2-(2-Hydroxy-3-(2-nitroimidazolyl)-propyl)-1,3-propanediamine 2-(2-Hydroxy-3-(2-nitroimidazolyl)-propyl)-N,N'-di-t-Boc-1,3-propanediamine (0.9 g, 0.002 mole) was treated with methanolic HCl (5 mL) and the mixture was stirred for 30 minutes at room temperature. Methanol was removed on a rotary evaporator and the residue was neutralized with methanolic ammonia. The methanolic solution was concentrated on a rotary evaporator and the residue was dried under vacuum to yield the title product as a light yellow solid. This solid was used in the next step without further purification. Yield: 0.38 g (80.0%). $^1$H NMR ($D_2O$) δ 1.6 (m, 2H, $CH_2CHOHCH_2N<$), 2.2 (m, 2H, $CH(CH_2NH)$, 2.98 (m, 2H, $CH_2CHOHCH_2N<$) 4.05 (m, 1H, CHOH), 4.3–4.55 (m, 2H, $CHOHCH_2N<$), 7.1 and 7.32 (s, 2H, NCH=CH).

F. Preparation of 3,3,9,9-Tetramethyl-6-(2-hydroxy-3-(2-nitro-1H-imidazol-1-yl)-n-propyl)-4,8-diazaundecane-2,10-dione 2-Bromo-2-methylbutan-3-one (400 mg, 0.0024 mol, Example 5) was added to mixture of the 2-(2-hydroxy-3-(2-nitroimidazolyl)-propyl)-1,3-propanediamine (240 mg, 0.001 mole) and sodium bicarbonate (200 mg, 0.00245 mol) in DMF (2 mL), and the mixture was stirred at 45° C. for 6 hours. DMF was removed under reduced pressure and the residue was triturated with methylene chloride (3×5 mL). Methylene chloride was removed on a rotary evaporator and the oil thus obtained was chromatographed over silica gel ($CH_2Cl_2$: methanol, 8:2). UV visible portions were collected and evaporated to give the title product diketone as an oil. Yield 100 mg (25%). $^1$H NMR ($CDCl_3$) δ 1.52 [d, 12H, $C(CH_3)_2$], 2.12 (s, 6H, $CH_3>=O$), 2.35–3.12 (m, 5H, $CH(CH_2NH)$, 4.1 (m, 1H, CHOH ), 4.3–4.6 (m, 2H, $CHOHCH_2N<$), 7.1 and 7.42 (s, 2H, NCH=CH).

G. Preparation of 3,3,9,9-Tetramethyl-6-[2-hydroxy-3-(2-nitro-1H-imidazol-1-yl)propyl]-4,8-diazaundecane-2,10-dione dioxime O-Trimethylsilylhydroxylamine (1 mL) was added to a solution of 3,3,9,9-tetramethyl-6-(2-hydroxy-3-(2-nitro-1H-imidazol-1-yl)-n-propyl)-4,8-diazaundecane-2,10-dione (10) mg, 0.00025 mole) in methylene chloride (1.0 mL) and the reaction mixture was stirred at room temperature for 24 hours. Methanol was added to the reaction mixture and the resultant oil was isolated and chromatographed over silica gel ($CH_2Cl_2$: methanol, 9:1). UV visible portions were collected and evaporated to give the product. This was dissolved in minimum amount of water and freeze dried. The freeze dried solid was recrystallized from acetonitrile to yield the title product. Yield 45 mg (25%). mp 185°–87° C. $^1$H NMR ($D_2O$) δ 1.22 [d, 12H, $C(CH_3)_2$], 1.80 (s, 6H, $CH_3>=N$), 2.8 (m, 5H, $CH(CH_2NH)$, 3.82 (m, 1H, CROH), 4.2–4.58 (m, 2H, $CHOHCH_2N<$), 7.1 and 7.32 (s, 2H, NCH=CH). MS: Calcd for $C_{19}H_{36}NO_5$ 442.2778 $(M+H)^+$. Found. 442.2781.

Example 27

Synthesis of 3,3,9,9-Tetramethyl-1-(4-methyl-2-nitro-1H-imidazol-1-yl)-4,8-diazaundecane-2,10-dione dioxime A. Preparation of 1-(4-Methyl-2-nitro-1H-imidazol-1-yl) -3-methyl-2-butene and 1-(5-Methyl-2-nitro-1H-imidazol-1-yl)-3-methyl-2-butene 3,3-Dimethylallyl bromide (14.08 g, 94.49 mmol) was added to a suspension of anhydrous $K_2CO_3$ (13.0 g, 94.20 mmol) and 4-methyl-2-nitroimidazole (10.0 g, 78.74 mmol, D. P. Davies et al, *J. Heterocyclic Chem.*, 1982, 19, 253–256) in dry acetone (100 mL). The reaction mixture was stirred at room temperature under nitrogen atmosphere for 15 hours. The insoluble inorganic material was removed by filtration and the filtrate was evaporated to afford a brown paste which was loaded onto a silica gel column and eluted with hexane ethyl acetate (8.5:1.5). The fractions containing the compound with $R_f$ 0.51 (silica gel TLC, hexane-ethyl acetate, 7:3) were collected and evaporated to afford a solid which was recrystallized from ethyl acetate-hexane to provide 1-(4-methyl-2-nitro-1H-imidazol-1-yl)-3-methyl-2-butene as a light yellow crystalline solid in 60% (9.21 g) yield; mp. 53°—54° C; $^1$H NMR ($CDCl_3$) δ 1.80 [s, 6H, $C(CH_3)_2$], 2.26 (s, 3H, imi-$CH_3$), 4.97 (d, 2H, J=7.26 Hz, $NCH_2$), 5.36 (t, 1H, J=7.26 Hz, $CH_2CH$) and 6.90 (s, 1H, imi-CH). $^{13}$C NMR ($CDCl_3$) δ 13.80 (imi-$CH_3$), 18.16 & 25.70 [$C(CH_3)_2$], 47.76 ($NCH_2$), 117.35 ($CH_2CH$), 122.77

(imi-CH), 138.09 [C(CH$_3$)$_2$], 139.97 (imi-CCH$_3$) and 143.53 (CNO$_2$). MS m/e 196 (M+H)$^+$.

The fractions containing the compound with R$_f$ 0.41 (silica gel, hexane-ethyl acetate 7:3) were pooled and evaporated to provide a solid which was recrystallized from ethyl acetate-hexane to afford 1-(5-methyl-2-nitro-1H-imidazol-1-yl)-3-methyl-2-butene as a light yellow fluffy solid. Yield: 1.02 g (15.2%); mp. 78°–79° C.; $^1$H NMR (CDCl$_3$) δ 1.75 & 1.82 [2s, 6H, C(CH$_3$)$_2$], 2.32 (s, 3H, imi-CH$_3$), 4.97 (d, 2H, J=6.60 Hz, NCH$_2$), 5.13 (t, 1H, J=6.55 Hz, CH$_2$CH) and 6.97 (s, 1H, imi-CH). $^{13}$C NMR (CDCl$_3$) δ 10.35 (imi-CH$_3$), 18.28 & 25.62 [C(CH$_3$)$_2$], 45.20 (NCH$_2$), 117.69 (CH$_2$CH), 127.07 (imi-CH), 134.49 [C(CH$_3$)$_2$], 137.57 (imi-CCH$_3$) and 145.52 (CNO$_2$). MS m/e 196 (M+H)$^+$.

B. Preparation of 3-Chloro-3-methyl-2-nitroso-1-(4-methyl-2-nitro-1H-imidazol-1-yl)butane Concentrated HCl (20 mL) was added from an addition flask to a mixture of 1-(4-methyl-2-nitro-1H-imidazol-1-yl)-3-methyl-2-butene (5.0 g, 25.64) and isoamyl nitrite (20 mL), keeping the temperature in the range of 0° C. to 5° C. After the addition the reaction mixture was stirred at ice-cold temperature for 30 minutes. The solid which formed was removed by filtration and washed with ice-cold ethanol. The solid was dispersed in acetonitrile, cooled 0° C. and filtered to provide the title product as a light blue colored solid; yield: 4.97 g (62%); mp. 110°–113° C. (decomp); $^1$H NMR (DMSO-d$_6$) δ 1.81 [s, 6H, C(CH$_3$)$_2$], 2.16 (s, 3H, imi-CH$_3$), 5.36 (s, 2H, NCH$_2$), 7.12 (s, 1H, imi-CH) and 11.98 (s, 1H, NOH). MS m/e 261 (M+H)$^+$.

C. Preparation 3,3,9,9-Tetramethyl-1-(4-methyl-2-nitro-1H-imidazol-1-yl)-4,8-diazaundecane-2,10-dione dioxime 3-Chloro-3-methyl-2-nitroso-1-(4-methyl-2-nitro-1H-imidazol-1-yl)butane (3.41 g, 13.09 mmol) was added in portions to a stirred solution of N-(3-aminopropyl)-1-amino-1,1-dimethyl-2-butanone oxime (2.0 g, 11.56 mmol, Example 1) and (i-Pr)$_2$NEt (1.64 g, 13.09 mmol) in dry acetonitrile (20 mL) at 50° C. under a nitrogen atmosphere. After the addition the reaction mixture was stirred for an additional 2 hours at 50° C. and cooled to room temperature. The solid which formed was filtered and recrystallized from acetonitrile to provide the title product as a light yellow colored solid.

Yield: 3.08 g (59.4%); mp. 140°–141° C.; $^1$H NMR (DMSO-d$_6$) δ 1.12 & 1.10 [2s, 6H, C(CH$_3$)$_2$], 1.33 (m, 2H, CH$_2$CH$_2$CH$_2$), 1.70 [s, 3H, C(=N)CH$_3$], 1.79 (bs, 2H, NH), 2.15 (s, 3H, imi-CH$_3$), 2,19 (m, 4H, NHCH$_2$), 5.19 [s, 2H, NCH$_2$C(=N)], 7.05 (s, 1H, imi-CH) and 10.33 & 11.36 (2s, 2H, NOH). MS m/e 398 (M+H)$^+$.

Example 28

Synthesis of 3,3,9,9-Tetramethyl-1-(5-methyl-2-nitro-1H-imidazol-1-yl)-4,8-diazaundecane-2,10-dione dioxime A. Preparation of 3-Chloro-3-methyl-2-nitroso-1-(5-methyl-2-nitro-1H-imidazol-1-yl)butane 3-Chloro-3-methyl-2-nitroso-1-(5-methyl-2-nitro-1H-imidazol-1-yl)butane was prepared in 60% yield from 1-(5-methyl-2-nitro-1H-imidazol-1-yl)-3-methyl-2-butene (1.0 g, 5.12 mmol, Example 27), isoamyl nitrite (5.0 mL) and concentrated HCl (5.0 mL) following the procedure described for the preparation of its positional isomer (Example 27B) as a light blue solid; mp. 102°–105° C. (decomp); $^1$H NMR (DMSO-d$_6$) δ 1.73 [s, 6H, C(CH$_3$)$_2$], 2.32 (s, 3H, imi-CH$_3$), 5.53 (s, 2H, NCH$_2$), 6.97 (s, 1H, imi-CH) and 11.58 (s, 1H, NOH). MS m/e 261 (M+H)$^+$.

B. Preparation of 3,3,9,9-Tetramethyl-1-(5-methyl-2-nitro-1H-imidazol-1-yl)-4,8-diazaundecane-2,10-dione dioxime 3,3,9,9-Tetramethyl-1-(5-methyl-2-nitro-1H-imidazol-1-yl)-4,8-diazaundecane-2,10-dione dioxime was synthesized in 58% (0.66 g) yield as a yellow crystalline solid from 3-chloro-3-methyl-2-nitroso-1-(5-methyl-2-nitroimidazolyl)butane (0.75 g, 2.88 mmol), N-(3-aminopropyl)-1-amino-1,1-dimethyl-2-butanone oxime (0.45 g, 2.60 mmol, Example 1) and (i-Pr)$_2$NEt (0.37 g, 28.62 mmol) in dry acetonitrile (10 mL) at 50 C. following the method described for the preparation of its positional isomer (Example 27C); mp. 150°–152° C.; $^1$H NMR (DMSO-d$_6$) δ 1.01 & 1.13 [2s, 6H, C(CH$_3$)$_2$], 1.40 (m, 2H, CH$_2$CH$_2$CH$_2$), 1.68 (bs, 2H, NH), 1.71 [s, 3H, C(=N)CH$_3$], 2.25 (s, 3H, imi-CH$_3$), 2.20 (m, 4H, NHCH$_2$), 5.36 [s, 2H, NCH$_2$C(=N)], 6.91 (s, 1H, imi-CH) and 10.36 & 11.06 (2s, 2H, NOH). MS m/e 398 (M+H)$^+$.

Example 29

Synthesis of the $^{99m}$Tc Complexes of the Ligands of Examples 23 to 28

The $^{99m}$Tc complexes of the ligands prepared in Examples 23 to 28 above were prepared as follows:

The ligand prepared as the title compound of the Example (9 μmoles; 3.6 to 4.1 mg, the latter depending on the molecular weight of the ligand) was dissolved in methanol (0.1 ml) in a 5 ml glass vial, and 0.1M NaHCO$_3$ buffer (0.5 ml), 0.9% saline, and $^{99}$Mo/$^{99m}$Tc generator eluate (total saline/eluate volume=1.4 ml) were added. The vial was sealed, and a saturated solution of stannous tartrate in saline (50 μl) was added to the vial. The vial was shaken to mix the reagents, and allowed to stand at room temperature for 3 minutes. The radiochemical purities (RCP) of the $^{99m}$Tc complexes were measured by reversed phase HPLC as described above in Example 7a. All ligands labeled to give RCP values >94% within 3 minutes after mixing. The complexes so obtained from the ligands of Examples 23 to 28 were, respectively:

Oxo[[3,3,6,9,9-pentamethyl-1-(2-nitro-1H-imidazol-1-yl)-4,8-diazaundecane-2,10-dione dioximato](3-)-N, N',N'',N''']technetium-$^{99m}$Tc(V);

Oxo[[12-methoxycarbonyl-3,3,9,9-tetramethyl-1-(2-nitro-1H-imidazol-1-yl)-4,8-diazadodecane-2,10-dione dioximato](3-)-N,N',N'',N''']technetium-$^{99m}$Tc(V);

Oxo[[(11-ethoxy-3,3,9,9-tetramethyl-1-(2-nitro-1H-imidazol-1-yl)-4,8-diazaundecane-2,10-dione dioximato](3-)-N,N',N'',N''']technetium-$^{99}$Tc(V);

Oxo[[3,3,9,9-tetramethyl-6-[2-hydroxy-3-(2-nitro-1H-imidazol-1-yl)propyl]-4,8-diazaundecane-2,10-dione dioximato](3-)-N,N',N'',N''']technetium-$^{99m}$Tc(V);

Oxo[[3,3,9,9-tetramethylol-(4-methyl-2-nitro-1H-imidazol-1-yl)-4,8-diazaundecane-2,10-dione dioximato]-(3-)-N,N',N'',N''']technetium-$^{99m}$Tc(V); and Oxo[[3,3,9,9-tetramethyl-1-(5-methyl-2-nitro-1H-imidazol-1-yl)-4,8-diazaundecane-2,10-dione dioximato]-(3-)-N,N',N'',N''']technetium-$^{99m}$Tc(V).

Example 30

6,6-Difluoro-3,3,9,9-tetramethyl-12-(2-nitro-1H-imidazol-1-yl)-4,8-diazadodecane-2,10-dione dioxime A. 1,2-Diamino-2,2-difluoropropane dihydrochloride To a suspension of 2,2-difluoromalonamide (10 g, 90%, 65.22 mmol) in dry tetrahydrofuran (THF) (20 mL) was added BH$_3$-THF (350 mmol, 1M, 350 mL) dropwise from a syringe over a period of 30 minutes. The reaction mixture was then stirred at 45° C. under nitrogen atmosphere for 24 hours. To the ice-cold reaction mixture HCl (2N, 50 mL) was added and the reaction mixture was stirred for 30 minutes. The solvent was then removed on a rotary evaporator and the semi-solid thus obtained was dissolved in water (100 mL), and treated with di-t-butyl dicarbonate (32.0 g, 147.8 mmol) in dioxane (200 mL) and Na$_2$CO$_3$ (30.0 g, 280 mmol). After stirring overnight at ambient temperature, the reaction mixture was concentrated (50 mL), and extracted with ethyl acetate (4×75 mL). The combined extracts gave a colorless solid on evaporation under vacuum. For further purification, the compound (impregnated with silica gel) was loaded onto a silica gel column and eluted with a hexane-ethyl acetate (7:3) solvent mixture. The fractions with compound were collected and evaporated to provide 1,3-bis-N-t-butyloxycarbonyl 2,2-difluoropropanediamine as a colorless crystalline solid in 48% yield (9.70 g); TLC [silica gel, hexane-ethyl acetate (6:4)]R$_f$ 0.54; mp. 125°–125° C.; $^1$H NMR (CDCl$_3$) d 1.45 [s, 18H, C(CH$_3$)$_3$], 3.52 (m, 4H, NHCH$_2$) and 5.26 (bt, 2H, NH). MS m/e 311 (M+H)$^+$.

A solution of 1,3-bis-N-t-butyloxycarbonyl 2,2-difluoropropanediamine (4.5 g, 14.52 mmol) in CH$_3$OH (5 mL) was treated with methanolic HCl (5 mL) at 0° C. and stirred for 20 minutes. The removal of the volatiles under vacuum afforded a colorless crystalline solid of 1,3-diamino-2,2-difluoropropane as a hydrochloride salt in near quantitative yield (4.85 g); mp. 187°–190° C.; $^1$H NMR (D$_2$O) d 3.62 (t, J$_{HF}$=16.20 Hz, 4H, NHCH$_2$). MS m/e 111 (M+H)$^+$.

B. 4-(3-Amino-2,2-difluoropropylamino)-4-methyl-1-(2-nitro-1H-imidazol-1-yl)-3-pentanone oxime To a mixture of 1,3-diamino-2,2-difluoropropane dihydrochloride (title A diamine) (1.10 g, 6.01 mmol) and N,N-diisopropylethylamine (2.72 g, 21.04 mmol) in acetonitrile (10 mL) at 40° C. was added 4-chloro-4-methyl-1-(2-nitro-1H-imidazol-1-yl)-3-nitrosopentane (Example 3, step (B)) (0.50 g, 1.90 mmol) in small portions with 30 stirring under nitrogen atmosphere. After the addition, the stirring was continued for an additional 30 minutes and the solvent was removed on a rotary evaporator. The paste obtained was treated with silica gel and the silica gel powder impregnated with the compound was loaded onto a silica gel column and eluted with CH$_3$OH—CH$_2$Cl$_2$ (5:95). The fractions containing compound were collected and evaporated to give the title product as a light yellow colored solid. Yield: 0.42 g (66%), mp: 112°–114° C.; $^1$H NMR (CDCl$_3$) d 1.19 [s, 6H, C(CH$_3$)$_2$], 2.88 [m, 4H, C(=N)CH$_2$ & NHCH$_2$], 3.71 (t, 3H, J$_{HF}$=13.19 Hz, CH$_2$NH$_2$), 4.72 (t, 2H, J=7.26, CH$_2$CH$_2$N), 7.11 & 7.26 (2s, 2H, nitroimid-H) and 10.79 (s, 1H, NOH). MS m/e 335 (M+H)$^+$.

C. 6,6-Difluoro-3,3,9,9-tetramethyl-12-(2-nitro-1H-imidazol-1-yl)-4,8-diazadodecane-2,0-dione dioxime A clear solution of 4-(3-amino-2,2-difluoropropylamino-4-methyl-1-(2-nitro-1H-imidazol-1-yl)-3-pentanone oxime title B compound) (0.40 g, 1.20 mmol) and N,N-diisopropylethylamine (0.42 g, 3.32 mmol) in acetonitrile (5 mL) was treated with 3-chloro-3-methyl-2-nitrosobutane (prepared analogously to 3-chloro-3-methyl-2-nitroisobutane, Example 1, step (B)) (0.45 g, 3.32 mmol) with stirring at room temperature under nitrogen atmosphere for 2 hours. After evaporation of the solvent under vacuum, the paste thus obtained was loaded, as a powder adsorbed on silica gel, onto a silica gel column and eluted with methanol-dichloromethane (2:98). The fractions with compound were pooled together and evaporated to afford the title product, which was further purified by crystallization from CH$_2$Cl$_2$—CH$_3$OH to a cream colored solid. Yield: 0.45 g (89%); mp. 90°–92° C.; $^1$H NMR (DMSO-d$_6$) d 1.12 [s, 12H, C(CH$_3$)$_2$], 1.70 [s, 3H, C(=NOH)CH$_3$], 2.18 & 2.22 (2t, 2H, NH), 2.62 (m, 4H, CH$_2$CF$_2$), 2.80 (t, 2H, J=7.25 Hz, CH$_2$CH$_2$N), 4.61 (t, 2H, J=7.25 Hz, CH$_2$CH$_2$N), 7.15 & 7.52 (2s, 2H, imi-H) and 10.46 & 10.90 (2s, 2H, NOH). MS m/e 434 (M+H)$^+$. Anal. Calcd for C$_{17}$H$_{29}$N$_7$O$_4$F$_2$: C, 47.11; H, 7.74; N, 22.62; F, 8.77. Found: C, 47.28; H, 6.54; N, 22.79; F, 8.53. HPLC: Retention time: 20.74 min [Microsorb-C$_{18}$, 0.46×25 cm, 5 m; solvent: 0.1% trifluoroacetic acid (TFA)/water (A) and 0.1% TFA/acetonitrile (B); flow rate: 1.0 mL/min.; run condition: linear gradient, 1% increase in B per min.; ran at 230 and 254 nm for 50 min.; in both cases a single peak was observed; 98.95% (230 nm) and 100% (254 nm)].

Example 31

3,3,9,9-Tetramethyl-1-[2-hydroxy-3-(2-nitro-1H-imidazol-1-yl)propoxy]-4,8-diazaundecane-2,10-dione dioxime A. 3,3-Dimethylallylglycidyl ether To a solution of dimethylallyl alcohol (17.3 g, 20.5 mL, 0.2 mol) in dry THF (200 mL), sodium hydride (4.8 g, 0.2 mol) was added in portions and the mixture was stirred at room temperature for 1 hour. Epibromohydrin (27.4 g, 17.12 mL, 0.2 mol) was added to this reaction mixture dropwise and the mixture was stirred at room temperature for 24 hours. THF was removed on a rotary evaporator and the residue was taken up in ether and filtered. The ether solution was concentrated on a rotary evaporator and the brown oil obtained was distilled under vacuum to yield the title product. bp. 93°–94° C./10 mm. Yield: 17.2 g (60.5%). $^1$H NMR (CDCl$_3$) δ 1.68 and 1.75 (s, 6H, CH$_3$), 2.61 and 2.88 (dd, 2H, oxirane CH$_2$), 3.17 (m, 1H, oxirane CH), 3.38 and 3.7 (m, 2H, CH$_2$OCH$_2$CH), 4.05 (m, 2H, CH$_2$OCH$_2$CH), 5.35 (m, 1H, >C=CH).

B. 1-[2-Hydroxy-3-(2-nitro-1H-imidazol-1-yl)-propyldimethylallyl ether

To a mixture of 3,3-dimethylallylglycidyl ether (title A epoxide) (9.0 g, 0.063 mol) and 2-nitroimidazole (7.2 g, 0.063 mol) in ethanol (75 mL), potassium carbonate (0.75 g, 0.005 mol) was added and the mixture was refluxed in an oil bath for 4 hours. The reaction mixture was cooled and poured into water. The yellow solid which formed was filtered and recrystallized from aqueous ethanol to yield the title product. Yield: 12.2 g, (76%), mp: 72°–73° C. $^1$H NMR (CDCl$_3$) δ 1.62 and 1.78 (s, 6H, CH$_3$), 2.78 (d, 1H, OH), 3.4 and 3.58 (m, 2H, CHOHCH$_2$O), 4.0 (d, 1H, CHOH), 4.40 and 4.68 (m, 2H, CHOHCH$_2$N) 5.35 (m, 1H, >C=CH), 7.1 and 7.3 (s, 2H, imiH). Anal. calcd. for C$_{18}$H$_{17}$N$_3$O$_4$: C, 51.76; H, 7.71; N, 16.46. Found: C, 51.60; H, 6.48; N, 16.42.

C. 3-Chloro-1-[2-hydroxy-3-(2-nitro-1H-imidazol-1-yl]propoxy]-3-methyl-2-nitrosobutane To a cooled (0°–5° C.) stirred slurry of 1-[2-hydroxy-3-(2-nitro-1H-imidazol-1-yl)propyl-dimethylallyl ether (7.0 g, 0.0275 mol) in isoamyl nitrite (43 g, 50 mL, 0.042 mol) was added concentrated hydrochloric acid (2.5 mL, 0.03 mol) with stirring. The reaction mixture was maintained below 5° C. during the addition and stirred at 5° C. for an additional 2 hrs. The solid formed was stirred with cold ether-ethanol (3:1, 150 mL), filtered and dried under vacuum to yield the title product. Yield: 5.8 g (67%). mp: 116°–117° C. dec. $^1$H NMR (DMSO) δ 1.55 and 1.62 [s, 6H, CH$_3$], 3.35 (m, 4H, CH$_2$OCH$_2$CHOH), 3.82 (m, 1H, CHOH), 4.1–4.52 (m, 2H, CHOHCH$_2$N<), 5.3 (m, 1H, CHOH), 6.0 (dd, 1H, CHNO), 7.15 and 7.42 (s, 2H, imi H).

D. 3,3,9,9-Tetramethyl-1-[2-hydroxy-3-(2-nitro-1H-imidazol-1-yl)propoxy]-4,8-diazaundecane-2,10-dione dioxime A slurry of 3-chloro-1-[2-hydroxy-3-(2-nitro-1H-imidazol-1-yl)propoxy]-3-methyl-2-nitrosobutane (3.2 g, 0.01 mol) in acetonitrile (35 mL) was maintained at 40° C. for 30 minutes. To this slurry was added a solution of N-(3-aminopropyl)-1-amino-1,1-dimethyl-2-butanoneoxime (1.73 g, 0.01 mol) in acetonitrile (10 mL) and diisopropylethylamine (1.5 g, 0.012 mol) and the mixture was maintained at 40° C. for 48 hrs. The solid which formed was filtered and the acetonitrile solution was evaporated on a rotary evaporator to give a green viscous oil which was dried under vacuum. The foamy solid obtained was triturated with acetonitrile to afford a thick oil which solidified on standing. This was purified by column chromatography ($CH_2Cl_2$:$CH_3OH$, 7:3, 50:50)). The fractions containing the product were collected and evaporated to give an oil which was dried under vacuum and triturated with acetonitrile to give a white solid. It was recrystallized from ethyl acetate to yield the title product. Yield: 1.2 g (26%). mp: 134°-35° C. MS: (M+H)+=458+. $^1$H NMR (DMSO) δ 1.05 and 1.16 [s, 12H, $C(CH_3)_2$], 1.38 (m, 2H, $NHCH_2CH_2CH_2NH$), 1.72 (s, 3H, $CH_3$), 2.2 (m, 2H, $NHCH_2CH_2CH_2NH$), 3.38 (m, 4H, $CH_2OCH_2CHOH$), 3.8 (m, 2H, $OCH_2CHOH$), 4.28 and 4.6 (m, 3H, $CHOHCH_2N<$), 7.12 and 7.58 (s, 2H, imi H), 10.4 and 10.85 (s, 2H, NOH). Anal. Calcd for $C_{19}H_{35}N_7O_6$: C, 49.88; H, 7.71; N, 21.43. Found: C, 49.80; H, 7.79; N, 21.47.

Example 32

6-Hydroxy-3,3,9,9-tetramethyl-12-(2-nitro-1H-imidazol-1-yl)-4,8-diazadodecane-2,10-dione dioxime A. 4-Methyl-1-(2-nitro-1H-imidazol-1-yl)-3-pentene 5-Bromo-2-methyl-2-pentene (25 g, 0.154 mol) was dissolved in dry dimethylformamide (DMF) (200 mL). To the solution was added $K_2CO_3$ (21.3 g, 0.154 mol) and 2-nitroimidazole (17.4 g, 0.154 mol). The mixture was stirred under $N_2$ atmosphere at 75° C. for 48 hours. DMF was evaporated on a rotary evaporator. The yellow gummy residue was stirred with water (150 mL) to give yellow solid, which was dissolved in diethyl ether (150 mL), dried over $Na_2SO_4$ and evaporated on a rotary evaporator to yield the title product. Yield 27.8 g (92%). mp: 49°-51° C. MS: (M+H)+=196, M+=195. $^1$H NMR ($CDCl_3$) δ 1.45 and 1.68 (s, 6H, gem-di-$CH_3$), 2.52 (q, 2H, $CH_2CH=$), 4.43 [t, 2H, $CH_2$-(2-nitroimidazolyl)], 5.08 (t, 1H, $CH_2CH=$), 7.05 and 7.14 (s, 2H, 2-nitroimidazolyl-H).

B. 4-Chloro-4-methyl-1-(2-nitro-1H-imidazol-1-yl)-3-nitrosopentane

4-Methyl-1-(2-nitro-1H-imidazol-1-yl)-3-pentene (8 g, 41 mmol) was dissolved in isoamyl nitrite (50 mL) at room temperature. The solution was cooled to 0° C. in an ice-salt bath and concentrated HCl (12 mL) was added dropwise. The reaction temperature was maintained between 3°-5° C. during the HCl addition; the reaction was stirred in an ice-salt bath for 45 minutes after the addition of HCl. The product was filtered, washed with ethanol-ether (1:2) and dried in vacuum to give 8.6 g (81%) of the title product as a white solid; mp: 96°-97° C. MS: (M+H)+=261, M+=260. $^1$H NMR (DMSO-$d_6$) δ 1.70 (s, 6H, gem-di-$CH_3$), 2.94 (t, 2H, $CH_2C=NOH$), 4.65 [t, 2H, $CH_2$-(2-nitroimidazole)], 7.16 and 7.52 (s, 2H, 2-nitroimidazolyl-H), 11.43 (s, 1H, $CH_2C=NOH$).

C. 3-[3-Amino-2-hydroxy]propylamino-3-methyl-2-oximinobutane

To a stirring solution of 1,3-diamino-2-hydroxypropane (9.0 g, 0.1 mol) in acetonitrile (100 mL), was added anhydrous potassium carbonate (14.0 g 0.1 mol). The mixture was cooled to and 3-chloro-3-methyl-2-nitrosobutane (13.5 g, 0.1 mol) (prepared according to E. G. Vassian et al., *Inorg. Chem.*, 1967, 2043–2046) was added in portions over a period of 2 hours. After the addition, the reaction mixture was stirred at room temperature for 2 hours and then heated under reflux for 6 hours. The mixture was cooled and filtered and washed with acetonitrile. The combined organic layer was concentrated to a paste and treated with saturated methanolic HCl (100 mL). The solution was again concentrated to a paste and then crystallized from methanol twice to yield the title product as a colorless HCl salt. Yield: 10.5 g (48%). m.p.>185° C. (dec.). $^1$H NMR ($D_2O$) δ 1.45 (s, 6H, C—$CH_3$), 1.8 (s, 3H, N=C—$CH_3$), 3.0 (m, 4H, N—$CH_2$) and 4.1 (m, 1H, O—CH).

D. 6-hydroxy-3,3,9,9-tetramethyl-12-(2-nitro-1H-imidazol-1-yl)-4,8-diazadodecane-2,10-dione dioxime 3-[3-Amino-2-hydroxy]propylamino-3-methyl-2-oximinobutane hydrochloride (5.4 g, 0.25 mol) was neutralized with methanolic ammonia and evaporated to paste which was dried under vacuum for 2 hours at room temperature. The dried free base was suspended with stirring in dry acetonitrile (50 mL), treated with anhydrous potassium carbonate (3.5 g, 0.025 mol) and warmed to about 60° C. the above warm solution, 4-chloro-4-methyl-1-(2-nitro-1H-imidazol-1-yl)-3-nitrosopentane (7.0 g, 0.26 mol) was added all at once with stirring; the reaction temperature was maintained at 60° C. After the monooxime starting material had disappeared (16–20 hours), the mixture was filtered and washed with acetonitrile. The combined acetonitrile solution was concentrated to a paste and then chromatographed on a flash column. Elution with 85:15 EtOAc—$CH_3OH$ yielded the product as a yellow foam. The title product was repeatedly crystallized at −20° C. from a mixture of ethyl acetate (EtOAc)-acetonitrile until a single peak was observed on HPLC analysis. Yield: 4.0 g (91% pure, 25%). Yield of the pure product (99%): 0.3 g. m.p. 62°-64° C. $^1$H NMR (DMSO-$d_6$) δ 1.5 (s, 12 H, C—$CH_3$), 2.1 (s, 3H, N=C—$CH_3$), 2.7 (m, 4H, N—$CH_2$), 3.2 (t,2H, N=C—$CH_2$), 3.9 (bs, 1H, O—CH), 5.0 t, 2H, imid-$CH_2$), 7.45 (s, 1H, imid-H), 8.0 (1H, imid-H), 10.9 (s, 1H, N—OH) and 11.2 (s, 1H, N—OH). HRMS: Calcd for $C_{17}H_{32}N_7O_5$, 414.2476; Found, 414.2465. Anal. Calcd for $C_{17}H_{31}N_7O_5$·0.1 EtOAc C, 47.98; H, 7.87; N, 23.04. Found C, 48.48; H, 7.59; N, 22.54.

Example 33

4,4,10,10-Tetramethyl-1,13-bis(2-nitro-1H-imidazol-1-yl)-5,9-diazatridecane-3,11-dione dioxime To a solution of 1,3-diaminopropane (1.46 g, 15 mmol) in dry acetonitrile (50 mL) was added anhydrous potassium carbonate (4.2 g, 30 mmol) and the solution was brought to 50°-60° C. 4-Chloro-4-methyl-1-(2-nitroimidazol-1H-yl-3-nitrosopentane (3.9 g, 30 mmol, Example 3B) was added as a solid and the reaction mixture was stirred for 20 hours. The cooled solution was filtered and thoroughly washed with dry acetonitrile. The insoluble solid was ground to a powder and suspended in water with stirring. The water insoluble portion was filtered, washed with water and air dried, avoiding direct exposure to light. The resulting bright yellow solid was recrystallized from acetonitrile to yield the title product as a pale yellow solid. Yield: 2.6 g (33%). m.p. 101°-103° C. (dec.). $^1$H NMR (DMSO-$d_6$) δ 1.48 (s, 12H, C-methyls), 1.78 (m, 2H, N—CH$_2$—CH$_2$—CH$_2$—N), 2.58 (t, 4H, N=C—CH$_2$), 3.21 (t, 4H, N—CH$_2$), 4.98 (t, 4H, imi-CH$_2$), 7.58 (s, 2H, imi-H), 7.96 (s, 2H, imi-H) and 11.20 (s, N—OH). M. S. [M+H]$^+$ 524. HRMS Found: 523.2748; Calcd. 523.2741. Anal. Calc. C$_{21}$H$_{34}$N$_{10}$O$_6$·0.56 H$_2$O: C, 47.35; H, 6.65; N, 26.29. Found: C, 47.67; H, 6.48; N, 25.97.

Example 34

Synthesis of the $^{99m}$Tc Complexes of the Ligands of Examples 30 to 33

The $^{99m}$Tc complexes of the ligands prepared in Examples 30 to 33 above were prepared as follows:

Ligand (2–4 mg) was dissolved in 0.9% NaCl saline (1.0 mL) and 0.1M HCl (0.1 mL) in a 5 mL glass vial, and 0.1M sodium hydrogen carbonate buffer (0.5 mL), saline, and $^{99}$Mo/$^{99m}$Tc generator eluate (total saline/eluate volume=0.5 mL) was added. The vial was sealed, and a saturated solution of stannous tartrate in saline (50 μL) was added to the vial. The vial was shaken to mix the reagents, and allowed to stand at room temperature. The radiochemical purities (RCP) of the $^{99m}$Tc complexes were measured by reversed phase HPLC as described above. All technetium complexes formed with RCP>94% after 3 minutes, except for the $^{99m}$Tc complex of the ligand of Example 32, which formed more slowly (at 5 minutes the RCP was 68%; at 91 minutes the RCP had increased to 86%). The complexes so obtained from the ligands of Examples 30 to 33 were, respectively:

Oxo[[6,6-Difluoro-3,3,9,9-tetramethyl-12-(2-nitro-1H-imidazol-1-yl)-4,8-diazadodecane-2,10-dione dioximato](3-)-N,N',N",N'"]technetium-$^{99m}$Tc(V);

Oxo[[3,3,9,9-Tetramethyl-1-[2-hydroxy-3-(2-nitro-1H-imidazol-1-yl)propoxy]-4,8-diazaundecane-2,10-dione dioximato](3-)-N,N',N",N'"]technetium-$^{99m}$Tc(V);

Oxo[[6-hydroxy-3,3,9,9-tetramethyl-12-(2-nitro-1H-imidazol-1-yl)-4,8-diazadodecane-2,10-dione dioximato](3-)-N,N',N",N'"]-technetium-$^{99m}$Tc(V); and Oxo[[4,4,10,10-tetramethyl-1,13-bis(2-nitro-1H-imidazol-1-yl)-5,9-diazatridecane-3,11-dione dioximato](3-)-N,N',N",N'"]technetium-$^{99m}$Tc(V).

What is claimed is:

1. A method for the diagnostic imaging of hypoxic tissue in a mammalian species comprising the steps of:

administering a pharmaceutical formulation comprising a metal complex, said metal complex comprising a radionuclide of technetium and a ligand of either formula Ia or Ib:

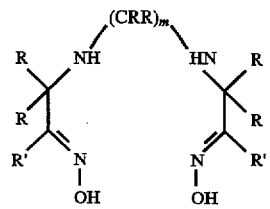

Ia

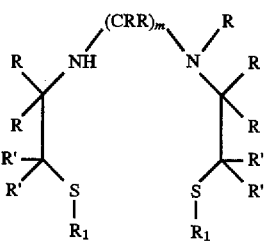

Ib wherein at least one R' is —(A)$_p$—R$_2$ where (A)$_p$ is a linking group and R$_2$ is a nitro-heterocyclic hypoxia localizing moiety; and wherein the other R' groups, that are not —(A)$_p$—R$_2$, and the R groups are the same, or different and are independently selected from hydrogen, halogen, hydroxy, alkyl, alkonyl, alkynyl, alkoxy, aryl, —COOR$_3$,

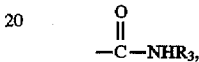

—NH$_2$, hydroxyalkyl, alkoxyalkyl, hydroxyaryl, haloalkyl, arylalkyl, alkyl—COOR$_3$, —alkyl—CON(R$_3$)$_2$, —alkyl—N(R$_3$)$_2$, —aryl—COOR$_3$, —aryl—CON(R$_3$)$_2$, —aryl—N(R$_3$)$_2$, 5- or 6-membered nitrogen- or oxygen-containing heterocycle; or two groups taken together with the one or more atoms to which they are attached form a carbocyclic or heterocyclic, saturated or unsaturated spiro or fused ring which may be substituted with R groups;

R$_1$ is hydrogen, a thiol protecting group or —(A)$_p$—R$_2$;

R$_3$ is hydrogen, alkyl or aryl;

m=2 t5;

p=0 t20; and where the term aryl denotes phenyl or substituted phenyl, and obtaining a diagnostic image of said hypoxic tissue.

2. The method of claim 1 used to diagnose ischemic tissue in the heart.

3. The method of claim 1 used to diagnose ischemic tissue in the lung.

4. The method of claim 1 used to diagnose ischemic tissue in the kidneys or liver.

5. The method of claim 1 used to diagnose ischemic tissue in the brain.

6. The method of claim 1 used to diagnose hypoxic tissue in tumors.

7. The method of claim 1 wherein the ligand has the name 3,3,9,9-tetramethyl-1-[2-hydroxy-3-(2-nitro-1H-imidazol-1-yl)propoxy]-4,8-diazaundecane-2,10-dione dioxime.

8. The method of claim 1 wherein the ligand has the name 3,3,9,9-tetramethyl-1-(2-nitro-1H-imidazol-1-yl)-4,8-diazaundecane-2,10-dione dioxime.

* * * * *